US007824893B2

(12) United States Patent
Deiters et al.

(10) Patent No.: US 7,824,893 B2
(45) **Date of Patent: *Nov. 2, 2010**

(54) IN VIVO INCORPORATION OF ALKYNYL AMINO ACIDS INTO PROTEINS IN EUBACTERIA

(75) Inventors: Alexander Deiters, Raleigh, NC (US); Peter G. Schultz, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 160 days.

This patent is subject to a terminal disclaimer.

(21) Appl. No.: 11/663,513

(22) PCT Filed: Sep. 20, 2005

(86) PCT No.: PCT/US2005/033784

§ 371 (c)(1), (2), (4) Date: Jun. 18, 2007

(87) PCT Pub. No.: WO2006/034332

PCT Pub. Date: Mar. 30, 2006

(65) Prior Publication Data

US 2008/0220472 A1 Sep. 11, 2008

Related U.S. Application Data

(60) Provisional application No. 60/612,220, filed on Sep. 21, 2004, provisional application No. 60/630,876, filed on Nov. 24, 2004, provisional application No. 60/634,151, filed on Dec. 7, 2004.

(51) Int. Cl.
*C12P 21/04* (2006.01)
*C12N 1/20* (2006.01)
*C12N 9/00* (2006.01)

(52) U.S. Cl. ................. 435/183; 435/252.1; 435/252.3; 435/252.8; 435/320.1; 536/23.2

(58) Field of Classification Search ....................... None
See application file for complete search history.

(56) References Cited

U.S. PATENT DOCUMENTS

| | | | |
|---|---|---|---|
| 6,927,042 | B2 | 8/2005 | Schultz et al. |
| 7,045,337 | B2 | 5/2006 | Schultz et al. |
| 7,083,970 | B2 | 8/2006 | Schultz et al. |
| 7,129,333 | B2 | 10/2006 | Schultz et al. |
| 2003/0108885 | A1 | 6/2003 | Schultz et al. |
| 2004/0265952 | A1 | 12/2004 | Deiters et al. |

FOREIGN PATENT DOCUMENTS

| | | | |
|---|---|---|---|
| WO | 02/085923 | A2 | 10/2002 |
| WO | 02/086075 | A2 | 10/2002 |
| WO | 2004/035605 | A2 | 4/2004 |
| WO | 2004/035743 | A2 | 4/2004 |
| WO | 2004/058946 | A2 | 7/2004 |
| WO | 2004/094593 | A2 | 11/2004 |
| WO | 2005/003294 | A2 | 1/2005 |
| WO | 2005/007624 | A2 | 1/2005 |
| WO | 2005/007870 | A2 | 1/2005 |
| WO | 2005/019415 | A2 | 3/2005 |
| WO | 2006/110182 | A2 | 10/2006 |

OTHER PUBLICATIONS

Alfonta et al. (2003)•(2003) "Site-Specific Incorporation of a Redox Active Amino Acid into Proteins," *J. Am. Chem. Soc.* ,125(48):14662-14663.

Anderson et al. (2004) "An expanding genetic code with functional quadruplet codon," *PNAS*, 101(20) 7566-7571.

Chin and Schultz, (2002) "In vivo Photocrosslinking with Unnatural Amino Acid Mutagenesis," *ChemBioChem* 11:1135-1137.

Chin et al. (2002) "Addition of a photocrosslinking amino acid to the genetic code of *Escherichia coli." PNAS*, 99(17):11020-11024.

Chin et al. (2002) "Addition of p-Azido-L-phenylalanine to the genetic code of *Escherichia coli." J Am Chem Soc* 124:9026-9027.

Chin et al. (2003) "An Expanded Eukaryotic Genetic Code." *Science*, 301:964-967.

Deiters et al. (2003) "Adding Amino Acids with Novel Reactivity to the Genetic Code of *Saccharomyces Cerevisiae," J. Am. Chem. Soc.*, 125:11782-11783.

Deiters et al. (2004) "Site-specific PEGylation of proteins containing unnatural amino acids," *Bioorganic & Medicinal Chemistry Letters*,14:5743-5745.

Deiters et al. (2005) "In vivo incorporation of an alkyne into proteins in *Escherichia coli," Bioorganic & Medicinal Chemistry Letters*,15:1521-1524.

Feng et al. (2003) "Expanding tRNA recognition of a tRNA synthetase by a single amino acid change." *PNAS* 100(10): 5676-5681.

Forster et al. (2003) "Programming peptidomimetic synthetases by translating genetic codes designed de novo." *PNAS* 100(11):6353-6357.

Francklyn et al. (2002) "Aminoacyl-tRNA synthetases: Versatile players in the changing theater of translation." *RNA*, 8(11):1363-1372.

Hirao et al. (2002) "An unnatural base pair for incorporating amino acid analogues into protein," *Nature Biotechnology*, 20(2):177-182.

Hoben and Soll (1985) "Glutaminyl-tRNA synthetase of *Escherichia coli," Methods Enzymol.* 113:55-59.

Huisgen. "1,3, Dipolar Cycloadditions—Introduction, Survey, Mechanism," *1,3-Dipolar Cycloaddition Chemistry*, [Padwa, A., Ed.] Wiley: New York, 1984; v.1,p. 1-176.

Ibba. (1996) "Strategies for in vitro and in vivo translation with non-natural amino acids." Biotechnol Gente Eng. Rev. 13:197-216.

(Continued)

*Primary Examiner*—Manjunath N Rao
*Assistant Examiner*—Kagnew H Gebreyesus
(74) *Attorney, Agent, or Firm*—Quine Intellectual Property Law Group; Gary Baker

(57) ABSTRACT

The invention relates to orthogonal pairs of tRNAs and aminoacyl-tRNA synthetases that can incorporate alkynyl amino acids such as para-propargyloxyphenylalanine into proteins produced in a eubacteria host such as *E. coli*. The invention provides novel orthoghonal synthetases, methods for identifying and making the novel synthetases, methods for producing proteins containing alkynyl amino acids, and cellular translation systems.

17 Claims, 8 Drawing Sheets

OTHER PUBLICATIONS

Kiga et al. (2002) "An engineered *Escherichia coli* tyrosyl-tRNA synthetase for site-specific incorporation of an unnatural amino acid into proteins in eukaryotic translation and its application in a wheat germ cell-free system." *PNAS*, 99(15): 9715-9720.
Kowal et al. (2001) "Twenty-first aminoacyl-tRNA synthetase-suppressor tRNA pairs for possible use in site-specific incorporation of amino acid analogues into proteins in eukaryotes and in eubacteria." *Proc. Natl. Acad. Sci. U S A*, 98(5):2268-2273.
Link and Tirrell. (2003) "Cell surface labeling of *Escherichia coli* via copper(I)-catalyzed [3+2] cycloaddition," *J. Am. Chem. Soc.*, 125(37):11164-11165.
Liu & Schultz. (1999) "Progress toward the evolution of an organism with an expanded genetic code." *PNAS*, 96(9):4780-4785.
Ohno et al. (1998) "Co-expression of yeast amber suppressor tRNATyr and tyrosyl-tRNA synthetase in *Escherichia coli*: possibility to expand the genetic code," *J. Biochem.* 124(6): 1065-1068.
Padwa. "Intermolecular 1,3-Dipolar Cycloadditions," *Comprehensive Organic Synthesis*, Trost, B.M.; Fleming, I. (Eds.), Pergamon Press, Oxford, 1991, vol. 4, pp. 1069-1109.
Rostovtsev et al. (2002) "A stepwise Huisgen cycloaddition process: copper(I)catalyzed regioselective "ligation" of azides and terminal alkynes." *Angew Chem Int Ed* 41:2596-2599.
Tornoe et al. (2002) "Peptidotriazoles on solid phase: [1,2,3]-triazoles by regiospecific copper(i)-catalyzed 1,3-dipolar cycloadditions of terminal alkynes to azides," *J. Org. Chem.*, 67(9):3057-3064.
Van Maarseveen & Back (2003) "Engineering des genetischen Codes: Molekularbiologie and Organiche Chemie kombiniert," *Angew. Chem.*, 115:6106-6106.
Wang & Schultz (2001) "A General Approach for the Generation of Orthogonal tRNAs," *Chem. Biol.* 8:883-890.
Wang & Schultz. (2002) "Expanding the genetic code," *Chem. Commun.*, 1:1-11.
Wang & Schultz. (2004) "Expanding the genetic code," *Ang. Chem. Int. Ed.*, 44(1):34-66.
Wang et al. (2000) "A new functional suppressor tRNA/aminoacyl-tRNA synthetase pair for the in vivo incorporation of unnatural amino acids into proteins," *J. Am. Chem. Soc.* 122:5010-5011.
Wang et al. (2001) "Expanding the genetic code of *Escherichia coli.*" *Science*, 292(5516):498-500.
Wang et al. (2003) "Addition of the keto functional croup to the genetic code of *Escherichia coli." PNAS*, 100(1):56-61.
Wang et al. (2003) "Bioconjugation by copper(I)-catalyzed azide-alkyne [3+2] cycloaddition," *J. Am. Chem. Soc.*, 125(11):3192-3193.
Wu et al. (2002) "Enzymatic phosphorylation of unnatural nucleosides," *J. Am. Chem. Soc.* 124(49)14626-14630.
Xie & Schultz. (2005) "An expanding genetic code," *Methods*, 36(3):227-238.
Zhang et al. (2003) "A New Strategy for the Site-Specific Modification of Proteins in Vivo." *Biochemistry*, 42(22):6735-6746.
Zhang et al. (2002) "The Selective Incorporation of Alkenes into Proteins in *Escherichia coli." Angew. Chem. Int. Ed. Engl.* 41(15):2840-2842.
Cropp et al., "An Expanding Genetic Code", Trends in Genetics, vol. 20, No. 12, pp. 625- 630 (2004).
Kobayashi et al., "Structural Basis for Orthogonal tRNA Specificities of Tyrosyl-tRNA Synthetases for Genetic Code Expansion", Nature Structural Biology, vol. 10, No. 6, pp. 425-432 (2003).

1/1 31/11 61/21 91/31
ATG GAC GAA TTT GAA ATG ATA AAG AGA AAC ACA TCT GAA ATT ATC AGC GAG GAA GAG TTA AGA GAG GTT TTA AAA AAA GAT GAA AAA TCT GCT TAC ATA GGT TTT GAA CCA AGT GGT AAA
Met asp glu phe glu met ile lys arg asn thr ser glu ile ile ser glu glu glu leu arg glu val leu lys lys asp glu lys ser ala tyr ile gly phe glu pro ser gly lys 121/41 151/51 181/61 211/71
ATA CAT TTA GGG CAT TAT CTC CAA ATA AAA AAG ATG ATT GAT TTA CAA AAT GCT GGA TTT GAT ATA ATT ATA TTG TTG GCT GAT TTA CAC GCC TAT TTA AAC CAG AAA GGA GAG TTG GAT
ile his leu gly his tyr leu gln ile lys lys met ile asp leu gln asn ala gly phe asp ile ile ile leu leu ala asp leu his ala tyr leu asn gln lys gly glu leu asp 241/81 271/91 301/101 331/111
GAG ATT AGA AAA ATA GGA GAT TAT AAC AAA AAA GTT TTT GAA GCA ATG GGG TTA AAG GCA AAA TAT GTT TAT GGA AGT GAA TTC CAG CTT GAT AAG GAT TAT ACA CTG AAT GTC TAT AGA
glu ile arg lys ile gly asp tyr asn lys lys val phe glu ala met gly leu lys ala lys tyr val tyr gly ser glu phe gln leu asp lys asp tyr thr leu asn val tyr arg 361/121 391/131 421/141 451/151
TTG GCT TTA AAA ACT ACC TTA AAA AGA GCA AGA AGG AGT ATG GAA CTT ATA GCA AGA GAG GAT GAA AAT CCA AAG GTT GCT GAA GTT ATC TAT CCA ATA ATG CAG GTT AAT GAT ATT CAT
leu ala leu lys thr thr leu lys arg ala arg arg ser met glu leu ile ala arg glu asp glu asn pro lys val ala glu val ile tyr pro ile met gln val asn asp ile his 481/161 511/171 541/181 571/191
TAT TTA GGC GTT GAT GTT GCA GTT GGA GGG ATG GAG CAG AGA AAA ATA CAC ATG TTA GCA AGG GAG CTT TTA CCA AAA AAG GTT GTT TGT ATT CAC AAC CCT GTC TTA ACG GGT TTG GAT
tyr leu gly val asp val ala val gly gly met glu gln arg lys ile his met leu ala arg glu leu leu pro lys lys val val cys ile his asn pro val leu thr gly leu asp 601/201 631/211 661/221 691/231
GGA GAA GGA AAG ATG AGT TCT TCA AAA GGG AAT TTT ATA GCT GTT GAT GAC TCT CCA GAA GAG ATT AGG GCT AAG ATA AAG AAA GCA TAC TGC CCA GCT GGA GTT GTT GAA GGA AAT CCA
gly glu gly lys met ser ser ser lys gly asn phe ile ala val asp asp ser pro glu glu ile arg ala lys ile lys lys ala tyr cys pro ala gly val val glu gly asn pro 721/241 751/251 781/261 811/271
ATA ATG GAG ATA GCT AAA TAC TTC CTT GAA TAT CCT TTA ACC ATA AAA AGG CCA GAA AAA TTT GGT GGA GAT TTG ACA GTT AAT AGC TAT GAG GAG TTA GAG AGT TTA TTT AAA AAT AAG
ile met glu ile ala lys tyr phe leu glu tyr pro leu thr ile lys arg pro glu lys phe gly gly asp leu thr val asn ser tyr glu glu leu glu ser leu phe lys asn lys 841/281 871/291 901/301
GAA TTG CAT CCA ATG GAT TTA AAA AAT GCT GTA GCT GAA GAA CTT ATA AAG ATT TTA GAG CCA ATT AGA AAG AGA TTA (SEQ ID NO:3)
glu leu his pro met asp leu lys asn ala val ala glu glu leu ile lys ile leu glu pro ile arg lys arg leu (SEQ ID NO:2)

| | Amino Acid Position | | | | | | |
|---|---|---|---|---|---|---|---|
| ***Methanococcus jannaschii* tyrosyl-tRNA synthetase species** | **32** | **107** | **110** | **158** | **159** | **162** | **SEQ ID NO:** |
| wild type | Tyr (TAC) | Glu (GAA) | Leu (CTT) | Asp (GAT) | Ile (ATT) | Leu (TTA) | **2** |
| pPRO-PheRS-1 | Ala (GCG) | Pro (CCG) | Phe (TTT) | Ala (GCA) | Ile (ATT) | Ala (GCT) | **4** |
| pPRO-PheRS-2 | Ala (GCG) | Lys (AAG) | Leu (CTT) | Ala (GCA) | Ile (ATT) | Ala (GCC) | **6** |
| pPRO-PheRS-3 | Ala (GCG) | Arg (CGG) | Leu (CTT) | Ala (GCA) | Ile (ATT) | Pro (CCG) | **8** |
| pPRO-PheRS-4 | His (CAT) | Ala (GCT) | Leu (CTT) | Ala (GCA) | Ile (ATT) | Pro (CCT) | **10** |
| pPRO-PheRS-5 | Ser (TCG) | Gln (CAG) | Leu (CTT) | Ala (GCA) | Ile (ATT) | Ala (GCC) | **12** |
| pPRO-PheRS-6 | Thr (ACG) | Ser (TCG) | Leu (CTT) | Leu (CTT) | His (CAT) | Pro (CCG) | **14** |
| pPRO-PheRS-7 | Ala (GCT) | Gln (CAG) | Leu (CTT) | Pro (CCG) | Gly (GGG) | Thr (ACG) | **16** |
| pPRO-PheRS-8 | Ala (GCT) | Pro (CCT) | Leu (CTT) | Ser (TCT) | Leu (CTG) | His (CAT) | **18** |
| pPRO-PheRS-consensus | Ala | Pro/Gln | Leu | Ala | Ile | Ala/Pro | **21** |

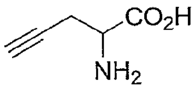
2-amino-4-pentynoic acid
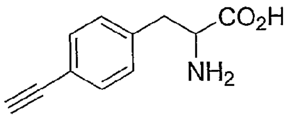
2-amino-3-(4-ethynylphenyl)propanoic acid
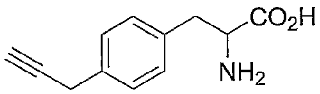
2-amino-3-[4-(prop-2-ynyl)phenyl]propanoic acid
Fig. 8A
Potential alkyne amino acids derived from natural amino acids:
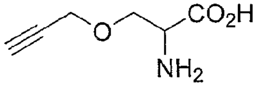
2-amino-3-(prop-2-ynyloxy)propanoic acid
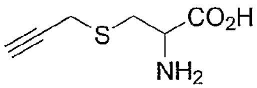
2-amino-3-(prop-2-ynylthio)propanoic acid
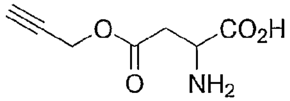
3-[(prop-2-ynyloxy)carbonyl]-2-aminopropanoic acid
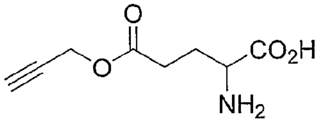
4-[(prop-2-ynyloxy)carbonyl]-2-aminobutanoic acid
Fig. 8B

SEQUENCE LISTING

<160> NUMBER OF SEQ ID NOS: 25

<210> SEQ ID NO 1
<211> LENGTH: 77
<212> TYPE: RNA
<213> ORGANISM: Artificial
<220> FEATURE:
<223> OTHER INFORMATION: mutant tRNA

<400> SEQUENCE: 1

```
ccggcgguag uucagcaggg cagaacggcg gacucuaaau ccgcauggcg cugguucaaa     60

uccggcccgc cggacca                                                    77
```

<210> SEQ ID NO 2
<211> LENGTH: 306
<212> TYPE: PRT
<213> ORGANISM: Methanococcus jannaschii

<400> SEQUENCE: 2

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Tyr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 210
```

-continued

```
Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 3
<211> LENGTH: 918
<212> TYPE: DNA
<213> ORGANISM: Methanococcus jannaschii

<400> SEQUENCE: 3

atggacgaat ttgaaatgat aaagagaaac acatctgaaa ttatcagcga ggaagagtta      60

agagaggttt taaaaaaaga tgaaaaatct gcttacatag gttttgaacc aagtggtaaa     120

atacatttag ggcattatct ccaaataaaa aagatgattg atttacaaaa tgctggattt     180

gatataatta tattgttggc tgatttacac gcctatttaa accagaaagg agagttggat     240

gagattagaa aaataggaga ttataacaaa aaagtttttg aagcaatggg gttaaaggca     300

aaatatgttt atggaagtga attccagctt gataaggatt atacactgaa tgtctataga     360

ttggctttaa aaactacctt aaaaagagca agaaggagta tggaacttat agcaagagag     420

gatgaaaatc caaaggttgc tgaagttatc tatccaataa tgcaggttaa tgatattcat     480

tatttaggcg ttgatgttgc agttggaggg atggagcaga gaaaaataca catgttagca     540

agggagcttt taccaaaaaa ggttgtttgt attcacaacc ctgtcttaac gggtttggat     600

ggagaaggaa agatgagttc ttcaaaaggg aattttatag ctgttgatga ctctccagaa     660

gagattaggg ctaagataaa gaaagcatac tgcccagctg gagttgttga aggaaatcca     720

ataatggaga tagctaaata cttccttgaa tatcctttaa ccataaaaag gccagaaaaa     780

tttggtggag atttgacagt taatagctat gaggagttag agagtttatt taaaaataag     840

gaattgcatc caatggattt aaaaaatgct gtagctgaag aacttataaa gattttagag     900

ccaattagaa agagatta                                                   918


<210> SEQ ID NO 4
<211> LENGTH: 306
<212> TYPE: PRT
<213> ORGANISM: Artificial
<220> FEATURE:
<223> OTHER INFORMATION: para-propargyloxyphenylalanine aminoacyl-tRNA
      synthetase derived from M. jannaschii tyrosyl tRNA-synthetase

<400> SEQUENCE: 4

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30
```

-continued

```
Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Phe Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile His
145                 150                 155                 160

Tyr Ala Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 5
<211> LENGTH: 918
<212> TYPE: DNA
<213> ORGANISM: Artificial
<220> FEATURE:
<223> OTHER INFORMATION: para-propargyloxyphenylalanine aminoacyl-tRNA synthetase derived from M. jannaschii tyrosyl tRNA-synthetase

<400> SEQUENCE: 5

```
atggacgaat ttgaaatgat aaagagaaac acatctgaaa ttatcagcga ggaagagtta     60

agagaggttt taaaaaaaga tgaaaaatct gctgcgatag gttttgaacc aagtggtaaa    120

atacatttag ggcattatct ccaaataaaa aagatgattg atttacaaaa tgctggattt    180

gatataatta tattgttggc tgatttacac gcctatttaa accagaaagg agagttggat    240

gagattagaa aaataggaga ttataacaaa aaagtttttg aagcaatggg gttaaaggca    300

aaatatgttt atggaagtcc gttccagttt gataaggatt atacactgaa tgtctataga    360

ttggctttaa aaactacctt aaaaagagca agaaggagta tggaacttat agcaagagag    420
```

-continued

```
gatgaaaatc caaaggttgc tgaagttatc tatccaataa tgcaggttaa tgcaattcat    480

tatgctggcg ttgatgttgc agttggaggg atggagcaga gaaaaataca catgttagca    540

agggagcttt taccaaaaaa ggttgtttgt attcacaacc ctgtcttaac gggtttggat    600

ggagaaggaa agatgagttc ttcaaaaggg aattttatag ctgttgatga ctctccagaa    660

gagattaggg ctaagataaa gaaagcatac tgcccagctg gagttgttga aggaaatcca    720

ataatggaga tagctaaata cttccttgaa tatcctttaa ccataaaaag gccagaaaaa    780

tttggtggag atttgacagt taatagctat gaggagttag agagtttatt taaaaataag    840

gaattgcatc caatggattt aaaaaatgct gtagctgaag aacttataaa gattttagag    900

ccaattagaa agagatta                                                   918
```

```
<210> SEQ ID NO 6
<211> LENGTH: 306
<212> TYPE: PRT
<213> ORGANISM: Artificial
<220> FEATURE:
<223> OTHER INFORMATION: para-propargyloxyphenylalanine aminoacyl-tRNA
      synthetase derived from M. jannaschii tyrosyl tRNA-synthetase

<400> SEQUENCE: 6

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Lys Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile His
145                 150                 155                 160

Tyr Ala Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270
```

-continued

```
Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 7
<211> LENGTH: 918
<212> TYPE: DNA
<213> ORGANISM: Artificial
<220> FEATURE:
<223> OTHER INFORMATION: para-propargyloxyphenylalanine aminoacyl-tRNA
      synthetase derived from M. jannaschii tyrosyl tRNA-synthetase

<400> SEQUENCE: 7

atggacgaat ttgaaatgat aaagagaaac acatctgaaa ttatcagcga ggaagagtta      60

agagaggttt taaaaaaaga tgaaaaatct gctgcgatag gttttgaacc aagtggtaaa     120

atacatttag ggcattatct ccaaataaaa aagatgattg atttacaaaa tgctggattt     180

gatataatta tattgttggc tgatttacac gcctatttaa accagaaagg agagttggat     240

gagattagaa aaataggaga ttataacaaa aaagtttttg aagcaatggg gttaaaggca     300

aaatatgttt atggaagtaa gttccagctt gataaggatt atacactgaa tgtctataga     360

ttggctttaa aaactacctt aaaaagagca agaaggagta tggaacttat agcaagagag     420

gatgaaaatc caaaggttgc tgaagttatc tatccaataa tgcaggttaa tgcaattcat     480

tatgccggcg ttgatgttgc agttggaggg atggagcaga gaaaaataca catgttagca     540

agggagcttt taccaaaaaa ggttgtttgt attcacaacc ctgtcttaac gggtttggat     600

ggagaaggaa agatgagttc ttcaaaaggg aattttatag ctgttgatga ctctccagaa     660

gagattaggg ctaagataaa gaaagcatac tgcccagctg gagttgttga aggaaatcca     720

ataatggaga tagctaaata cttccttgaa tatcctttaa ccataaaaag gccagaaaaa     780

tttggtggag atttgacagt taatagctat gaggagttag agagtttatt taaaaataag     840

gaattgcatc caatggattt aaaaaatgct gtagctgaag aacttataaa gattttagag     900

ccaattagaa agagatta                                                   918


<210> SEQ ID NO 8
<211> LENGTH: 306
<212> TYPE: PRT
<213> ORGANISM: Artificial
<220> FEATURE:
<223> OTHER INFORMATION: para-propargyloxyphenylalanine aminoacyl-tRNA
      synthetase derived from M. jannaschii tyrosyl tRNA-synthetase

<400> SEQUENCE: 8

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80
```

-continued

```
Glu Ile Arg Lys Ile Gly Asp Tyr Asn Lys Lys Val Phe Glu Ala Met
                85                  90                  95

Gly Leu Lys Ala Lys Tyr Val Tyr Gly Ser Arg Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile His
145                 150                 155                 160

Tyr Pro Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 9
<211> LENGTH: 918
<212> TYPE: DNA
<213> ORGANISM: Artificial
<220> FEATURE:
<223> OTHER INFORMATION: para-propargyloxyphenylalanine aminoacyl-tRNA synthetase derived from M. jannaschii tyrosyl tRNA-synthetase

<400> SEQUENCE: 9

```
atggacgaat ttgaaatgat aaagagaaac acatctgaaa ttatcagcga ggaagagtta     60

agagaggttt taaaaaaaga tgaaaaatct gctgcgatag gttttgaacc aagtggtaaa    120

atacatttag ggcattatct ccaaataaaa aagatgattg atttacaaaa tgctggattt    180

gatataatta tattgttggc tgatttacac gcctatttaa accagaaagg agagttggat    240

gagattagaa aaataggaga ttataacaaa aaagtttttg aagcaatggg gttaaaggca    300

aaatatgttt atggaagtcg gttccagctt gataaggatt atacactgaa tgtctataga    360

ttggctttaa aaactacctt aaaaagagca agaaggagta tggaacttat agcaagagag    420

gatgaaaatc caaaggttgc tgaagttatc tatccaataa tgcaggttaa tgcaattcat    480

tatccgggcg ttgatgttgc agttggaggg atggagcaga gaaaaataca catgttagca    540

agggagcttt taccaaaaaa ggttgtttgt attcacaacc ctgtcttaac gggtttggat    600

ggagaaggaa agatgagttc ttcaaaaggg aattttatag ctgttgatga ctctccagaa    660

gagattaggg ctaagataaa gaaagcatac tgcccagctg gagttgttga aggaaatcca    720
```

-continued

```
ataatggaga tagctaaata cttccttgaa tatcctttaa ccataaaaag gccagaaaaa    780

tttggtggag atttgacagt taatagctat gaggagttag agagtttatt taaaaataag    840

gaattgcatc caatggattt aaaaaatgct gtagctgaag aacttataaa gattttagag    900

ccaattagaa agagatta                                                  918


<210> SEQ ID NO 10
<211> LENGTH: 306
<212> TYPE: PRT
<213> ORGANISM: Artificial
<220> FEATURE:
<223> OTHER INFORMATION: para-propargyloxyphenylalanine aminoacyl-tRNA
      synthetase derived from M. jannaschii tyrosyl tRNA-synthetase

<400> SEQUENCE: 10

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala His
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ala Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile His
145                 150                 155                 160

Tyr Pro Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

-continued

```
<210> SEQ ID NO 11
<211> LENGTH: 918
<212> TYPE: DNA
<213> ORGANISM: Artificial
<220> FEATURE:
<223> OTHER INFORMATION: para-propargyloxyphenylalanine aminoacyl-tRNA
      synthetase derived from M. jannaschii tyrosyl tRNA-synthetase

<400> SEQUENCE: 11

atggacgaat ttgaaatgat aaagagaaac acatctgaaa ttatcagcga ggaagagtta      60

agagaggttt taaaaaaaga tgaaaaatct gctcatatag gttttgaacc aagtggtaaa     120

atacatttag ggcattatct ccaaataaaa aagatgattg atttacaaaa tgctggattt     180

gatataatta tattgttggc tgatttacac gcctatttaa accagaaagg agagttggat     240

gagattagaa aaataggaga ttataacaaa aaagtttttg aagcaatggg gttaaaggca     300

aaatatgttt atggaagtgc tttccagctt gataaggatt atacactgaa tgtctataga     360

ttggctttaa aaactacctt aaaaagagca agaaggagta tggaacttat agcaagagag     420

gatgaaaatc caaaggttgc tgaagttatc tatccaataa tgcaggttaa tgcaattcat     480

tatcctggcg ttgatgttgc agttggaggg atggagcaga gaaaaataca catgttagca     540

agggagcttt taccaaaaaa ggttgtttgt attcacaacc ctgtcttaac gggtttggat     600

ggagaaggaa agatgagttc ttcaaaaggg aattttatag ctgttgatga ctctccagaa     660

gagattaggg ctaagataaa gaaagcatac tgcccagctg gagttgttga aggaaatcca     720

ataatggaga tagctaaata cttccttgaa tatcctttaa ccataaaaag gccagaaaaa     780

tttggtggag atttgacagt taatagctat gaggagttag agagtttatt taaaaataag     840

gaattgcatc caatggattt aaaaaatgct gtagctgaag aacttataaa gattttagag     900

ccaattagaa agagatta                                                   918


<210> SEQ ID NO 12
<211> LENGTH: 306
<212> TYPE: PRT
<213> ORGANISM: Artificial
<220> FEATURE:
<223> OTHER INFORMATION: para-propargyloxyphenylalanine aminoacyl-tRNA
      synthetase derived from M. jannaschii tyrosyl tRNA-synthetase

<400> SEQUENCE: 12

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ser
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Gln Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140
```

-continued

```
Lys Val Ala Glu Val Ile Tyr Pro Ile Met Gln Val Asn Ala Ile His
145                 150                 155                 160

Tyr Ala Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

```
<210> SEQ ID NO 13
<211> LENGTH: 918
<212> TYPE: DNA
<213> ORGANISM: Artificial
<220> FEATURE:
<223> OTHER INFORMATION: para-propargyloxyphenylalanine aminoacyl-tRNA
      synthetase derived from M. jannaschii tyrosyl tRNA-synthetase

<400> SEQUENCE: 13

atggacgaat ttgaaatgat aaagagaaac acatctgaaa ttatcagcga ggaagagtta     60

agagaggttt taaaaaaaga tgaaaaatct gcttcgatag gttttgaacc aagtggtaaa    120

atacatttag ggcattatct ccaaataaaa aagatgattg atttacaaaa tgctggattt    180

gatataatta tattgttggc tgatttacac gcctatttaa accagaaagg agagttggat    240

gagattagaa aaataggaga ttataacaaa aaagtttttg aagcaatggg gttaaaggca    300

aaatatgttt atggaagtca gttccagctt gataaggatt atacactgaa tgtctataga    360

ttggctttaa aaactacctt aaaaagagca agaaggagta tggaacttat agcaagagag    420

gatgaaaatc caaaggttgc tgaagttatc tatccaataa tgcaggttaa tgcaattcat    480

tatgccggcg ttgatgttgc agttggaggg atggagcaga gaaaaataca catgttagca    540

agggagcttt taccaaaaaa ggttgtttgt attcacaacc ctgtcttaac gggtttggat    600

ggagaaggaa agatgagttc ttcaaaaggg aattttatag ctgttgatga ctctccagaa    660

gagattaggg ctaagataaa gaaagcatac tgcccagctg gagttgttga aggaaatcca    720

ataatggaga tagctaaata cttccttgaa tatcctttaa ccataaaaag gccagaaaaa    780

tttggtggag atttgacagt taatagctat gaggagttag agagtttatt taaaaataag    840

gaattgcatc caatggattt aaaaaatgct gtagctgaag aacttataaa gattttagag    900

ccaattagaa agagatta                                                  918
```

-continued

<210> SEQ ID NO 14
<211> LENGTH: 306
<212> TYPE: PRT
<213> ORGANISM: Artificial
<220> FEATURE:
<223> OTHER INFORMATION: para-propargyloxyphenylalanine aminoacyl-tRNA
synthetase derived from M. jannaschii tyrosyl tRNA-synthetase

<400> SEQUENCE: 14

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Leu His His
145                 150                 155                 160

Tyr Pro Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 15
<211> LENGTH: 918
<212> TYPE: DNA
<213> ORGANISM: Artificial
<220> FEATURE:
<223> OTHER INFORMATION: para-propargyloxyphenylalanine aminoacyl-tRNA
synthetase derived from M. jannaschii tyrosyl tRNA-synthetase -continued

<400> SEQUENCE: 15

```
atggacgaat ttgaaatgat aaagagaaac acatctgaaa ttatcagcga ggaagagtta     60

agagaggttt taaaaaaaga tgaaaaatct gctacgatag gttttgaacc aagtggtaaa    120

atacatttag ggcattatct ccaaataaaa aagatgattg atttacaaaa tgctggattt    180

gatataatta tattgttggc tgatttacac gcctatttaa accagaaagg agagttggat    240

gagattagaa aaataggaga ttataacaaa aaagtttttg aagcaatggg gttaaaggca    300

aaatatgttt atggaagttc gttccagctt gataaggatt atacactgaa tgtctataga    360

ttggctttaa aaactacctt aaaaagagca agaaggagta tggaacttat agcaagagag    420

gatgaaaatc caaaggttgc tgaagttatc tatccaataa tgcaggttaa tcttcatcat    480

tatccgggcg ttgatgttgc agttggaggg atggagcaga gaaaaataca catgttagca    540

agggagcttt taccaaaaaa ggttgtttgt attcacaacc ctgtcttaac gggtttggat    600

ggagaaggaa agatgagttc ttcaaaaggg aattttatag ctgttgatga ctctccagaa    660

gagattaggg ctaagataaa gaaagcatac tgcccagctg gagttgttga aggaaatcca    720

ataatggaga tagctaaata cttccttgaa tatcctttaa ccataaaaag gccagaaaaa    780

tttggtggag atttgacagt taatagctat gaggagttag agagtttatt taaaaataag    840

gaattgcatc caatggattt aaaaaatgct gtagctgaag aacttataaa gattttagag    900

ccaattagaa agagatta                                                  918
```

<210> SEQ ID NO 16
<211> LENGTH: 306
<212> TYPE: PRT
<213> ORGANISM: Artificial
<220> FEATURE:
<223> OTHER INFORMATION: para-propargyloxyphenylalanine aminoacyl-tRNA synthetase derived from M. jannaschii tyrosyl tRNA-synthetase

<400> SEQUENCE: 16

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Gln Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Gly His
145                 150                 155                 160

Tyr Thr Gly Val Asp Val Ala Val Gly Gly Met Glu Gln Arg Lys Ile
                165                 170                 175
```

-continued

```
His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 17
<211> LENGTH: 918
<212> TYPE: DNA
<213> ORGANISM: Artificial
<220> FEATURE:
<223> OTHER INFORMATION: para-propargyloxyphenylalanine aminoacyl-tRNA
      synthetase derived from M. jannaschii tyrosyl tRNA-synthetase

<400> SEQUENCE: 17

atggacgaat ttgaaatgat aaagagaaac acatctgaaa ttatcagcga ggaagagtta      60

agagaggttt taaaaaaaga tgaaaaatct gctgctatag gttttgaacc aagtggtaaa     120

atacatttag ggcattatct ccaaataaaa aagatgattg atttacaaaa tgctggattt     180

gatataatta tattgttggc tgatttacac gcctatttaa accagaaagg agagttggat     240

gagattagaa aaataggaga ttataacaaa aaagtttttg aagcaatggg gttaaaggca     300

aaatatgttt atggaagtca gttccagctt gataaggatt atacactgaa tgtctataga     360

ttggctttaa aaactacctt aaaaagagca agaaggagta tggaacttat agcaagagag     420

gatgaaaatc caaaggttgc tgaagttatc tatccaataa tgcaggttaa tccggggcat     480

tatacgggcg ttgatgttgc agttggaggg atggagcaga gaaaaataca catgttagca     540

agggagcttt taccaaaaaa ggttgtttgt attcacaacc ctgtcttaac gggtttggat     600

ggagaaggaa agatgagttc ttcaaaaggg aattttatag ctgttgatga ctctccagaa     660

gagattaggg ctaagataaa gaaagcatac tgcccagctg gagttgttga aggaaatcca     720

ataatggaga tagctaaata cttccttgaa tatcctttaa ccataaaaag gccagaaaaa     780

tttggtggag atttgacagt taatagctat gaggagttag agagtttatt taaaaataag     840

gaattgcatc caatggattt aaaaaatgct gtagctgaag aacttataaa gattttagag     900

ccaattagaa agagatta                                                   918


<210> SEQ ID NO 18
<211> LENGTH: 306
<212> TYPE: PRT
<213> ORGANISM: Artificial
<220> FEATURE:
<223> OTHER INFORMATION: para-propargyloxyphenylalanine aminoacyl-tRNA
      synthetase derived from M. jannaschii tyrosyl tRNA-synthetase
```

-continued

<400> SEQUENCE: 18

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ser Leu His
145                 150                 155                 160

Tyr His Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 19
<211> LENGTH: 918
<212> TYPE: DNA
<213> ORGANISM: Artificial
<220> FEATURE:
<223> OTHER INFORMATION: para-propargyloxyphenylalanine aminoacyl-tRNA synthetase derived from M. jannaschii tyrosyl tRNA-synthetase

<400> SEQUENCE: 19

```
atggacgaat ttgaaatgat aaagagaaac acatctgaaa ttatcagcga ggaagagtta     60

agagaggttt taaaaaaaga tgaaaaatct gctgctatag gttttgaacc aagtggtaaa    120

atacatttag ggcattatct ccaaataaaa aagatgattg atttacaaaa tgctggattt    180
```

-continued

```
gatataatta tattgttggc tgatttacac gcctatttaa accagaaagg agagttggat    240

gagattagaa aaataggaga ttataacaaa aaagtttttg aagcaatggg gttaaaggca    300

aaatatgttt atggaagtcc tttccagctt gataaggatt atacactgaa tgtctataga    360

ttggctttaa aaactacctt aaaaagagca agaaggagta tggaacttat agcaagagag    420

gatgaaaatc caaaggttgc tgaagttatc tatccaataa tgcaggttaa ttctctgcat    480

tatcatggcg ttgatgttgc agttggaggg atggagcaga gaaaaataca catgttagca    540

agggagcttt taccaaaaaa ggttgtttgt attcacaacc ctgtcttaac gggtttggat    600

ggagaaggaa agatgagttc ttcaaaaggg aattttatag ctgttgatga ctctccagaa    660

gagattaggg ctaagataaa gaaagcatac tgcccagctg gagttgttga aggaaatcca    720

ataatggaga tagctaaata cttccttgaa tatcctttaa ccataaaaag gccagaaaaa    780

tttggtggag atttgacagt taatagctat gaggagttag agagtttatt taaaaataag    840

gaattgcatc caatggattt aaaaaatgct gtagctgaag aacttataaa gattttagag    900

ccaattagaa agagatta                                                  918


<210> SEQ ID NO 20
<211> LENGTH: 14
<212> TYPE: PRT
<213> ORGANISM: Artificial
<220> FEATURE:
<223> OTHER INFORMATION: tryptic peptide of mutant myoglobin
<220> FEATURE:
<221> NAME/KEY: MISC_FEATURE
<222> LOCATION: (11)..(11)
<223> OTHER INFORMATION: X is para-propargyloxyphenylalanine

<400> SEQUENCE: 20

His Gly Val Thr Val Leu Thr Ala Leu Gly Xaa Ile Leu Lys
1               5                   10


<210> SEQ ID NO 21
<211> LENGTH: 306
<212> TYPE: PRT
<213> ORGANISM: Artificial
<220> FEATURE:
<223> OTHER INFORMATION: consensus para-propargyloxyphenylalanine
      aminoacyl-tRNA synthetase
<220> FEATURE:
<221> NAME/KEY: MISC_FEATURE
<222> LOCATION: (107)..(107)
<223> OTHER INFORMATION: X is Pro or Gln
<220> FEATURE:
<221> NAME/KEY: MISC_FEATURE
<222> LOCATION: (162)..(162)
<223> OTHER INFORMATION: X is Ala or Pro

<400> SEQUENCE: 21

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95
```

-continued

```
Gly Leu Lys Ala Lys Tyr Val Tyr Gly Ser Xaa Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile His
145                 150                 155                 160

Tyr Xaa Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 22
<211> LENGTH: 306
<212> TYPE: PRT
<213> ORGANISM: Artificial
<220> FEATURE:
<223> OTHER INFORMATION: rationally designed
      para-propargyloxyphenylalanine aminoacyl-tRNA synthetase

<400> SEQUENCE: 22

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140
```

-continued

```
Lys Val Ala Glu Val Ile Tyr Pro Ile Met Gln Val Asn Ala Ile His
145                 150                 155                 160

Tyr Ala Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 23
<211> LENGTH: 306
<212> TYPE: PRT
<213> ORGANISM: Artificial
<220> FEATURE:
<223> OTHER INFORMATION: rationally designed
      para-propargyloxyphenylalanine aminoacyl-tRNA synthetase

<400> SEQUENCE: 23

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile His
145                 150                 155                 160

Tyr Pro Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190
```

-continued

```
Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 24
<211> LENGTH: 306
<212> TYPE: PRT
<213> ORGANISM: Artificial
<220> FEATURE:
<223> OTHER INFORMATION: rationally designed
      para-propargyloxyphenylalanine aminoacyl-tRNA synthetase

<400> SEQUENCE: 24

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Gln Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile His
145                 150                 155                 160

Tyr Ala Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240
```

-continued

```
Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 25
<211> LENGTH: 306
<212> TYPE: PRT
<213> ORGANISM: Artificial
<220> FEATURE:
<223> OTHER INFORMATION: rationally designed
      para-propargyloxyphenylalanine aminoacyl-tRNA synthetase

<400> SEQUENCE: 25

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Gln Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile His
145                 150                 155                 160

Tyr Pro Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285
```

-continued

```
Asn Ala Val Ala Glu Glu Leu Ile Lys Ile Leu Glu Pro Ile Arg Lys
    290                 295                 300

Arg Leu
305
```

IN VIVO INCORPORATION OF ALKYNYL AMINO ACIDS INTO PROTEINS IN EUBACTERIA

CROSS-REFERENCE TO RELATED APPLICATIONS

This application is a national phase entry in the United States under 35 U.S.C. §371 from International Application Number PCT/US2005/033784, which has an international filing date of Sept. 20, 2005, and which designated the United States of America, which claims priority to and benefit of U.S. Provisional Patent Application Ser. No. 60/612,220, filed Sept. 21, 2004; U.S. Provisional Patent Application Ser. No. 60/630,876, filed Nov. 24, 2004; and U.S. Provisional Patent Application Ser. No. 60/634,151, filed Dec. 7, 2004, the disclosures of which are each incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with government support under Grant No. GM62159 from the National Institutes of Health. The government may have certain rights to this invention.

FIELD OF THE INVENTION

The invention is in the field of translation biochemistry. The invention relates to compositions and methods for making and using orthogonal tRNAs, orthogonal aminoacyl-tRNA synthetases, and pairs thereof, that incorporate alkynyl amino acids into proteins. The invention also relates to methods of producing proteins in cells using such pairs and related compositions.

BACKGROUND OF THE INVENTION

The ability to site-specifically, chemically modify proteins with nonpeptidic molecules such as spectroscopic probes, catalytic auxilaries, or polymers, or covalently cross-link a protein to another protein or to any other moiety, provides a powerful means to both investigate and manipulate the chemical and biological properties of proteins. A common approach involves the bioconjugation of nucleophilic surface residues on the protein, e.g., the side chains of lysine, histidine, or cysteine, with electrophilic groups on an exogenous molecule, such as aldehydes, α-halo carboxamides, and N-hydroxy succinimides (Lemineux, G. A.; Bertozzi, C. R. *TIBTECH* 1996, 16, 506).

Unfortunately, a challenge in using the naturally occurring nucleophilic targets in a protein to target modifications is the modest selectivity of these reactions and the multiple occurrences of nucleophilic amino acids in proteins, leading to the formation of heterogeneous mixtures of labeled proteins. Furthermore, the nucleophile-targeted modification reactions frequently require non-physiological conditions, which can preclude in vivo modification strategies and/or result in a loss of protein biological activity.

There is a need in the art to create new targets and novel strategies for specific and targeted protein modifications. Unfortunately, every known organism, from bacteria to humans, encodes the same twenty common amino acids (with the rare exceptions of selenocysteine (see, e.g., A. Bock et al., (1991), *Molecular Microbiology* 5:515-20) and pyrrolysine (see, e.g., G. Srinivasan, et al., (2002), *Science* 296:1459-62).

This feature limits the use of naturally occurring amino acids in the development of novel chemistries for targeted protein modification.

One strategy to overcome this limitation is to expand the genetic code and add amino acids that have distinguishing chemical properties to the biological repertoire. This approach has proven feasible by the use of "orthogonal" tRNA's and corresponding novel "orthogonal" aminoacyl-tRNA synthetases to add unnatural amino acids to proteins using the in vivo protein biosynthetic machinery of the eubacteria *Escherichia coli* (*E. coli*) and other organisms (e.g., Wang et al., (2001), *Science* 292:498-500; Chin et al., (2002) *Journal of the American Chemical Society* 124:9026-9027; Chin and Schultz, (2002), *ChemBioChem* 11:1135-1137; Chin, et al., (2002), *PNAS United States of America* 99:11020-11024; and Wang and Schultz, (2002), *Chem. Comm.,* 1-10). See also, International Publications WO 2002/086075, entitled "METHODS AND COMPOSITIONS FOR THE PRODUCTION OF ORTHOGONAL tRNA AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO 2005/007870, filed Jul. 7, 2004; and WO 2005/007624, filed Jul. 7, 2004.

There is a need in the art for novel methods to accomplish highly specific and targeted protein modifications. There is a need in the art for the development of orthogonal translation components that incorporate unnatural amino acids in vivo into proteins in *E. coli*, where the unnatural amino acids can be incorporated in a defined position, and where the unnatural amino acid has distinguishing chemical properties that allow it serve as a target for specific modification to the exclusion of cross reactions or side reactions with other parts of the proteins. This need in the art is especially applicable to *E. coli*, as eubacterial protein expression systems can produce large quantities of recombinant protein material for scientific study or therapeutic applications. This invention fulfills these and other needs, as will be apparent upon review of the following disclosure.

SUMMARY OF THE INVENTION

The invention provides compositions and methods for producing orthogonal components for incorporating alkynyl amino acids into a growing polypeptide chain in response to a selector codon, e.g., an amber stop codon, a four or more base codon, etc., in vivo or in vitro. The invention provides orthogonal-tRNAs (O-tRNAs), orthogonal aminoacyl-tRNA synthetases (O-RSs) and pairs thereof. These pairs can be used in a cellular or acellular system to incorporate alkynyl amino acids into growing polypeptide chains. Polypeptides that comprise alkynyl amino acids find particular use in conjugation reactions, where the alkyne moiety readily and specifically reacts with azido moieties in a [3+2]cycloaddition reaction to form a triazole linkage. Since the alkyne group is alien to in vivo systems, and an azido group can be added to essentially any chemical compound, systems for the site specific incorporation of alkynyl amino acids are a valuable tool for site-specific modification, as demonstrated herein.

In one aspect, a eubacterial cell contains the orthogonal aminoacyl-tRNA synthetase (O-RS), where that O-RS preferentially aminoacylates an orthogonal tRNA (O-tRNA) with an unnatural amino acid that is an alkynyl amino acid. In some embodiments, the eubacterial cell is an *E. coli* cell. In some aspects, the O-RS is derived from a *Methanococcus jannaschii* aminoacyl-tRNA synthetase, e.g., a *Methanococcus*

*jannaschii* tyrosyl-tRNA synthetase. In some embodiments, the tyrosyl-tRNA synthetase used to derive the O-RS is the wild-type *Methanococcus jannaschii* tyrosyl-tRNA synthetase having the amino acid sequence of SEQ ID NO: 2.

In some embodiments, the O-RS derived from the wild-type *Methanococcus jannaschii* tyrosyl-tRNA synthetase of SEQ ID NO: 2 comprises mutations at combinations of consensus positions, for example:

(a) alanine at amino acid position 32;
(b) proline or glutamine at amino acid position 107;
(c) alanine at amino acid position 158; and
(d) alanine or proline at amino acid position 162.

In some embodiments, the amino acid sequence of the O-RS comprises one of the sequences SEQ ID NO: 4, 6, 8, 10, 12, 14, 16, 18, or any conservative variant thereof. The cell containing the O-RS will typically comprise a nucleic acid that encodes the O-RS, for example, any of the O-RS species indicated above. The nucleic acid encoding the O-RS can comprise, for example, the nucleotide sequences of SEQ ID NO: 5, 7, 9, 11, 13, 15, 17 or 19.

In some embodiments, the O-tRNA used in the cell is an amber suppressor tRNA. For example, the O-tRNA is or comprises the polynucleotide sequence of SEQ ID NO: 1.

In some embodiments, the alkynyl amino acid that is a substrate for the O-RS is para-propargyloxyphenylalanine (pPRO-Phe). The cellular system also includes a nucleic acid having at least one selector codon, where the selector codon is recognized by the O-tRNA. The cell comprising the orthogonal components can further comprise the alkynyl amino acid, e.g., pPRO-Phe.

In some embodiments, the cell comprises a second orthogonal pair (i.e., a second O-tRNA and a second O-RS), where the second pair is specific for an unnatural amino acid that is different from the first unnatural amino acid, and where the second O-tRNA recognizes a selector codon that is different from the selector codon recognized by the first O-tRNA.

In some aspects, the cell comprising the orthogonal components comprises a translation system, where, in addition to the O-RS and O-tRNA, the system can comprise a nucleic acid with at least one selector codon encoding a polypeptide of interest, wherein the selector codon is recognized by the O-tRNA; and an alkynyl amino acid, where the O-RS is capable of charging the O-tRNA with the alkynyl amino acid.

In some aspects, the invention provides polypeptides, e.g., O-RS polypeptides as taught herein. These polypeptides can be derived from the *Methanococcus jannaschii* tyrosyl aminoacyl-tRNA synthetase of SEQ ID NO: 2, and have the amino acid consensus:

(a) alanine at amino acid position 32;
(b) proline or glutamine at amino acid position 107;
(c) alanine at amino acid position 158; and
(d) alanine or proline at amino acid position 162, and where the polypeptide has aminoacyl-tRNA synthetase activity capable of preferentially aminoacylating an orthogonal tRNA (O-tRNA) with an alkynyl amino acid. In some embodiments, a polypeptide of the invention is selected from SEQ ID NO: 4, 6, 8, 10, 12, 14, 16, 18, or a conservative variant thereof. Any such O-RS polypeptide of the invention is an aminoacyl-tRNA synthetase capable of preferentially aminoacylating an orthogonal tRNA (O-tRNA) in a eubacterial cell with an alkynyl amino acid. The invention also provides polynucleotides encoding any O-RS polypeptide of the invention as described above.

In some embodiments, a polynucleotide of the invention (encoding an O-RS of the invention) is selected from SEQ ID NOS: 5, 7, 9, 11, 13, 15, 17 and 19. Any polynucleotide of the invention encoding an O-RS of the invention can be incorporated into a vector, e.g., an expression vector. A vector of the invention can be used in a cell.

In some aspects, the invention provides methods for producing a protein comprising an unnatural alkynyl amino acid in a eubacterial cell. The methods can program the insertion of the alkynyl amino acid at any desired specified position in the protein. The methods have the steps:

(a) providing a eubacterial cell comprising:

(i) an orthogonal aminoacyl-tRNA synthetase (O-RS);

(ii) an orthogonal tRNA (O-tRNA), where the O-RS preferentially aminoacylates the O-tRNA with the alkynyl amino acid;

(iii) a nucleic acid encoding the protein, where the nucleic acid comprises at least one selector codon that is recognized by the O-tRNA; and, (iv) an alkynyl amino acid; and, (b) growing the cell;

(c) incorporating the alkynyl amino acid at the specified position in the protein encoded by the nucleic acid during translation of the protein, where the specified position in the protein corresponds to the position of the selector codon in the nucleic acid, thereby producing the protein comprising the alkynyl amino acid at the specified position. These methods typically use *E. coli* cells.

The O-RS used in these methods is typically derived from a *Methanococcus jannaschii* aminoacyl-tRNA synthetase, e.g., from a *Methanococcus jannaschii* tyrosyl-tRNA synthetase. In some embodiments, the *Methanococcus jannaschii* tyrosyl-tRNA synthetase is the synthetase of SEQ ID NO: 2. In some embodiments, the O-RS is derived from the *Methanococcus jannaschii* tyrosyl-tRNA synthetase of SEQ ID NO: 2, where the O-RS has an amino acid sequence having the following mutations:

(a) alanine at amino acid position 32;

(b) proline or glutamine at amino acid position 107;

(c) alanine at amino acid position 158; and (d) alanine or proline at amino acid position 162.

In some embodiments, the methods use an O-RS having an amino acid sequence selected from SEQ ID NO: 4, 6, 8, 10, 12, 14, 16, 18, or any conservative variants thereof. In the methods of the invention, the cell can contain a polynucleotide encoding any of these O-RS polypeptides. For example, a polynucleotide comprising the nucleotide sequences of SEQ ID NO: 5, 7, 9, 11, 13, 15, 17 or 19 can be used.

In some embodiments of these methods, the O-tRNA is an amber suppressor tRNA and the selector codon is an amber stop codon (TAG). In some embodiments, the O-tRNA comprises or is encoded by a polynucleotide sequence set forth in SEQ ID NO: 1. These methods can be used to produce a protein having the alkynyl amino acid para-propargyloxyphenylalanine (pPRO-Phe). The proteins produced by the methods of the invention can comprises an amino acid sequence that is at least 75% identical to the amino acid sequence of a wild-type therapeutic protein, a diagnostic protein, an industrial enzyme, or a portion thereof. These proteins can optionally be in association with a pharmaceutically acceptable carrier.

In some embodiments, the proteins produced by the methods of the invention can be modified at the position of the alkynyl amino acid, for example, by a [3+2]cycloaddition reaction to form a triazole linkage.

DEFINITIONS

Before describing the invention in detail, it is to be understood that this invention is not limited to particular biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes combinations of two or more cells; reference to "a polynucleotide" includes, as a practical matter, many copies of that polynucleotide.

Unless defined herein and below in the reminder of the specification, all technical and scientific terms used herein have the same meaning as commonly understood by one of ordinary skill in the art to which the invention pertains.

Orthogonal: As used herein, the term "orthogonal" refers to a molecule (e.g., an orthogonal tRNA (O-tRNA) and/or an orthogonal aminoacyl-tRNA synthetase (O-RS)) that functions with endogenous components of a cell with reduced efficiency as compared to a corresponding molecule that is endogenous to the cell or translation system, or that fails to function with endogenous components of the cell. In the context of tRNAs and aminoacyl-tRNA synthetases, orthogonal refers to an inability or reduced efficiency, e.g., less than 20% efficiency, less than 10% efficiency, less than 5% efficiency, or less than 1% efficiency, of an orthogonal tRNA to function with an endogenous tRNA synthetase compared to an endogenous tRNA to function with the endogenous tRNA synthetase, or of an orthogonal aminoacyl-tRNA synthetase to function with an endogenous tRNA compared to an endogenous tRNA synthetase to function with the endogenous tRNA. The orthogonal molecule lacks a functionally normal endogenous complementary molecule in the cell. For example, an orthogonal tRNA in a cell is aminoacylated by any endogenous RS of the cell with reduced or even zero efficiency, when compared to aminoacylation of an endogenous tRNA by the endogenous RS. In another example, an orthogonal RS aminoacylates any endogenous tRNA a cell of interest with reduced or even zero efficiency, as compared to aminoacylation of the endogenous tRNA by an endogenous RS. A second orthogonal molecule can be introduced into the cell that functions with the first orthogonal molecule. For example, an orthogonal tRNA/RS pair includes introduced complementary components that function together in the cell with an efficiency (e.g., 45% efficiency, 50% efficiency, 60% efficiency, 70% efficiency, 75% efficiency, 80% efficiency, 90% efficiency, 95% efficiency, or 99% or more efficiency) as compared to that of a control, e.g., a corresponding tRNA/RS endogenous pair, or an active orthogonal pair (e.g., a tyrosyl orthogonal tRNA/RS pair).

Orthogonal tyrosyl-tRNA: As used herein, an orthogonal tyrosyl-tRNA (tyrosyl-O-tRNA) is a tRNA that is orthogonal to a translation system of interest, where the tRNA is: (1) identical or substantially similar to a naturally occurring tyrosyl-tRNA, (2) derived from a naturally occurring tyrosyl-tRNA by natural or artificial mutagenesis, (3) derived by any process that takes a sequence of a wild-type or mutant tyrosyl-tRNA sequence of (1) or (2) into account, (4) homologous to a wild-type or mutant tyrosyl-tRNA; (5) homologous to any example tRNA that is designated as a substrate for a tyrosyl-tRNA synthetase in TABLE 4, or (6) a conservative variant of any example tRNA that is designated as a substrate for a tyrosyl-tRNA synthetase in TABLE 4. The tyrosyl-tRNA can exist charged with an amino acid, or in an uncharged state. It is also to be understood that a "tyrosyl-O-tRNA" optionally is charged (aminoacylated) by a cognate synthetase with an amino acid other than tyrosine, e.g., with the unnatural amino acid para-propargyloxyphenylalanine. Indeed, it will be appreciated that a tyrosyl-O-tRNA of the invention is advantageously used to insert essentially any amino acid, whether natural or artificial, into a growing polypeptide, during translation, in response to a selector codon.

Orthogonal tyrosyl amino acid synthetase: As used herein, an orthogonal tyrosyl amino acid synthetase (tyrosyl-O-RS) is an enzyme that preferentially aminoacylates the tyrosyl-O-tRNA with an amino acid in a translation system of interest. The amino acid that the tyrosyl-O-RS loads onto the tyrosyl-O-tRNA can be any amino acid, whether natural, unnatural or artificial, and is not limited herein. The synthetase is optionally the same as or homologous to a naturally occurring tyrosyl amino acid synthetase, or the same as or homologous to a synthetase designated as an O-RS in TABLE 4. For example, the O-RS can be a conservative variant of a tyrosyl-O-RS of TABLE 4, and/or can be at least 50%, 60%, 70%, 80%, 90%, 95%, 98%, 99% or more identical in sequence to an O-RS of TABLE 4.

Cognate: The term "cognate" refers to components that function together, e.g., an orthogonal tRNA and an orthogonal aminoacyl-tRNA synthetase. The components can also be referred to as being complementary.

Preferentially aminoacylates: As used herein in reference to orthogonal translation systems, an O-RS "preferentially aminoacylates" a cognate O-tRNA when the O-RS charges the O-tRNA with an amino acid more efficiently than it charges any endogenous tRNA in an expression system. That is, when the O-tRNA and any given endogenous tRNA are present in a translation system in approximately equal molar ratios, the O-RS will charge the O-tRNA more frequently than it will charge the endogenous tRNA. Preferably, the relative ratio of O-tRNA charged by the O-RS to endogenous tRNA charged by the O-RS is high, preferably resulting in the O-RS charging the O-tRNA exclusively, or nearly exclusively, when the O-tRNA and endogenous tRNA are present in equal molar concentrations in the translation system. The relative ratio between O-tRNA and endogenous tRNA that is charged by the O-RS, when the O-tRNA and O-RS are present at equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

The O-RS "preferentially aminoacylates an O-tRNA with an unnatural amino acid" when (a) the O-RS preferentially aminoacylates the O-tRNA compared to an endogenous tRNA, and (b) where that aminoacylation is specific for the unnatural amino acid, as compared to aminoacylation of the O-tRNA by the O-RS with any natural amino acid. That is, when the unnatural and natural amino acids are present in equal molar amounts in a translation system comprising the O-RS and O-tRNA, the O-RS will load the O-tRNA with the unnatural amino acid more frequently than with the natural amino acid. Preferably, the relative ratio of O-tRNA charged with the unnatural amino acid to O-tRNA charged with the natural amino acid is high. More preferably, O-RS charges the O-tRNA exclusively, or nearly exclusively, with the unnatural amino acid. The relative ratio between charging of the O-tRNA with the unnatural amino acid and charging of the O-tRNA with the natural amino acid, when both the natural and unnatural amino acids are present in the translation system in equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

Selector codon: The term “selector codon” refers to codons recognized by the O-tRNA in the translation process and not recognized by an endogenous tRNA. The O-tRNA anticodon loop recognizes the selector codon on the mRNA and incorporates its amino acid, e.g., an unnatural amino acid, such as an alkynyl amino acid, at this site in the polypeptide. Selector codons can include, e.g., nonsense codons, such as, stop codons, e.g., amber, ochre, and opal codons; four or more base codons; rare codons; codons derived from natural or unnatural base pairs and/or the like.

Suppressor tRNA: A suppressor tRNA is a tRNA that alters the reading of a messenger RNA (mRNA) in a given translation system, e.g., by providing a mechanism for incorporating an amino acid into a polypeptide chain in response to a selector codon. For example, a suppressor tRNA can read through, e.g., a stop codon (e.g., an amber, ocher or opal codon), a four base codon, a rare codon, etc.

Suppression activity: As used herein, the term “suppression activity” refers, in general, to the ability of a tRNA (e.g., a suppressor tRNA) to allow translational read-through of a codon (e.g. a selector codon that is an amber codon or a 4-or-more base codon) that would otherwise result in the termination of translation or mistranslation (e.g., frame-shifting). Suppression activity of a suppressor tRNA can be expressed as a percentage of translational read-through activity observed compared to a second suppressor tRNA, or as compared to a control system, e.g., a control system lacking an O-RS.

The present invention provides various means by which suppression activity can be quantitated. Percent suppression of a particular O-tRNA and O-RS against a selector codon (e.g., an amber codon) of interest refers to the percentage of activity of a given expressed test marker (e.g., LacZ), that includes a selector codon, in a nucleic acid encoding the expressed test marker, in a translation system of interest, where the translation system of interest includes an O-RS and an O-tRNA, as compared to a positive control construct, where the positive control lacks the O-tRNA, the O-RS and the selector codon. Thus, for example, if an active positive control marker construct that lacks a selector codon has an observed activity of X in a given translation system, in units relevant to the marker assay at issue, then percent suppression of a test construct comprising the selector codon is the percentage of X that the test marker construct displays under essentially the same environmental conditions as the positive control marker was expressed under, except that the test marker construct is expressed in a translation system that also includes the O-tRNA and the O-RS. Typically, the translation system expressing the test marker also includes an amino acid that is recognized by the O-RS and O-tRNA. Optionally, the percent suppression measurement can be refined by comparison of the test marker to a “background” or “negative” control marker construct, which includes the same selector codon as the test marker, but in a system that does not include the O-tRNA, O-RS and/or relevant amino acid recognized by the O-tRNA and/or O-RS. This negative control is useful in normalizing percent suppression measurements to account for background signal effects from the marker in the translation system of interest.

Suppression efficiency can be determined by any of a number of assays known in the art. For example, a β-galactosidase reporter assay can be used, e.g., a derivatived lacZ plasmid (where the construct has a selector codon n the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatized lacZ construct, where the construct has a corresponding sense codon at desired position rather than a selector codon.

Translation system: The term “translation system” refers to the components that incorporate an amino acid into a growing polypeptide chain (protein). Components of a translation system can include, e.g., ribosomes, tRNAs, synthetases, mRNA and the like. The O-tRNA and/or the O-RSs of the invention can be added to or be part of an in vitro or in vivo translation system, e.g., in a non-eukaryotic cell, e.g., a bacterium (such as *E. coli*), or in a eukaryotic cell, e.g., a yeast cell, a mammalian cell, a plant cell, an algae cell, a fungus cell, an insect cell, and/or the like.

Unnatural amino acid: As used herein, the term “unnatural amino acid” refers to any amino acid, modified amino acid, and/or amino acid analogue, such as an alkynyl amino acid, that is not one of the 20 common naturally occurring amino acids or seleno cysteine or pyrrolysine.

Derived from: As used herein, the term “derived from” refers to a component that is isolated from or made using a specified molecule or organism, or information from the specified molecule or organism. For example, a polypeptide that is derived from a second polypeptide comprises an amino acid sequence that is identical or substantially similar to the amino acid sequence of the second polypeptide. In the case of polypeptides, the derived species can be obtained by, for example, naturally occurring mutagenesis, artificial directed mutagenesis or artificial random mutagenesis. The mutagenesis used to derive polypeptides can be intentionally directed or intentionally random. The mutagenesis of a polypepitde to create a different polypeptide derived from the first can be a random event (e.g., caused by polymerase infidelity) and the identification of the derived polypeptide can be serendipitous. Mutagenesis of a polypeptide typically entails manipulation of the polynucleotide that encodes the polypeptide.

Positive selection or screening marker: As used herein, the term “positive selection or screening marker” refers to a marker that when present, e.g., expressed, activated or the like, results in identification of a cell, which comprise the trait, e.g., cells with the positive selection marker, from those without the trait.

Negative selection or screening marker: As used herein, the term “negative selection or screening marker” refers to a marker that, when present, e.g., expressed, activated, or the like, allows identification of a cell that does not comprise a selected property or trait (e.g., as compared to a cell that does possess the property or trait).

Reporter: As used herein, the term “reporter” refers to a component that can be used to identify and/or select target components of a system of interest. For example, a reporter can include a protein, e.g., an enzyme, that confers antibiotic resistance or sensitivity (e.g., β-lactamase, chloramphenicol acetyltransferase (CAT), and the like), a fluorescent screening marker (e.g., green fluorescent protein (e.g., (GFP), YFP, EGFP, RFP, etc.), a luminescent marker (e.g., a firefly luciferase protein), an affinity based screening marker, or positive or negative selectable marker genes such as lacZ, β-gal/lacZ (β-galactosidase), ADH (alcohol dehydrogenase), his3, ura3, leu2, lys2, or the like.

Eukaryote: As used herein, the term "eukaryote" refers to organisms belonging to the Kingdom Eucarya. Eukaryotes are generally distinguishable from prokaryotes by their typically multicellular organization (but not exclusively multicellular, for example, yeast), the presence or a membrane-bound nucleus and other membrane-bound organelles, linear genetic material (i.e., linear chromosomes), the absence of operons, the presence of introns, message capping and poly-A mRNA, and other biochemical characteristics, such as a distinguishing ribosomal structure. Eukaryotic organisms include, for example, animals (e.g., mammals, insects, reptiles, birds, etc.), ciliates, plants (e.g., monocots, dicots, algae, etc.), fungi, yeasts, flagellates, microsporidia, protists, etc.

Prokaryote: As used herein, the term "prokaryote" refers to organisms belonging to the Kingdom Monera (also termed Procarya). Prokaryotic organisms are generally distinguishable from eukaryotes by their unicellular organization, asexual reproduction by budding or fission, the lack of a membrane-bound nucleus or other membrane-bound organelles, a circular chromosome, the presence of operons, the absence of introns, message capping and poly-A mRNA, and other biochemical characteristics, such as a distinguishing ribosomal structure. The Prokarya include subkingdoms Eubacteria and Archaea (sometimes termed "Archaebacteria"). Cyanobacteria (the blue green algae) and mycoplasma are sometimes given separate classifications under the Kingdom Monera.

Bacteria: As used herein, the terms "bacteria" and "eubacteria" refer to prokaryotic organisms that are distinguishable from Archaea. Similarly, Archaea refers to prokaryotes that are distinguishable from eubacteria. Eubacteria and Archaea can be distinguished by a number morphological and biochemical criteria. For example, differences in ribosomal RNA sequences, RNA polymerase structure, the presence or absence of introns, antibiotic sensitivity, the presence or absence of cell wall peptidoglycans adn other cell wall components, the branched versus unbranched structures of membrane lipids, and the presence/absence of histones and histone-like proteins are used to assign an organism to Eubacteria or Archaea.

Examples of Eubacteria include *Escherichia coli, Thermus thermophilus* and *Bacillus stearothermophilus*. Example of Archaea include *Methanococcus jannaschii* (Mj), *Methanosarcina mazei* (Mm), *Methanobacterium thermoautotrophicum* (Mt), *Methanococcus maripaludis, Methanopyrus kandleri, Halobacterium* such as *Haloferax volcanii* and *Halobacterium* species NRC-1, *Archaeoglobus fulgidus* (Af), *Pyrococcus furiosus* (Pf), *Pyrococcus horikoshii* (Ph), *Pyrobaculum aerophilum, Pyrococcus abyssi, Sulfolobus solfataricus* (Ss), *Sulfolobus tokodaii, Aeuropyrum pernix* (Ap), *Thermoplasma acidophilum* and *Thermoplasma volcaniium*.

Conservative variant: As used herein, the term "conservative variant," in the context of a translation component, refers to a translation component, e.g., a conservative variant O-tRNA or a conservative variant O-RS, that functionally performs similar to a base component that the conservative variant is similar to, e.g., an O-tRNA or O-RS, having variations in the sequence as compared to a reference O-tRNA or O-RS. For example, an O-RS will aminoacylate a complementary O-tRNA or a conservative variant O-tRNA with an unnatural amino acid, e.g., an alkynyl amino acid such as para-propargyloxyphenylalanine, although the O-tRNA and the conservative variant O-tRNA do not have the same sequence. The conservative variant can have, e.g., one variation, two variations, three variations, four variations, or five or more variations in sequence, as long as the conservative variant is complementary to the corresponding O-tRNA or O-RS.

Selection or screening agent: As used herein, the term "selection or screening agent" refers to an agent that, when present, allows for selection/screening of certain components from a population. For example, a selection or screening agent can be, but is not limited to, e.g., a nutrient, an antibiotic, a wavelength of light, an antibody, an expressed polynucleotide, or the like. The selection agent can be varied, e.g., by concentration, intensity, etc.

In response to: As used herein, the term "in response to" refers to the process in which a O-tRNA of the invention recognizes a selector codon and mediates the incorporation the alkynyl amino acid, which is coupled to the tRNA, into the growing polypeptide chain.

Encode: As used herein, the term "encode" refers to any process whereby the information in a polymeric macromolecule or sequence string is used to direct the production of a second molecule or sequence string that is different from the first molecule or sequence string. As used herein, the term is used broadly, and can have a variety of applications. In one aspect, the term "encode" describes the process of semi-conservative DNA replication, where one strand of a double-stranded DNA molecule is used as a template to encode a newly synthesized complementary sister strand by a DNA-dependent DNA polymerase.

In another aspect, the term "encode" refers to any process whereby the information in one molecule is used to direct the production of a second molecule that has a different chemical nature from the first molecule. For example, a DNA molecule can encode an RNA molecule (e.g., by the process of transcription incorporating a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

Alkyne: As used herein, the term "alkyne" (also sometimes referred to as "acetylene") refers to chemical structures containing a triple bond between two carbon atoms (as shown in FIG. 1B), having the general structure:

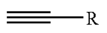

where R is any atom or structure. When used as a substituent, the alkyne moiety is termed an "alkynyl" group. The alkynyl carbon atoms are $sp^2$ hybridized and form only bonds to two other atoms; one of these bonds will be a single bond while the second bond is a triple bond. For example, an alkynyl amino acid is an amino acid containing a triple bond between two carbon centers. Because alkynyl substituents do not appear on amino acids in nature, any alkynyl amino acid is an unnatural amino acid.

Azido: As used herein, the term "azido" refers to the chemical group —$N_3$, having the general structure:

$$R—N{=}N^{+}{=}N^{-}$$

The azido group is typically attached to a carbon atom.

For example, an azido dye is a dye molecule with an azido substituent group (see, e.g., the azido dyes 2 and 3, in FIGS.

6A and 6B). The term "azide" refers to a chemical compound containing the azido group (for example, benzyl azide, sodium azide, etc.).

BRIEF DESCRIPTION OF THE FIGURES

FIG. 2 provides the nucleotide and amino acid sequences of wild-type *Methanococcus jannaschii* tyrosyl-tRNA synthetase (MjTyrRS). The amino acid positions (and corresponding triplet codons) targeted in the directed mutagenesis or otherwise mutated in the para-propargyloxyphenylalanine (pPRO-Phe) tRNA synthetase are boxed.

FIG. 3 provides a table describing the eight (8) para-propargyloxyphenylalanine (pPRO-Phe) tRNA synthetase species identified and isolated following mutagenesis of a polynucleotide encoding the wild-type *Methanococcus jannaschii* tyrosyl-tRNA synthetase. The amino acids encoded by the indicated codons in the wild-type *Methanococcus jannaschii* tyrosyl-tRNA synthetase and the para-propargyloxyphenylalanine tRNA synthetases (pPRO-PheRS) are indicated. The codon at the mutant positions are also indicated. Amino acid position numbering of the mutants is according to the amino acid numbering of wild-type *Methanococcus jannaschii* tyrosyl-tRNA synthetase, as shown in FIG. 2.

FIGS. 8A and 8B provide the structures and names of examples of alkynyl unnatural amino acids. FIG. 8A provides alkynyl unnatural amino acids that can be chemically synthesized from non-natural precursors. FIG. 8B provides alkynyl unnatural amino acids that can be potentially synthesized from pre-existing naturally-occurring amino acid substrates.

DETAILED DESCRIPTION OF THE INVENTION

There is a considerable need for chemical reactions that modify proteins under physiological conditions in a highly selective fashion (Lemineux and Bertozzi (1996) *TIBTECH,* 16:506). Most reactions currently used in the art for the selective modification of proteins involve covalent bond formation between nucleophilic and electrophilic reaction partners that target naturally occurring nucleophilic residues in the protein amino acid side chains, e.g., the reaction of α-halo ketones with histidine or cysteine side chains. Selectivity in these cases is determined by the number and accessibility of the nucleophilic residues in the protein. Unfortunately, naturally occurring proteins frequently contain poorly positioned (e.g., inaccessible) reaction sites or multiple reaction targets (e.g., lysine, histidine and cysteine residues), resulting in poor selectivity in the modification reactions, making highly targeted protein modification by nucleophilic/electrophilic reagents difficult. Furthermore, the sites of modification are typically limited to the naturally occurring nucleophilic side chains of lysine, histidine or cysteine. Modification at other sites is difficult or impossible.

One solution to this problem is the programmed, site-specific biosynthetic incorporation of unnatural amino acids with novel reactivity into proteins using orthogonal translation components (Wang and Schultz (2002) *Chem. Commun.,* 1:1; and van Maarseveen and Back (2003) *Angew. Chem.,* 115:6106). We report herein a highly efficient novel method for the selective modification of proteins that involves the genetic incorporation of alkynyl-containing unnatural amino acids into proteins produced in bacteria (e.g., *E. coli*) in response to the amber nonsense codon, TAG. These alkynyl amino acid side chains can then be specifically and regioselectively modified. Because of the unique reaction chemistry of the alkynyl group, proteins can be modified with extremely high selectivity.

Figure 1A:
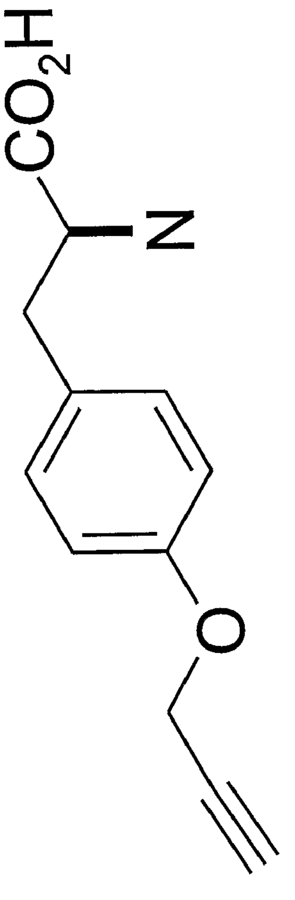
FIG. 1A provides the chemical structure (1) of the unnatural alkynyl amino acid para-propargyloxyphenylalanine (also known as 2-amino-3-[4-(prop-2-ynyloxy)phenyl]-propionic acid according to IUPAC nomenclature).

To selectively introduce the alkynyl functional group at unique sites (e.g., at a desired site) in proteins produced in a bacterial expression system, we have evolved orthogonal tRNA/aminoacyl-tRNA synthetase pairs that function in eubacteria that genetically encode the alkynyl amino acid para-propargyloxyphenylalanine (pPRO-Phe; see FIG. 1A). Briefly, we have identified novel mutants of the *Methanococcus janaschii* tyrosyl-tRNA synthetase that selectively charges an amber suppressor tRNA with para-propargyloxyphenylalanine (pPRO-Phe) in *Escherichia coli* cells. These evolved tRNA-synthetase pairs can be used to site-specifically incorporate an alkynyl group into a protein.

Targeted Protein Modification

We report herein a highly efficient method for the selective modification of proteins that involves the genetic incorporation of alkynyl-containing unnatural amino acids into proteins produced in eubacteria (e.g., *E. coli*) in response to the amber nonsense codon, TAG. The novel compositions and methods described herein employ an orthogonal tRNA/aminoacyl-tRNA synthetase system, where the orthogonal system uses components derived from *Methanococcus janaschii*, and where these components are used in a eubacterial host system for producing protein of interest. The incorporation of the alkynyl amino acid into the protein can be programmed to occur at any desired position by engineering the polynucleotide encoding the protein of interest to contain a selector codon that signals the incorporation of the alkynyl amino acid.

Figure 1B:
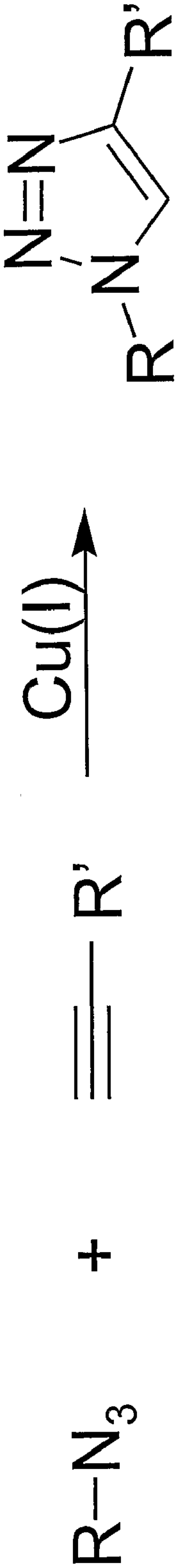
FIG. 1B provides the generalized reaction chemistry of the irreversible formation of triazoles by [3+2]cycloaddition reaction of an azido and an alkyne in the presence of copper at room temperature.

These alkynyl amino acid side chains on the protein of interest can then be specifically and regioselectively modified by a Huisgen [3+2]cycloaddition reaction with azido derivatives (see, FIG. 1B) (Padwa, In *Comprehensive Organic Synthesis*; [Trost, B. M., Ed.] Pergamon: Oxford, 1991, Vol. 4, p 1069-1109; Huisgen, In 1,3-*Dipolar Cycloaddition Chemistry*, [Padwa, A., Ed.] Wiley: New York, 1984; p 1-176). Because this method involves a cycloaddition rather than a nucleophilic substitution, proteins can be modified with extremely high selectivity. This reaction has the benefits that it can be carried out at room temperature under aqueous conditions with excellent regioselectivity (1,4>1,5) by the addition of catalytic amounts of Cu(I) salts to the reaction mixture (Tomoe et al., (2002) *J. Org. Chem.,* 67:3057-3064; Rostovtsev et al., (2002) *Angew. Chem., Int. Ed.,* 41:2596-2599).

An alkynyl reactive target has the advantages of being completely alien to in vivo systems, is highly selective in its reaction chemistries (e.g., highly reactive with azido-containing moieties), and can be conjugated using relatively mild reaction conditions that permit both in vitro and in vivo conjugation reactions involving proteins, and preserving protein biological activity. To demonstrate (but not limit) the present invention, the alkynyl moiety is incorporated into a myoglobin model protein, and the protein is then bioconjugated with azido fluorescent dyes (see, FIGS. 6A and 6B) by a [3+2]-cycloaddition reaction by formation of a stable triazole linkage (see, FIG. 1B).

Although the invention uses two azido fluorescent dyes to illustrate [3+2]cycloaddition between the alkynyl amino acid and azido moieties (see, EXAMPLE 4), it is not intended that the invention be limited to the use of these two azido dyes, or any dye or label, or indeed any single type of conjugateable material. An azido-containing moiety of the invention can be virtually any molecule that is an azido derivative. Such molecules include, but are not limited to, dyes, fluorophores, crosslinking agents, saccharide derivatives, polymers (e.g., derivatives of polyethylene glycol), photocrosslinkers, cytotoxic compounds, affinity labels, derivatives of biotin, resins, beads, a second protein or polypeptide (or more), polynucleotide(s) (e.g., DNA, RNA, etc.), metal chelators, cofactors, fatty acids, carbohydrates, and the like. These azido molecules can be conjugated to an unnatural amino acid with an alkynyl group, e.g., para-propargyloxyphenylalanine (see, FIG. 1A).

Figure 6A:
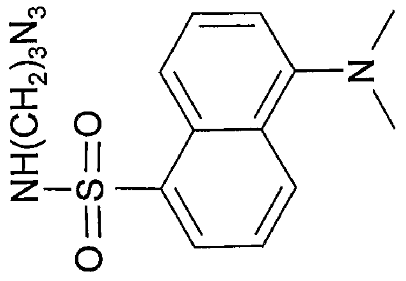
FIGS. 6A and 6B provide the chemical structures (2 and 3, respectively) of azido-functionalized dyes. Dye 2 in FIG. 6A contains a dansyl fluorophore, and dye 3 in FIG. 6B contains a fluoresceine fluorophore.
Figure 6B:
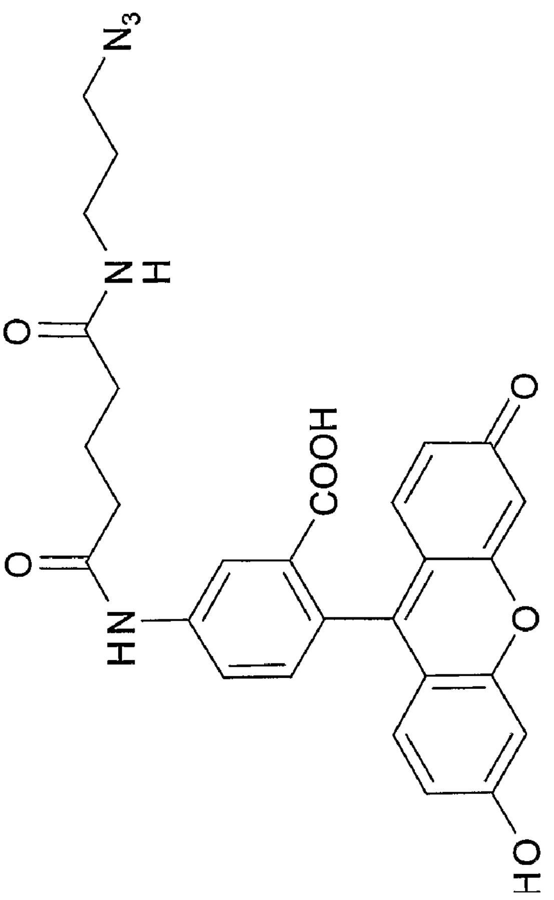

The invention provides detailed description for the synthesis of the azido dyes shown in FIGS. 6A and 6B. See, EXAMPLES 6 and 7, respectively. However, it is well within the means of one of skill in the art to synthesize an azido derivative of any particular molecule of interest. For example, many texts and protocols are available describing how to synthesize azido compounds. For a general reference see: Patai, Saul, "The chemistry of the azido group" in *The Chemistry of Functional Groups*, London, New York, Interscience Publishers, 1971.

In another aspect, the invention provides compositions and methods for the generation of PEGylated polypeptides by using azido derivatives of polyethylene glycol (azido-PEG) for use in conjugation reactions with alkynyl-containing polypeptides. The generalized structure of an azido polyethylene glycol is:

$$N_3—CH_2—(CH_2—O—CH_2)_n—CH_2OR$$

where R is H or $CH_3$, and where n is an integer between, e.g., 50 and 10,000, 75 and 5,000, 100 and 2,000, 100 and 1,000, etc. In various embodiments of the invention, the azido polyethylene glycol has a molecular weight of, e.g., about 5,000 to about 100,000 Da (i.e., about 5 kDa to about 100 kDa), about 20,000 to about 50,000 Da, about 20,000 to about 10,000 Da (e.g., 20,000 Da), etc. Techniques for the synthesis of an azido polyethylene glycol are well known to one of skill in the art. For example a polyethylene glycol molecule containing an electrophilic group (e.g., a bromide or an N-hydroxysuccinimide ester) can be reacted with a nucleophilic molecule containing an azido group (e.g., sodium azide or 3-azidopropylamine) to generate an azido polyethylene glycol.

Azido-PEG finds use with the invention when bioconjugated to an alkynyl-containing protein via a triazole linkage. Derivatization of protein-based therapeutics with polyethylene glycol (PEGylation) can often improve pharmacokinetic and pharmacodynamic properties of the proteins and thereby, improve efficacy and minimize dosing frequency. The various advantages of PEGylation of protein therapeutics are discussed and illustrated in, for example, Deiters et al., "Site-specific PEGylation of proteins containing unnatural amino acids," Bioorganic & Medicinal Chemistry Letters 14:5743-5745 (2004).

In addition, other advantages associated with the generation of polypeptides comprising unnatural alkynyl amino acids that also contain an ester linkage are contemplated. For example, a PEGylated polypeptide created by using an alkynyl amino acid with an ester linkage can allow the slow release of the polypeptide by saponification of the ester linkages in vivo or in vitro. Also, using a polymeric support (an azido resin) in place of a azido-PEG molecule enables a protein affinity purification. The triazole covalent linkage permits very strong washing steps, and the use of the ester alkynyl amino acid allows release of the protein by treatment with a base. Significantly, such an affinity purification scheme no longer requires the presence of an artificial tag (e.g., hexahistidine) or epitope on the protein of interest for the purification. Depending on the unnatural amino acid used, an essentially wild-type (native) polypeptide can be released from the affinity resin following the cleavage step.

Unnatural alkynyl amino acids with ester linkages can by synthesized and incorporated into proteins, for example, 3-[(prop-2-ynyloxy)carbonyl]-2-aminopropanoic acid and 4-[(prop-2-ynyloxy)carbonyl]-2-aminobutanoic acid (see, FIG. 8B). After bioconjugation via [3+2]cycloaddition, the ester linkages could be cleaved by saponification in vivo or in vitro; an application would be, e.g., the slow release of the peptide part from a PEGylated protein.

In some aspects, polypeptides of the invention include the alkynyl-containing polypeptides, and furthermore, include the conjugated forms of those polypeptides. For example, in some aspects, the invention includes a polypeptide comprising a triazole linkage and a covalently coupled fluorescent azido dye (e.g., see FIGS. 6A, 6B and 7A). In this aspect, the polypeptide formerly comprised an alkynyl group and the dye formerly comprised an azido group, and the two were conjugated via a [3+2]cycloaddition to form the triazole linkage. In another embodiment, a alkynyl-containing protein of the invention comprises an azido polyethylene glycol (see chemical structure 6).

Orthogonal tRNA/Aminoacyl-tRNA Synthetase Technology

An understanding of the novel compositions and methods of the present invention is facilitated by an understanding of the activities associated with orthogonal tRNA and orthogonal aminoacyl-tRNA synthetase pairs. Discussions of orthogonal tRNA and aminoacyl-tRNA synthetase technologies can be found, for example, in International Publications WO 2002/085923, WO 2002/086075, WO 204/09459, WO 2005/019415, WO 2005/007870 and WO 2005/007624.

In order to add additional reactive unnatural amino acids, such as alkynyl amino acids, to the genetic code, new orthogonal pairs comprising an aminoacyl-tRNA synthetase and a suitable tRNA are needed that can function efficiently in the host translational machinery, but that are "orthogonal" to the translation system at issue, meaning that it functions independently of the synthetases and tRNAs endogenous to the translation system. Desired characteristics of the orthologous pair include tRNA that decode or recognize only a specific codon, e.g., a selector codon, that is not decoded by any endogenous tRNA, and aminoacyl-tRNA synthetases that preferentially aminoacylate (or "charge") its cognate tRNA with only one specific unnatural amino acid. The O-tRNA is also not typically aminoacylated by endogenous synthetases. For example, in *E. coli*, an orthogonal pair will include an aminoacyl-tRNA synthetase that does not cross-react with any of the endogenous tRNA, e.g., which there are 40 in *E. coli*, and an orthogonal tRNA that is not aminoacylated by any of the endogenous synthetases, e.g., of which there are 21 in *E. coli.*

The invention described herein provides orthogonal pairs for the genetic encoding and incorporation of alkynyl amino acids into proteins in a eubacteria, e.g., *E. coli*, where the orthogonal components do not cross-react with endogenous *E. coli* components of the translational machinery of the host cell, but recognize the desired unnatural amino acid and incorporate it into proteins in response to the amber nonsense codon, TAG. The orthogonal components provided by the invention include orthogonal aminoacyl-tRNA synthetases derived from *Methanococcus jannaschii* tyrosyl tRNA-synthetase, and the mutant tyrosyl $tRNA_{CUA}$ amber suppressor. In this system, the mutant aminoacyl-tRNA synthetases aminoacylate the suppressor tRNA with pPRO-Phe and not with any of the common twenty amino acids.

This invention provides compositions of and methods for identifying and producing additional orthogonal tRNA-aminoacyl-tRNA synthetase pairs, e.g., O-tRNA/O-RS pairs that can be used to incorporate an alkynyl amino acid into a protein. An O-tRNA of the invention is capable of mediating incorporation of alkynyl amino acid into a protein that is encoded by a polynucleotide, which comprises a selector codon that is recognized by the O-tRNA, e.g., in vivo. The anticodon loop of the O-tRNA recognizes the selector codon on an mRNA and incorporates its amino acid, e.g., a alkynyl amino acid at this site in the polypeptide. An orthogonal aminoacyl-tRNA synthetase of the invention preferentially aminoacylates (or charges) its O-tRNA with only one specific alkynyl amino acid.

For example, as demonstrated herein, the alkynyl amino acid para-propargyloxyphenylalanine (pPRO-Phe; see FIG. 1A, structure 1), which can be targeted for modification in a highly selective manner, was incorporated selectively and efficiently into a protein in a eubacterial cell (*Escherichia coli; E. coli*) in response to a selector codon, e.g., the TAG codon. Once incorporated into a protein, pPRO-Phe can be chemically targeted within the cell, for example, can be targeted for modification with a dye carrying an azido group. The azido group on a dye molecule can react with the alkynyl amino acid and target the protein for dye labeling in a highly selective manner.

The ability to incorporate an alkynyl amino acid site-specifically into proteins can facilitate the study of proteins, as well as enable the engineering of proteins with novel properties. For example, expression of alkynyl-containing proteins can facilitate the study of proteins by specific labeling, alter catalytic function of enzymes, crosslink protein with other proteins, small molecules and biomolecules, etc.

Orthogonal tRNA/Orthogonal Aminoacyl-tRNA Synthetases and Pairs Thereof

Translation systems that are suitable for making proteins that include one or more unnatural amino acids are described in, for example, International Publication Numbers WO 2002/086075, entitled "METHODS AND COMPOSITION FOR THE PRODUCTION OF ORTHOGONAL tRNA-AMINOACYL-tRNA SYNTHETASE PAIRS;" WO 2002/085923, entitled "IN VIVO INCORPORATION OF UNNATURAL AMINO ACIDS;" and WO 2004/094593, entitled "EXPANDING THE EUKARYOTIC GENETIC CODE;" WO 2005/019415, filed Jul. 7, 2004; WO 2005/007870, filed Jul. 7, 2004 and WO 2005/007624, filed Jul. 7, 2004. Each of these applications is incorporated herein by reference in its entirety. Such translation systems generally comprise cells (which can be non-eukaryotic cells such as *E. coli*, or eukaryotic cells such as yeast) that include an orthogonal tRNA (O-tRNA), an orthogonal aminoacyl tRNA synthetase (O-RS), and an unnatural amino acid (e.g., in the present invention, an alkynyl amino acid), where the O-RS aminoacylates the O-tRNA with the alkynyl amino acid. An orthogonal pair of the invention includes an O-tRNA, e.g., a suppressor tRNA, a frameshift tRNA, or the like, and an O-RS. Individual components are also provided in the invention.

In general, when an orthogonal pair recognizes a selector codon and loads an amino acid in response to the selector codon, the orthogonal pair is said to "suppress" the selector codon. That is, a selector codon that is not recognized by the translation system's (e.g., the cell's) endogenous machinery is not ordinarily translated, which can result in blocking production of a polypeptide that would otherwise be translated from the nucleic acid. An O-tRNA of the invention recognizes a selector codon and includes at least about, e.g., a 45%, a 50%, a 60%, a 75%, a 80%, or a 90% or more suppression efficiency in the presence of a cognate synthetase in response to a selector codon as compared to the suppression efficiency of an O-tRNA comprising or encoded by a polynucleotide sequence as set forth in the sequence listing herein. The O-RS aminoacylates the O-tRNA with an unnatural amino acid of interest, such as an alkynyl amino acid. The cell uses the O-tRNA/O-RS pair to incorporate the unnatural amino acid into a growing polypeptide chain, e.g., via a nucleic acid that comprises a polynucleotide that encodes a polypeptide of interest, where the polynucleotide comprises a selector codon that is recognized by the O-tRNA. In certain desirable aspects, the cell can include an additional O-tRNA/O-RS pair, where the additional O-tRNA is loaded by the additional O-RS with a different unnatural amino acid. For example, one of the O-tRNAs can recognize a four base codon and the other can recognize a stop codon. Alternately, multiple different stop codons or multiple different four base codons can specifically recognize different selector codons.

In certain embodiments of the invention, a cell such as an *E. coli* cell that includes an orthogonal tRNA (O-tRNA), an orthogonal aminoacyl-tRNA synthetase (O-RS), an alkynyl amino acid and a nucleic acid that comprises a polynucleotide that encodes a polypeptide of interest, where the polynucleotide comprises the selector codon that is recognized by the O-tRNA. The translation system can also be a cell-free system, e.g., any of a variety of commercially available "in vitro" transcription/translation systems in combination with an O-tRNA/ORS pair and an unnatural amino acid as described herein.

In one embodiment, the suppression efficiency of the O-RS and the O-tRNA together is about, e.g., 5 fold, 10 fold, 15 fold, 20 fold, or 25 fold or more greater than the suppression efficiency of the O-tRNA lacking the O-RS. In one aspect, the suppression efficiency of the O-RS and the O-tRNA together is at least about, e.g., 35%, 40%, 45%, 50%, 60%, 75%, 80%, or 90% or more of the suppression efficiency of an orthogonal synthetase pair as set forth in the sequence listings herein.

As noted, the invention optionally includes multiple O-tRNA/O-RS pairs in a cell or other translation system, which allows incorporation of more than one unnatural amino acid, e.g., an alkynyl amino acid and another unnatural amino acid. For example, the cell can further include an additional different O-tRNA/O-RS pair and a second unnatural amino acid, where this additional O-tRNA recognizes a second selector codon and this additional O-RS preferentially aminoacylates the O-tRNA with the second unnatural amino acid. For example, a cell that includes an O-tRNA/O-RS pair (where the O-tRNA recognizes, e.g., an amber selector codon), can further comprise a second orthogonal pair, e.g., leucyl, lysyl, glutamyl, etc., (where the second O-tRNA recognizes a different selector codon, e.g., an opal codon, a four-base codon, or the like). Desirably, the different orthogonal pairs are derived from different sources, which can facilitate recognition of different selector codons.

The O-tRNA and/or the O-RS can be naturally occurring or can be, e.g., derived by mutation of a naturally occurring tRNA and/or RS, e.g., by generating libraries of tRNAs and/or libraries of RSs, from any of a variety of organisms and/or by using any of a variety of available mutation strategies. For example, one strategy for producing an orthogonal tRNA/aminoacyl-tRNA synthetase pair involves importing a heterologous (to the host cell) tRNA/synthetase pair from, e.g., a source other than the host cell, or multiple sources, into the host cell. The properties of the heterologous synthetase candidate include, e.g., that it does not charge any host cell tRNA, and the properties of the heterologous tRNA candidate include, e.g., that it is not aminoacylated by any host cell synthetase. In addition, the heterologous tRNA is orthogonal to all host cell synthetases.

A second strategy for generating an orthogonal pair involves generating mutant libraries from which to screen and/or select an O-tRNA or O-RS. These strategies can also be combined.

Orthogonal tRNA (O-tRNA)

An orthogonal tRNA (O-tRNA) of the invention desirably mediates incorporation of an unnatural amino acid, such as an alkynyl amino acid, into a protein that is encoded by a polynucleotide that comprises a selector codon that is recognized by the O-tRNA, e.g., in vivo or in vitro. In certain embodiments, an O-tRNA of the invention includes at least about, e.g., a 45%, a 50%, a 60%, a 75%, a 80%, or a 90% or more suppression efficiency in the presence of a cognate synthetase in response to a selector codon as compared to an O-tRNA comprising or encoded by a polynucleotide sequence as set forth in the O-tRNA sequences in the sequence listing herein.

Suppression efficiency can be determined by any of a number of assays known in the art. For example, a β-galactosidase reporter assay can be used, e.g., a derivatized lacZ plasmid (where the construct has a selector codon n the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatized lacZ construct, where the construct has a corresponding sense codon at desired position rather than a selector codon.

Examples of O-tRNAs of the invention are set forth in the sequence listing herein. See also, the tables, examples and figures herein for sequences of exemplary O-tRNA and O-RS molecules. See also, the section entitled "Nucleic Acid and Polypeptide Sequence and Variants" herein. In an RNA molecule, such as an O-RS mRNA, or O-tRNA molecule, Thymine (T) is replace with Uracil (U) relative to a given sequence (or vice versa for a coding DNA), or complement thereof. Additional modifications to the bases can also be present.

The invention also includes conservative variations of O-tRNAs corresponding to particular O-tRNAs herein. For example, conservative variations of O-tRNA include those molecules that function like the particular O-tRNAs, e.g., as in the sequence listing herein and that maintain the tRNA L-shaped structure by virtue of appropriate self-complementarity, but that do not have a sequence identical to those, e.g., in the sequence listing, figures or examples herein (and, desirably, are other than wild type tRNA molecules). See also, the section herein entitled "Nucleic acids and Polypeptides Sequence and Variants."

The composition comprising an O-tRNA can further include an orthogonal aminoacyl-tRNA synthetase (O-RS), where the O-RS preferentially aminoacylates the O-tRNA with an unnatural amino acid such as an alkynyl amino acid. In certain embodiments, a composition including an O-tRNA can further include a translation system (e.g., in vitro or in vivo). A nucleic acid that comprises a polynucleotide that encodes a polypeptide of interest, where the polynucleotide comprises a selector codon that is recognized by the O-tRNA, or a combination of one or more of these can also be present in the cell. See also, the section herein entitled "Orthogonal aminoacyl-tRNA synthetases."

Methods of producing an orthogonal tRNA (O-tRNA) are also a feature of the invention. An O-tRNA produced by the method is also a feature of the invention. In certain embodiments of the invention, the O-tRNAs can be produced by generating a library of mutants. The library of mutant tRNAs can be generated using various mutagenesis techniques known in the art. For example, the mutant tRNAs can be generated by site-specific mutations, random point mutations, homologous recombination, DNA shuffling or other recursive mutagenesis methods, chimeric construction or any combination thereof.

Additional mutations can be introduced at a specific position(s), e.g., at a nonconservative position(s), or at a conservative position, at a randomized position(s), or a combination of both in a desired loop or region of a tRNA, e.g., an anticodon loop, the acceptor stem, D arm or loop, variable loop, TPC arm or loop, other regions of the tRNA molecule, or a combination thereof. Typically, mutations in a tRNA include mutating the anticodon loop of each member of the library of mutant tRNAs to allow recognition of a selector codon. The method can further include adding an additional sequence (CCA) to a terminus of the O-tRNA. Typically, an O-tRNA possesses an improvement of orthogonality for a desired organism compared to the starting material, e.g., the plurality of tRNA sequences, while preserving its affinity towards a desired RS.

The methods optionally include analyzing the similarity (and/or inferred homology) of sequences of tRNAs and/or aminoacyl-tRNA synthetases to determine potential candidates for an O-tRNA, O-RS and/or pairs thereof, that appear to be orthogonal for a specific organism. Computer programs known in the art and described herein can be used for the analysis, e.g., BLAST and pileup programs can be used. In one example, to choose potential orthogonal translational components for use in *E. coli*, a synthetase and/or a tRNA is chosen that does not display close sequence similarity to eubacterial organisms.

Typically, an O-tRNA is obtained by subjecting to, e.g., negative selection, a population of cells of a first species, where the cells comprise a member of the plurality of potential O-tRNAs. The negative selection eliminates cells that comprise a member of the library of potential O-tRNAs that is aminoacylated by an aminoacyl-tRNA synthetase (RS) that is endogenous to the cell. This provides a pool of tRNAs that are orthogonal to the cell of the first species.

In certain embodiments, in the negative selection, a selector codon(s) is introduced into a polynucleotide that encodes a negative selection marker, e.g., an enzyme that confers antibiotic resistance, e.g., β-lactamase, an enzyme that confers a detectable product, e.g., β-galactosidase, chloramphenicol acetyltransferase (CAT), e.g., a toxic product, such as barnase, at a nonessential position (e.g., still producing a functional barnase), etc. Screening/selection is optionally done by growing the population of cells in the presence of a selective agent (e.g., an antibiotic, such as ampicillin). In one embodiment, the concentration of the selection agent is varied.

For example, to measure the activity of suppressor tRNAs, a selection system is used that is based on the in vivo suppression of selector codon, e.g., nonsense or frameshift mutations introduced into a polynucleotide that encodes a negative selection marker, e.g., a gene for β-lactamase (bla). For example, polynucleotide variants, e.g., bla variants, with a selector codon at a certain position (e.g., A184), are constructed. Cells, e.g., bacteria, are transformed with these polynucleotides. In the case of an orthogonal tRNA, which cannot be efficiently charged by endogenous *E. coli* synthetases, antibiotic resistance, e.g., ampicillin resistance, should be about or less than that for a bacteria transformed with no plasmid. If the tRNA is not orthogonal, or if a heterologous synthetase capable of charging the tRNA is co-expressed in the system, a higher level of antibiotic, e.g., ampicillin, resistance is be observed. Cells, e.g., bacteria, are chosen that are unable to grow on LB agar plates with antibiotic concentrations about equal to cells transformed with no plasmids.

In the case of a toxic product (e.g., ribonuclease or barnase), when a member of the plurality of potential tRNAs is aminoacylated by endogenous host, e.g., *Escherichia coli* synthetases (i.e., it is not orthogonal to the host, e.g., *Escherichia coli* synthetases), the selector codon is suppressed and the toxic polynucleotide product produced leads to cell death. Cells harboring orthogonal tRNAs or non-functional tRNAs survive.

In one embodiment, the pool of tRNAs that are orthogonal to a desired organism are then subjected to a positive selection in which a selector codon is placed in a positive selection marker, e.g., encoded by a drug resistance gene, such a β-lactamase gene. The positive selection is performed on a cell comprising a polynucleotide encoding or comprising a member of the pool of tRNAs that are orthogonal to the cell, a polynucleotide encoding a positive selection marker, and a polynucleotide encoding a cognate RS. In certain embodiments, the second population of cells comprises cells that were not eliminated by the negative selection. The polynucleotides are expressed in the cell and the cell is grown in the presence of a selection agent, e.g., ampicillin. tRNAs are then selected for their ability to be aminoacylated by the coexpressed cognate synthetase and to insert an amino acid in response to this selector codon. Typically, these cells show an enhancement in suppression efficiency compared to cells harboring non-functional tRNA(s), or tRNAs that cannot efficiently be recognized by the synthetase of interest. The cell harboring the non-functional tRNAs or tRNAs that are not efficiently recognized by the synthetase of interest, are sensitive to the antibiotic. Therefore, tRNAs that: (i) are not substrates for endogenous host, e.g., *Escherichia coli*, synthetases; (ii) can be aminoacylated by the synthetase of interest; and (iii) are functional in translation, survive both selections.

Accordingly, the same marker can be either a positive or negative marker, depending on the context in which it is screened. That is, the marker is a positive marker if it is screened for, but a negative marker if screened against.

The stringency of the selection, e.g., the positive selection, the negative selection or both the positive and negative selection, in the above described-methods, optionally includes varying the selection stringency. For example, because barnase is an extremely toxic protein, the stringency of the negative selection can be controlled by introducing different numbers of selector codons into the barnase gene and/or by using an inducible promoter. In another example, the concentration of the selection or screening agent is varied (e.g., ampicillin concentration). In one aspect of the invention, the stringency is varied because the desired activity can be low during early rounds. Thus, less stringent selection criteria are applied in early rounds and more stringent criteria are applied in later rounds of selection. In certain embodiments, the negative selection, the positive selection or both the negative and positive selection can be repeated multiple times. Multiple different negative selection markers, positive selection markers or both negative and positive selection markers can be used. In certain embodiments, the positive and negative selection marker can be the same.

Other types of selections/screening can be used in the invention for producing orthogonal translational components, e.g., an O-tRNA, an O-RS, and an O-tRNA/O-RS pair that loads an unnatural amino acid such as an alkynyl amino acid in response to a selector codon. For example, the negative selection marker, the positive selection marker or both the positive and negative selection markers can include a marker that fluoresces or catalyzes a luminescent reaction in the presence of a suitable reactant. In another embodiment, a product of the marker is detected by fluorescence-activated cell sorting (FACS) or by luminescence. Optionally, the marker includes an affinity based screening marker. See also, Francisco, J. A., et al., (1993) *Production and fluorescence-activated cell sorting of Escherichia coli expressing a functional antibody fragment oil the external surface. Proc Natl Acad Sci USA.* 90:10444-8.

Additional methods for producing a recombinant orthogonal tRNA can be found, e.g., in International Application Publications WO 2002/086075, entitled "METHODS AND COMPOSITIONS FOR THE PRODUCTION OF ORTHOGONAL tRNA AMINOACYL-tRNA SYNTHETASE PAIRS;" WO 2004/094593, entitled "EXPANDING THE EUKARYOTIC GENETIC CODE;" and WO 2005/019415, filed Jul. 7, 2004. See also Forster et al., (2003) *Programming peptidomimetic synthetases by translating genetic codes designed de novo PNAS* 100(11):6353-6357;

and, Feng et al., (2003), *Expanding tRNA recognition of a tRNA synthetase by a single amino acid change, PNAS* 100 (10): 5676-5681.

Orthogonal Aminoacyl-tRNA Synthetase (O-RS)

An O-RS of the invention preferentially aminoacylates an O-tRNA with an unnatural amino acid such as an alkynyl amino acid, for example, para-propargyloxyphenylalanine, in vitro or in vivo. An O-RS of the invention can be provided to the translation system, e.g., a cell, by a polypeptide that includes an O-RS and/or by a polynucleotide that encodes an O-RS or a portion thereof. For example, an example O-RS comprises an amino acid sequence as set forth in the sequence listing and examples herein, or a conservative variation thereof. In another example, an O-RS, or a portion thereof, is encoded by a polynucleotide sequence that encodes an amino acid comprising sequence in the sequence listing or examples herein, or a complementary polynucleotide sequence thereof. See, e.g., the tables and examples herein for sequences of exemplary O-RS molecules. See also, the section entitled "Nucleic Acid and Polypeptide Sequence and Variants" herein.

Methods for identifying an orthogonal aminoacyl-tRNA synthetase (O-RS), e.g., an O-RS, for use with an O-tRNA, are also a feature of the invention. For example, a method includes subjecting to selection, e.g., positive selection, a population of cells of a first species, where the cells individually comprise: 1) a member of a plurality of aminoacyl-tRNA synthetases (RSs), (e.g., the plurality of RSs can include mutant RSs, RSs derived from a species other than the first species or both mutant RSs and RSs derived from a species other than the first species); 2) the orthogonal tRNA (O-tRNA) (e.g., from one or more species); and 3) a polynucleotide that encodes an (e.g., positive) selection marker and comprises at least one selector codon. Cells are selected or screened for those that show an enhancement in suppression efficiency compared to cells lacking or with a reduced amount of the member of the plurality of RSs. Suppression efficiency can be measured by techniques known in the art and as described herein. Cells having an enhancement in suppression efficiency comprise an active RS that aminoacylates the O-tRNA. A level of aminoacylation (in vitro or in vivo) by the active RS of a first set of tRNAs from the first species is compared to the level of aminoacylation (in vitro or in vivo) by the active RS of a second set of tRNAs from the second species. The level of aminoacylation can be determined by a detectable substance (e.g., a labeled amino acid or unnatural amino acid, e.g., a labeled para-propargyloxyphenylalanine). The active RS that more efficiently aminoacylates the second set of tRNAs compared to the first set of tRNAs is typically selected, thereby providing an efficient (optimized) orthogonal aminoacyl-tRNA synthetase for use with the O-tRNA. An O-RS, identified by the method, is also a feature of the invention.

Any of a number of assays can be used to determine aminoacylation. These assays can be performed in vitro or in vivo. For example, in vitro aminoacylation assays are described in, e.g., Hoben and Soll (1985) *Methods Enzymol.* 113:55-59. Aminoacylation can also be determined by using a reporter along with orthogonal translation components and detecting the reporter in a cell expressing a polynucleotide comprising at least one selector codon that encodes a protein. See also, WO 2002/085923, entitled "IN VIVO INCORPORATION OF UNNATURAL AMINO ACIDS;" and WO 2004/094593, entitled "EXPANDING THE EUKARYOTIC GENETIC CODE."

Identified O-RS can be further manipulated to alter substrate specificity of the synthetase, so that only a desired unnatural amino acid, e.g., an alkynyl amino acid, but not any of the common 20 amino acids, are charged to the O-tRNA. Methods to generate an orthogonal aminoacyl tRNA synthetase with a substrate specificity for an unnatural amino acid include mutating the synthetase, e.g., at the active site in the synthetase, at the editing mechanism site in the synthetase, at different sites by combining different domains of synthetases, or the like, and applying a selection process. A strategy is used, which is based on the combination of a positive selection followed by a negative selection. In the positive selection, suppression of the selector codon introduced at a nonessential position(s) of a positive marker allows cells to survive under positive selection pressure. In the presence of both natural and unnatural amino acids, survivors thus encode active synthetases charging the orthogonal suppressor tRNA with either a natural or unnatural amino acid. In the negative selection, suppression of a selector codon introduced at a nonessential position(s) of a negative marker removes synthetases with natural amino acid specificities. Survivors of the negative and positive selection encode synthetases that aminoacylate (charge) the orthogonal suppressor tRNA with unnatural amino acids only. These synthetases can then be subjected to further mutagenesis, e.g., DNA shuffling or other recursive mutagenesis methods.

A library of mutant O-RSs can be generated using various mutagenesis techniques known in the art. For example, the mutant RSs can be generated by site-specific mutations, random point mutations, homologous recombination, DNA shuffling or other recursive mutagenesis methods, chimeric construction or any combination thereof. For example, a library of mutant RSs can be produced from two or more other, e.g., smaller, less diverse "sub-libraries." Chimeric libraries of RSs are also included in the invention. It should be noted that libraries of tRNA synthetases from various organism (e.g., microorganisms such as eubacteria or archaebacteria) such as libraries that comprise natural diversity (see, e.g., U.S. Pat. No. 6,238,884 to Short et al; U.S. Pat. No. 5,756,316 to Schallenberger et al; U.S. Pat. No. 5,783,431 to Petersen et al; U.S. Pat. No. 5,824,485 to Thompson et al; U.S. Pat. No. 5,958,672 to Short et al), are optionally constructed and screened for orthogonal pairs.

Once the synthetases are subject to the positive and negative selection/screening strategy, these synthetases can then be subjected to further mutagenesis. For example, a nucleic acid that encodes the O-RS can be isolated; a set of polynucleotides that encode mutated O-RSs (e.g., by random mutagenesis, site-specific mutagenesis, recombination or any combination thereof) can be generated from the nucleic acid; and, these individual steps or a combination of these steps can be repeated until a mutated O-RS is obtained that preferentially aminoacylates the O-tRNA with the unnatural amino acid, e.g., an alkynyl amino acid. In one aspect of the invention, the steps are performed multiple times, e.g., at least two times.

Additional levels of selection/screening stringency can also be used in the methods of the invention, for producing O-tRNA, O-RS, or pairs thereof. The selection or screening stringency can be varied on one or both steps of the method to produce an O-RS. This could include, e.g., varying the amount of selection/screening agent that is used, etc. Additional rounds of positive and/or negative selections can also be performed. Selecting or screening can also comprise one or more of a change in amino acid permeability, a change in translation efficiency, a change in translational fidelity, etc. Typically, the one or more change is based upon a mutation in one or more gene in an organism in which an orthogonal tRNA-tRNA synthetase pair is used to produce protein.

Additional general details for producing O-RS, and altering the substrate specificity of the synthetase can be found in Internal Publication Number WO 2002/086075, entitled "METHODS AND COMPOSITIONS FOR THE PRODUCTION OF ORTHOGONAL tRNA AMINOACYL-tRNA SYNTHETASE PAIRS;" and WO 2004/094593, entitled "EXPANDING THE EUKARYOTIC GENETIC CODE."

Source and Host Organisms

The orthogonal translational components (O-tRNA and O-RS) of the invention can be derived from any organism (or a combination of organisms) for use in a host translation system from any other species, with the caveat that the O-tRNA/O-RS components and the host system work in an orthogonal manner. It is not a requirement that the O-tRNA and the O-RS be derived from the same organism. In one aspect, the orthogonal components are derived from Archaea genes (i.e., archaebacteria) for use in a eubacterial host system.

For example, the orthogonal O-tRNA can be derived from an Archae organism, e.g., an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei* (Mm), *Pyrobaculum aerophilum, Pyrococcus abyssi, Sulfolobus solfataricus* (Ss), *Sulfolobus tokodaii, Thermoplasma acidophilum, Thermoplasma volcanium*, or the like, or a eubacterium, such as *Escherichia coli, Thermus thermophilus, Bacillus stearothermophilus*, or the like, while the orthogonal O-RS can be derived from an organism or combination of organisms, e.g., an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei, Pyrobaculum aerophilum, Pyrococcus abyssi, Sulfolobus solfataricus, Sulfolobus tokodaii, Thermoplasma acidophilum, Thermoplasma volcanium*, or the like, or a *eubacterium*, such as *Escherichia coli, Thermus thermophilus, Bacillus stearothermphilus*, or the like. In one embodiment, eukaryotic sources, e.g., plants, algae, protists, fungi, yeasts, animals (e.g., mammals, insects, arthropods, etc.), or the like, can also be used as sources of O-tRNAs and O-RSs.

The individual components of an O-tRNA/O-RS pair can be derived from the same organism or different organisms. In one embodiment, the O-tRNA/O-RS pair is from the same organism. Alternatively, the O-tRNA and the O-RS of the O-tRNA/O-RS pair are from different organisms.

The O-tRNA, O-RS or O-tRNA/O-RS pair can be selected or screened in vivo or in vitro and/or used in a cell, e.g., a eubacterial cell, to produce a polypeptide with an alkynyl amino acid. The eubacterial cell used is not limited, for example, *Escherichia coli, Thermus thermophilus, Bacillus stearothermphilus*, or the like. Compositions of eubacterial cells comprising translational components of the invention are also a feature of the invention.

See also, International Application Publication Number WO 2004/094593, entitled "EXPANDING THE EUKARYOTIC GENETIC CODE," filed Apr. 16, 2004, for screening O-tRNA and/or O-RS in one species for use in another species.

Selector Codons

Selector codons of the invention expand the genetic codon framework of protein biosynthetic machinery. For example, a selector codon includes, e.g., a unique three base codon, a nonsense codon, such as a stop codon, e.g., an amber codon (UAG), or an opal codon (UGA), an unnatural codon, at least a four base codon, a rare codon, or the like. A number of selector codons can be introduced into a desired gene, e.g., one or more, two or more, more than three, etc. By using different selector codons, multiple orthogonal tRNA/synthetase pairs can be used that allow the simultaneous site-specific incorporation of multiple unnatural amino acids e.g., including at least one alkynyl amino acid, using these different selector codons.

In one embodiment, the methods involve the use of a selector codon that is a stop codon for the incorporation of an alkynyl amino acid in vivo in a cell. For example, an O-tRNA is produced that recognizes the stop codon and is aminoacylated by an O-RS with an alkynyl amino acid. This O-tRNA is not recognized by the naturally occurring host's aminoacyl-tRNA synthetases. Conventional site-directed mutagenesis can be used to introduce the stop codon at the site of interest in a polynucleotide encoding a polypeptide of interest. See, e.g., Sayers, J. R., et al. (1988), 5',3' *Exonuclease in phosphorothioate-based oligonucleotide-directed mutagenesis. Nucleic Acids Res,* 791-802. When the O-RS, O-tRNA and the nucleic acid that encodes a polypeptide of interest are combined, e.g., in vivo, the alkynyl amino acid is incorporated in response to the stop codon to give a polypeptide containing the alkynyl active amino acid at the specified position. In one embodiment of the invention, the stop codon used as a selector codon is an amber codon, UAG, and/or an opal codon, UGA. In one example, a genetic code in which UAG and UGA are both used as a selector codon can encode 22 amino acids while preserving the ochre nonsense codon, UAA, which is the most abundant termination signal.

The incorporation of alkynyl active amino acids in vivo can be done without significant perturbation of the host cell. For example in non-eukaryotic cells, such as *Escherichia coli*, because the suppression efficiency for the UAG codon depends upon the competition between the O-tRNA, e.g., the amber suppressor tRNA, and the release factor 1 (RF1) (which binds to the UAG codon and initiates release of the growing peptide from the ribosome), the suppression efficiency can be modulated by, e.g., either increasing the expression level of O-tRNA, e.g., the suppressor tRNA, or using an RF1 deficient strain. In eukaryotic cells, because the suppression efficiency for the UAG codon depends upon the competition between the O-tRNA, e.g., the amber suppressor tRNA, and a eukaryotic release factor (e.g., eRF) (which binds to a stop codon and initiates release of the growing peptide from the ribosome), the suppression efficiency can be modulated by, e.g., increasing the expression level of O-tRNA, e.g., the suppressor tRNA. In addition, additional compounds can also be present, e.g., reducing agents such as dithiothretiol (DTT).

Alkynyl amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., *Biochemistry,* 32:7939 (1993). In this case, the synthetic tRNA competes with the naturally occurring tRNAArg, which exists as a minor species in *Escherichia coli.* In addition, some organisms do not use all triplet codons. An unassigned codon AGA in *Micrococcus luteus* has been utilized for insertion of amino acids in an in vitro transcription/translation extract. See, e.g., Kowal and Oliver, *Nucl. Acid. Res.* 25:4685 (1997). Components of the invention can be generated to use these rare codons in vivo.

Selector codons can also comprise extended codons, e.g., four or more base codons, such as, four, five, six or more base codons. Examples of four base codons include, e.g., AGGA, CUAG, UAGA, CCCU, and the like. Examples of five base codons include, e.g., AGGAC, CCCCU, CCCUC, CUAGA, CUACU, UAGGC and the like. Methods of the invention include using extended codons based on frameshift suppression. Four or more base codons can insert, e.g., one or multiple unnatural amino acids such as an alkynyl amino acid, into the same protein. In other embodiments, the anticodon loops can decode, e.g., at least a four-base codon, at least a five-base codon, or at least a six-base codon or more. Since there are 256 possible four-base codons, multiple unnatural amino acids can be encoded in the same cell using a four or more base codon. See also, Anderson et al., (2002) *Exploring the Limits of Codon and Anticodon Size, Chemistry and Biology,* 9:237-244; and, Magliery, (2001) *Expanding the Genetic Code: Selection of Efficient Suppressors of Four-base Codons and Identification of "Shifty" Four-base Codons with a Library Approach in Escherichia coli, J. Mol. Biol.* 307: 755-769.

For example, four-base codons have been used to incorporate unnatural amino acids into proteins using in vitro biosynthetic methods. See, e.g., Ma et al., (1993) *Biochemistry,* 32:7939; and Hohsaka et al., (1999) *J. Am. Chem. Soc.,* 121: 34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.,* 121:12194. In an in vivo study, Moore et al. examined the ability of $tRNA^{Leu}$ derivatives with NCUA anticodons to suppress UAGN codons (N can be U, A, G, or C), and found that the quadruplet UAGA can be decoded by a $tRNA^{Leu}$ with a UCUA anticodon with an efficiency of 13 to 26% with little decoding in the 0 or −1 frame. See Moore et al., (2000) *J. Mol. Biol.,* 298:195. In one embodiment, extended codons based on rare codons or nonsense codons can be used in invention, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid analogues into protein, Nature Biotechnology,* 20:177-182. See also Wu, Y., et al., (2002) *J. Am. Chem. Soc.* 124:14626-14630. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.,* 111:8322; and Piccirilli et al., (1990) *Nature,* 343:33; Kool, (2000) *Curr. Opin. Chem. Biol.,* 4:602. These bases in general mispair to some degree with natural bases and cannot be enzymatically replicated. Kool and co-workers demonstrated that hydrophobic packing interactions between bases can replace hydrogen bonding to drive the formation of base pair. See Kool, (2000) *Curr. Opin. Chem. Biol.* 4:602; and Guckian and Kool, (1998) *Angew. Chem. Int. Ed. Engl.,* 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.,* 121:11586; and Ogawa et al., (2000) *J. Am. Chem. Soc.,* 122:3274. A 3MN:3MN self-pair can be synthesized by KF with efficiency and selectivity sufficient for biological function. See, e.g., Ogawa et al., (2000) *J. Am. Chem. Soc.,* 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.,* 123:7439. A novel metallobase pair, Dipic:Py, has also been developed, which forms a stable pair upon binding Cu(II). See Meggers et al., (2000) *J. Am. Chem. Soc.,* 122:10714. Because extended codons and unnatural codons are intrinsically orthogonal to natural codons, the methods of the invention can take advantage of this property to generate orthogonal tRNAs for them.

A translational bypassing system can also be used to incorporate an alkynyl amino acid in a desired polypeptide. In a translational bypassing system, a large sequence is inserted into a gene but is not translated into protein. The sequence contains a structure that serves as a cue to induce the ribosome to hop over the sequence and resume translation downstream of the insertion.

Unnatural Amino Acids

As used herein, an unnatural amino acid refers to any amino acid, modified amino acid, or amino acid analogue other than selenocysteine and/or pyrrolysine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

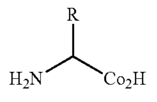

I

An unnatural amino acid is typically any structure having Formula I wherein the R group is any substituent other than one used in the twenty natural amino acids. See e.g., *Biochemistry* by L. Stryer, 3rd ed. 1988, Freeman and Company, New York, for structures of the twenty natural amino acids. Note that, the unnatural amino acids of the invention can be naturally occurring compounds other than the twenty alpha-amino acids above.

Because the unnatural amino acids of the invention typically differ from the natural amino acids in side chain, the unnatural amino acids form amide bonds with other amino acids, e.g., natural or unnatural, in the same manner in which they are formed in naturally occurring proteins. However, the unnatural amino acids have side chain groups that distinguish them from the natural amino acids.

Of particular interest herein are unnatural amino acids that comprise a reactive alkynyl group, e.g., an unnatural amino acid comprising an alkyne moiety that reacts specifically and regioselectively with an azido moiety. For example, in an alkynyl amino acid, R in Formula I includes any alkyne-containing structure. For example, para-propargyloxyphenylalanine (abbreviated pPRO-Phe; see FIG. 1A) is a desired unnatural alkynyl amino acid that finds use with the invention. It is not intended that the invention be limited to the use of pPRO-Phe with orthogonal translation components. For example, a variety of other alkynyl amino acids are contemplated (see FIGS. 8A and 8B), including, but not limited to, e.g., 2-amino-4-pentynoic acid
2-amino-3-(4-ethynylphenyl)propanoic acid
2-amino-3-[4-(prop-2-ynyl)phenyl]propanoic acid
2-amino-3-(prop-2-ynyloxy)propanoic acid
2-amino-3-(prop-2-ynylthio)propanoic acid
3-[(prop-2-ynyloxy)carbonyl]-2-aminopropanoic acid
4-[(prop-2-ynyloxy)carbonyl]-2-aminobutanoic acid In other unnatural amino acids, for example, R in Formula I optionally comprises an alkyl-, aryl-, acyl-, hydrazine, cyano-, halo-, hydrazide, alkenyl, ether, borate, boronate, phospho, phosphono, phosphine, enone, imine, ester, hydroxylamine, amine, and the like, or any combination thereof. Other unnatural amino acids of interest include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, biotin or biotin-analogue containing amino acids, keto containing amino acids, glycosylated amino acids, a saccharide moiety attached to the amino acid side chain, amino acids comprising polyethylene glycol or polyether, heavy atom substituted amino acids, chemically cleavable or photocleavable amino acids, amino acids with an elongated side chain as compared to natural amino acids (e.g., polyethers or long chain hydrocarbons, e.g., greater than about 5, greater than about 10 carbons, etc.), carbon-linked sugar-containing amino acids, amino thioacid containing amino acids, and amino acids containing one or more toxic moiety.

In another aspect, the invention provides alkynyl amino acids having the general structure illustrated by Formula IV below:

IV

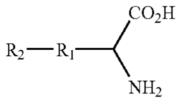

An alkyne amino acid having this structure is typically any structure where $R_1$ is a substituent used in one of the twenty natural amino acids and $R_2$ is an alkynyl substituent. Thus, this type of alkynyl amino acid can be viewed as a natural amino acid derivative.

As stated above, it is not intended that the invention be limited to the use of the unnatural alkynyl amino acid para-propargyloxyphenylalanine (pPRO-Phe). Indeed, any alkynyl amino acid that can be used in an orthogonal translation system of the invention in a eubacteria is with the scope of the invention. A variety of other alkynyl amino acids are known, for example, the alkynyl amino acids provided in FIG. 8. Since some of these alkynyl amino acid structures are very similar to pPRO-Phe, it is contemplated that some of these amino acids can be incorporated into proteins in eubacteria using the orthogonal tRNA and aminoacyl-tRNA synthetase components provided herein, e.g., the O-tRNA of SEQ ID NO: 1 and the O-RS of SEQ ID NO: 4, 6, 8, 10, 12, 14, 16, 18, or conservative variants thereof. Thus, the invention also provides methods for the incorporation of other alkynyl amino acids in addition to pPRO-Phe. Regardless of whether the orthogonal components provided in TABLE 4 (see EXAMPLE 9) are able to incorporate alkynyl amino acids in addition to pPRO-Phe, the disclosure provides sufficient teaching to construct orthogonal tRNA components that will incorporate these other alkynyl amino acids, and furthermore those orthogonal components are within the scope of the present invention.

In addition to unnatural amino acids that contain novel side chains such as the alkynyl group, unnatural alkynyl amino acids can also optionally comprise modified backbone structures, e.g., as illustrated by the structures of Formula II and III:

II

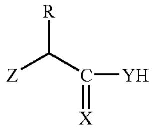

III

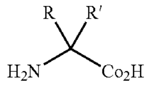

wherein Z typically comprises OH, $NH_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural alkynyl side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3,4,6,7,8, and 9 membered ring proline analogues, β and γ amino acids such as substituted β-alanine and γ-amino butyric acid.

For example, many unnatural amino acids (including some alkynyl amino acids) are based on natural amino acids, such as tyrosine, serine, cysteine, aspartate, glutamate, and the like. For example, the alkynyl amino acids:

2-amino-3-(prop-2-ynyloxy)propanoic acid;
2-amino-3-(prop-2-ynylthio)propanoic acid;
3-[(prop-2-ynyloxy)carbonyl]-2-aminopropanoic acid; and
4-[(prop-2-ynyloxy)carbonyl]-2-aminobutanoic acid, can all be derived from natural amino acids.

Tyrosine analogs include para-substituted tyrosines, ortho-substituted tyrosines, and meta substituted tyrosines, wherein the substituted tyrosine comprises an alkynyl group, acetyl group, a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, α-hydroxy derivatives, γ-substituted derivatives, cyclic derivatives, and amide substituted glutamine derivatives. Example phenylalanine analogs include, but are not limited to, para-substituted phenylalanines, ortho-substituted phenyalanines, and meta-substituted phenylalanines, wherein the substituent comprises an alkynyl group, a hydroxy group, a methoxy group, a methyl group, an allyl group, an aldehyde, a nitro, a thiol group, or keto group, or the like. Specific examples of unnatural amino acids include, but are not limited to, a p-propargyloxyphenylalanine, a 3,4-dihydroxy-L-phenyalanine (DBP), a 3,4,6-trihydroxy-L-phenylalanine, a 3,4,5-trihydroxy-L-phenylalanine, 4-nitro-phenylalanine, a p-acetyl-L-phenylalanine, O-methyl-L-tyrosine, an L-3-(2-naphthyl)alanine, a 3-methyl-phenylalanine, an O-4-allyl-L-tyrosine, a 4-propyl-L-tyrosine, a 3-nitro-tyrosine, a 3-thiol-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like. The structures of a variety of unnatural amino acids are provided herein, see, for example, FIGS. 1A, 8A and 8B. See also Published International Application WO 2004/094593, entitled "EXPANDING THE EUKARYOTIC GENETIC CODE."

Chemical Synthesis of Unnatural Amino Acids

Many of the unnatural amino acids provided above are commercially available, e.g., from Sigma (USA) or Aldrich (Milwaukee, Wis., USA). Those that are not commercially available are optionally synthesized as provided in various publications or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) *J. Med. Chem.*, 38, 4660-4669; King, F. E. & Kidd, D. A. A. (1949) *A New Synthesis of Glutamine and of γ-Dipeptides of Glutamic Acid from Phthylated Intermediates. J. Chem. Soc.,* 3315-3319; Friedman, O. M. & Chatterrji, R. (1959) *Synthesis of Derivatives of Glutamine as Model Substrates for Anti-Tumor Agents. J. Am. Chem. Soc.* 81, 3750-3752; Craig, J. C. et al. (1988) *Absolute Configuration of the Enantiomers of 7-Chloro-4 [[4-(diethylamino)-1-methylbutyl]amino]quinoline (Chloroquine). J. Org. Chem.* 53, 1167-1170; Azoulay, M., Vilmont, M. & Frappier, F. (1991) *Glutamine analogues as Potential Antimalarials. Eur. J. Med. Chem.* 26, 201-5; Koskinen, A. M. P. & Rapoport, H. (1989) *Synthesis of 4-Substituted Prolines as Conformationally Constrained Amino Acid Analogues. J. Org. Chem.* 54, 1859-1866; Christie, B. D. & Rapoport, H. (1985) *Synthesis of Optically Pure Pipecolates from L-Asparagine. Application to the Total Synthesis of (+)-Apovincamine through Amino Acid Decarbonylation and Iminium Ion Cyclization. J. Org. Chem.* 1989:1859-1866; Barton et al., (1987) *Synthesis of Novel α-Amino-Acids and Derivatives Using Radical Chemistry: Synthesis of L- and D-α-Amino-Adipic Acids, L-α-aminopimelic Acid and Appropriate Unsaturated Derivatives. Tetrahedron Lett.* 43:4297-4308; and, Subasinghe et al., (1992) *Quisqualic acid analogues: synthesis of beta-heterocyclic 2-aminopropanoic acid derivatives and their activity at a novel quisqualate-sensitized site. J. Med. Chem.* 35:4602 7. See also International Publication WO 2004/058946, entitled "PROTEIN ARRAYS," filed on Dec. 22, 2003.

Cellular Uptake of Unnatural Amino Acids

Unnatural amino acid uptake by a cell is one issue that is typically considered when designing and selecting unnatural amino acids, e.g., for incorporation into a protein. For example, the high charge density of α-amino acids suggests that these compounds are unlikely to be cell permeable. Natural amino acids are taken up into the cell via a collection of protein-based transport systems often displaying varying degrees of amino acid specificity. A rapid screen can be done which assesses which unnatural amino acids, if any, are taken up by cells. See, e.g., the toxicity assays in, e.g., International Publication WO 2004/058946, entitled "PROTEIN ARRAYS," filed on Dec. 22, 2003; and Liu and Schultz (1999) *Progress toward the evolution of an organism with an expanded genetic code*. PNAS 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, e.g., in a cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923, supra) relies on the addition of a combination of known enzymes from other organisms. The genes for these enzymes can be introduced into a cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, e.g., in Genbank. Artificially evolved enzymes are also optionally added into a cell in the same manner. In this manner, the cellular machinery and resources of a cell are manipulated to produce unnatural amino acids.

Indeed, any of a variety of methods can be used for producing novel enzymes for use in biosynthetic pathways, or for evolution of existing pathways, for the production of unnatural amino acids, in vitro or in vivo. Many available methods of evolving enzymes and other biosynthetic pathway components can be applied to the present invention to produce unnatural amino acids (or, indeed, to evolve synthetases to have new substrate specificities or other activities of interest). For example, DNA shuffling is optionally used to develop novel enzymes and/or pathways of such enzymes for the production of unnatural amino acids (or production of new synthetases), in vitro or in vivo. See, e.g., Stemmer (1994), *Rapid evolution of a protein in vitro by DNA shuffling, Nature* 370(4):389-391; and, Stemmer, (1994), *DNA shuffling by random fragmentation and reassembly: In vitro recombina-*

*tion for molecular evolution, Proc. Natl. Acad. Sci. USA.*, 91:10747-10751. A related approach shuffles families of related (e.g., homologous) genes to quickly evolve enzymes with desired characteristics. An example of such "family gene shuffling" methods is found in Crameri et al. (1998) "DNA shuffling of a family of genes from diverse species accelerates directed evolution" *Nature,* 391(6664): 288-291. New enzymes (whether biosynthetic pathway components or synthetases) can also be generated using a DNA recombination procedure known as "incremental truncation for the creation of hybrid enzymes" ("ITCHY"), e.g., as described in Ostermeier et al. (1999) "A combinatorial approach to hybrid enzymes independent of DNA homology" *Nature Biotech* 17:1205. This approach can also be used to generate a library of enzyme or other pathway variants which can serve as substrates for one or more in vitro or in vivo recombination methods. See, also, Ostermeier et al. (1999) "Combinatorial Protein Engineering by Incremental Truncation," *Proc. Natl. Acad. Sci. USA,* 96: 3562-67, and Ostermeier et al. (1999), "Incremental Truncation as a Strategy in the Engineering of Novel Biocatalysts," *Biological and Medicinal Chemistry,* 7: 2139-44. Another approach uses exponential ensemble mutagenesis to produce libraries of enzyme or other pathway variants that are, e.g., selected for an ability to catalyze a biosynthetic reaction relevant to producing an unnatural amino acid (or a new synthetase). In this approach, small groups of residues in a sequence of interest are randomized in parallel to identify, at each altered position, amino acids which lead to functional proteins. Examples of such procedures, which can be adapted to the present invention to produce new enzymes for the production of unnatural amino acids (or new synthetases) are found in Delegrave & Youvan (1993) *Biotechnology Research* 11:1548-1552. In yet another approach, random or semi-random mutagenesis using doped or degenerate oligonucleotides for enzyme and/or pathway component engineering can be used, e.g., by using the general mutagenesis methods of e.g., Arkin and Youvan (1992) "Optimizing nucleotide mixtures to encode specific subsets of amino acids for semi-random mutagenesis" *Biotechnology* 10:297-300; or Reidhaar-Olson et al. (1991) "Random mutagenesis of protein sequences using oligonucleotide cassettes" *Methods Enzymol.* 208:564-86. Yet another approach, often termed a "non-stochastic" mutagenesis, which uses polynucleotide reassembly and site-saturation mutagenesis can be used to produce enzymes and/or pathway components, which can then be screened for an ability to perform one or more synthetase or biosynthetic pathway function (e.g., for the production of unnatural amino acids in vivo). See, e.g., Short "NON-STOCHASTIC GENERATION OF GENETIC VACCINES AND ENZYMES" WO 00/46344.

An alternative to such mutational methods involves recombining entire genomes of organisms and selecting resulting progeny for particular pathway functions (often referred to as "whole genome shuffling"). This approach can be applied to the present invention, e.g., by genomic recombination and selection of an organism (e.g., an *E. coli* or other cell) for an ability to produce an unnatural amino acid (or intermediate thereof). For example, methods taught in the following publications can be applied to pathway design for the evolution of existing and/or new pathways in cells to produce unnatural amino acids in vivo: Patnaik et al. (2002) "Genome shuffling of *lactobacillus* for improved acid tolerance" *Nature Biotechnology,* 20(7): 707-712; and Zhang et al. (2002) "Genome shuffling leads to rapid phenotypic improvement in bacteria" Nature, February 7, 415(6872): 644-646.

Other techniques for organism and metabolic pathway engineering, e.g., for the production of desired compounds are also available and can also be applied to the production of unnatural amino acids. Examples of publications teaching useful pathway engineering approaches include: Nakamura and White (2003) "Metabolic engineering for the microbial production of 1,3 propanediol" *Curr. Opin. Biotechnol.* 14(5):454-9; Berry et al. (2002) "Application of Metabolic Engineering to improve both the production and use of Biotech Indigo" *J. Industrial Microbiology and Biotechnology* 28:127-133; Banta et al. (2002) "Optimizing an artificial metabolic pathway: Engineering the cofactor specificity of *Corynebacterium* 2,5-diketo-D-gluconic acid reductase for use in vitamin C biosynthesis" *Biochemistry,* 41(20), 6226-36; Selivonova et al. (2001) "Rapid Evolution of Novel Traits in Microorganisms" *Applied and Environmental Microbiology,* 67:3645, and many others.

Regardless of the method used, typically, the unnatural amino acid produced with an engineered biosynthetic pathway of the invention is produced in a concentration sufficient for efficient protein biosynthesis, e.g., a natural cellular amount, but not to such a degree as to significantly affect the concentration of other cellular amino acids or to exhaust cellular resources. Typical concentrations produced in vivo in this manner are about 10 mM to about 0.05 mM. Once a cell is engineered to produce enzymes desired for a specific pathway and an unnatural amino acid is generated, in vivo selections are optionally used to further optimize the production of the unnatural amino acid for both ribosomal protein synthesis and cell growth.

Orthogonal Components for Incorporating Para-Propargyloxyphenylalanine (pPRO-Phe)

The invention provides compositions and methods of producing orthogonal components for incorporating an alkynyl amino acid, e.g., para-propargyloxyphenylalanine (pPRO-Phe), into a growing polypeptide chain in response to a selector codon, e.g., an amber stop codon, a nonsense codon, a four or more base codon, etc., e.g., in vivo. For example, the invention provides orthogonal-tRNAs (O-tRNAs), orthogonal aminoacyl-tRNA synthetases (O-RSs) and pairs thereof. These pairs can be used to incorporate pPRO-Phe into growing polypeptide chains.

A composition of the invention includes an orthogonal aminoacyl-tRNA synthetase (O-RS), where the O-RS preferentially aminoacylates an O-tRNA with a pPRO-Phe. In certain embodiments, the O-RS comprises an amino acid sequence comprising SEQ ID NO: 4, 6, 8, 10, 12, 14 16 or 18, or a conservative variation thereof. In certain embodiments of the invention, the O-RS preferentially aminoacylates the O-tRNA over any endogenous tRNA with an alkynyl amino acid such as pPRO-Phe, where the O-RS has a bias for the O-tRNA, and where the ratio of O-tRNA charged with pPRO-Phe to the endogenous tRNA charged with pPRO-Phe is greater than 1:1, and more preferably where the O-RS charges the O-tRNA exclusively or nearly exclusively.

A composition that includes an O-RS can optionally further include an orthogonal tRNA (O-tRNA), where the O-tRNA recognizes a selector codon. Typically, an O-tRNA of the invention includes at least about, e.g., a 45%, a 50%, a 60%, a 75%, an 80%, or a 90% or more suppression efficiency in the presence of a cognate synthetase in response to a selector codon as compared to the suppression efficiency of an O-tRNA comprising or encoded by a polynucleotide sequence as set forth in the sequence listings (e.g., SEQ ID NO: 1) and examples herein. In one embodiment, the suppression efficiency of the O-RS and the O-tRNA together is, e.g., 5 fold, 10 fold, 15 fold, 20 fold, 25 fold or more greater than the suppression efficiency of the O-tRNA in the absence of an O-RS. In one aspect, the suppression efficiency of the O-RS and the O-tRNA together is at least 45% of the suppression efficiency of an orthogonal tyrosyl-tRNA synthetase pair derived from *Methanococcus jannaschii.*

A composition that includes an O-tRNA can optionally include a cell (e.g., a eubacterial cell, such as an *E. coli* cell and the like), and/or a translation system.

A cell (e.g., a eubacterial cell) comprising a translation system is also provided by the invention, where the translation system includes an orthogonal-tRNA (O-tRNA); an orthogonal aminoacyl-tRNA synthetase (O-RS); and, an alkynyl amino acid, e.g., para-propargyloxyphenylalanine (pPRO-Phe). Typically, the O-RS preferentially aminoacylates the O-tRNA over any endogenous tRNA with an alkynyl amino acid such as pPRO-Phe, where the O-RS has a bias for the O-tRNA, and where the ratio of O-tRNA charged with pPRO-Phe to the endogenous tRNA charged with pPRO-Phe is greater than 1:1, and more preferably where the O-RS charges the O-tRNA exclusively or nearly exclusively. The O-tRNA recognizes the first selector codon, and the O-RS preferentially aminoacylates the O-tRNA with pPRO-Phe. In one embodiment, the O-tRNA comprises or is encoded by a polynucleotide sequence as set forth in SEQ ID NO: 1, or a complementary polynucleotide sequence thereof. In one embodiment, the O-RS comprises an amino acid sequence as set forth in any one of SEQ ID NO: 4, 6, 8, 10, 12, 14 16 or 18, or a conservative variation thereof.

A cell of the invention can optionally further comprise an additional different O-tRNA/O-RS pair and a second unnatural amino acid, e.g., where this O-tRNA recognizes a second selector codon and this O-RS preferentially aminoacylates the corresponding O-tRNA with the second unnatural amino acid, where the second amino acid is different from pPRO-Phe. Optionally, a cell of the invention includes a nucleic acid that comprises a polynucleotide that encodes a polypeptide of interest, where the polynucleotide comprises a selector codon that is recognized by the O-tRNA.

In certain embodiments, a cell of the invention is a eubacterial cell such as *E. coli*, that includes an orthogonal-tRNA (O-tRNA), an orthogonal aminoacyl-tRNA synthetase (O-RS), an alkynyl amino acid such as pPRO-Phe, and a nucleic acid that comprises a polynucleotide that encodes a polypeptide of interest, where the polynucleotide comprises the selector codon that is recognized by the O-tRNA. In certain embodiments of the invention, the O-RS preferentially aminoacylates the O-tRNA with an efficiency that is greater than the efficiency with which the O-RS aminoacylates any endogenous tRNA.

In certain embodiments of the invention, an O-tRNA of the invention comprises or is encoded by a polynucleotide sequence as set forth in the sequence listings (e.g., SEQ ID NO: 1) or examples herein, or a complementary polynucleotide sequence thereof. In certain embodiments of the invention, an O-RS comprises an amino acid sequence as set forth in the sequence listings, or a conservative variation thereof. In one embodiment, the O-RS or a portion thereof is encoded by a polynucleotide sequence encoding an amino acid as set forth in the sequence listings or examples herein, or a complementary polynucleotide sequence thereof.

The O-tRNA and/or the O-RS of the invention can be derived from any of a variety of organisms (e.g., eukaryotic and/or non-eukaryotic organisms).

Polynucleotides are also a feature of the invention. A polynucleotide of the invention includes an artificial (e.g., man-made, and not naturally occurring) polynucleotide comprising a nucleotide sequence encoding a polypeptide as set forth in the sequence listings herein, and/or is complementary to or that polynucleotide sequence. A polynucleotide of the invention can also includes a nucleic acid that hybridizes to a polynucleotide described above, under highly stringent conditions, over substantially the entire length of the nucleic acid.

A polynucleotide of the invention also includes a polynucleotide that is, e.g., at least 75%, at least 80%, at least 90%, at least 95%, at least 98% or more identical to that of a naturally occurring tRNA or corresponding coding nucleic acid (but a polynucleotide of the invention is other than a naturally occurring tRNA or corresponding coding nucleic acid), where the tRNA recognizes a selector codon, e.g., a four base codon. Artificial polynucleotides that are, e.g., at least 80%, at least 90%, at least 95%, at least 98% or more identical to any of the above and/or a polynucleotide comprising a conservative variation of any the above, are also included in polynucleotides of the invention.

Vectors comprising a polynucleotide of the invention are also a feature of the invention. For example, a vector of the invention can include a plasmid, a cosmid, a phage, a virus, an expression vector, and/or the like. A cell comprising a vector of the invention is also a feature of the invention.

Methods of producing components of an O-tRNA/O-RS pair are also features of the invention. Components produced by these methods are also a feature of the invention. For example, methods of producing at least one tRNA that is orthogonal to a cell (O-tRNA) include generating a library of mutant tRNAs; mutating an anticodon loop of each member of the library of mutant tRNAs to allow recognition of a selector codon, thereby providing a library of potential O-tRNAs, and subjecting to negative selection a first population of cells of a first species, where the cells comprise a member of the library of potential O-tRNAs. The negative selection eliminates cells that comprise a member of the library of potential O-tRNAs that is aminoacylated by an aminoacyl-tRNA synthetase (RS) that is endogenous to the cell. This provides a pool of tRNAs that are orthogonal to the cell of the first species, thereby providing at least one O-tRNA. An O-tRNA produced by the methods of the invention is also provided.

In certain embodiments, the methods further comprise subjecting to positive selection a second population of cells of the first species, where the cells comprise a member of the pool of tRNAs that are orthogonal to the cell of the first species, a cognate aminoacyl-tRNA synthetase, and a positive selection marker. Using the positive selection, cells are selected or screened for those cells that comprise a member of the pool of tRNAs that is aminoacylated by the cognate aminoacyl-tRNA synthetase and that shows a desired response in the presence of the positive selection marker, thereby providing an O-tRNA. In certain embodiments, the second population of cells comprise cells that were not eliminated by the negative selection.

Methods for identifying an orthogonal-aminoacyl-tRNA synthetase that charges an O-tRNA with an alkynyl amino acid are also provided. For example, methods include subjecting a population of cells of a first species to a selection, where the cells each comprise: 1) a member of a plurality of aminoacyl-tRNA synthetases (RSs), (e.g., the plurality of RSs can include mutant RSs, RSs derived from a species other than a first species or both mutant RSs and RSs derived from a species other than a first species); 2) the orthogonal-tRNA (O-tRNA) (e.g., from one or more species); and 3) a polynucleotide that encodes a positive selection marker and comprises at least one selector codon.

Cells (e.g., a host cell) are selected or screened for those that show an enhancement in suppression efficiency compared to cells lacking or having a reduced amount of the member of the plurality of RSs. These selected/screened cells comprise an active RS that aminoacylates the O-tRNA. An orthogonal aminoacyl-tRNA synthetase identified by the method is also a feature of the invention.

Methods of producing a protein in a cell (e.g., in a eubacterial cell such as an *E. coli* cell or the like) having para-propargyloxyphenylalanine (pPRO-Phe) at a specified position are also a feature of the invention. For example, a method includes growing, in an appropriate medium, a cell, where the cell comprises a nucleic acid that comprises at least one selector codon and encodes a protein, providing pPR, and incorporating pPR into the specified position in the protein during translation of the nucleic acid with the at least one selector codon, thereby producing the protein. The cell further comprises: an orthogonal-tRNA (O-tRNA) that functions in the cell and recognizes the selector codon; and, an orthogonal aminoacyl-tRNA synthetase (O-RS) that preferentially aminoacylates the O-tRNA with pPRO-Phe. A protein produced by this method is also a feature of the invention.

The invention also provides compositions that include proteins, where the proteins comprise, e.g., pPRO-Phe. In certain embodiments, the protein comprises an amino acid sequence that is at least 75% identical to that of a known protein, e.g., a therapeutic protein, a diagnostic protein, an industrial enzyme, or portion thereof. Optionally, the composition comprises a pharmaceutically acceptable carrier.

Nucleic Acid and Polypeptide Sequence and Variants

As described above and below, the invention provides for polynucleotide sequences encoding, e.g., O-tRNAs and O-RSs, and polypeptide amino acid sequences, e.g., O-RSs, and, e.g., compositions, systems and methods comprising said sequences. Examples of said sequences, e.g., O-tRNA and O-RS amino acid and nucleotide sequences are disclosed herein (see Table 4, e.g., SEQ ID NOS: 5, 7, 9, 11, 13, 15, 17 and 19). However, one of skill in the art will appreciate that the invention is not limited to those sequences disclosed herein, e.g., as in the Examples and sequence listing. One of skill will appreciate that the invention also provides e.g., many related sequences with the functions described herein, e.g., encoding an O-tRNA or an O-RS.

The construction and analysis of O-RS species that are able to aminoacylate the O-tRNA with pPRO-Phe is described in EXAMPLE 1. This example describes the eight O-RS species that were isolated (see, FIG. 3 and EXAMPLE 9). As can be seen from these amino acid sequences, partial consensus trends in the amino acid substitutions in the eight mutant O-RS clones are observed. At least two of the following amino acids were found in the binding pocket in more than one clone: Ala32, Pro107/Gln107, Ala158, Ile159, and Ala162/Pro162 (see, SEQ ID NO: 21). The mutations Tyr32→Ala32 and Asp158→Ala158 may result in the loss of hydrogen bonds between Tyr32, Asp158 and the natural substrate tyrosine, thus disfavoring its binding. The occurrence of small and mostly hydrophobic side chains might be expected to facilitate binding of pPRO-Phe. These consensus trends allow the design of additional O-RS species that are predicted to function in an orthogonal system with the O-tRNA of SEQ ID NO: 1 in a eubacterial host system to incorporate pPRO-Phe. These consensus trends can be expressed as follows:

TABLE 1

| Amino Acid Position | Wild-type *Methanococcus jannaschii* tyrosyl-tRNA synthetase amino acid (SEQ ID NO: 2) | Orthogonal pPRO-PheRS consensus (SEQ ID NO: 21) |
|---|---|---|
| 32 | Tyr | Ala |
| 107 | Glu | Pro or Gln |
| 110 | Leu | Leu |
| 158 | Asp | Ala |
| 159 | Ile | Ile |
| 162 | Leu | Ala or Pro |

Thus, based on these consensus trends, at least four additional orthogonal pPRO-Phe synthetases (pPRO-PheRS-con1 through pPRO-PheRS-con4) can be rationally designed that are not represented in the eight pPRO-PheRS species identified experimentally (i.e., pPRO-PheRS-1 through pPRO-PheRS-8). These are as follows:

TABLE 2

| SEQ ID NO: | *Methanococcus jannaschii* tyrosyl-tRNA synthetase species | Amino Acid Position 32 | 107 | 110 | 158 | 159 | 162 |
|---|---|---|---|---|---|---|---|
| 2 | wild-type | Tyr | Glu | Leu | Asp | Ile | Leu |
| 21 | pPRO-PheRS-consensus | Ala | Pro/Gln | Leu | Ala | Ile | Ala/Pro |
| 22 | pPRO-PheRS-con1 | Ala | Pro | Leu | Ala | Ile | Ala |
| 23 | pPRO-PheRS-con2 | Ala | Pro | Leu | Ala | Ile | Pro |
| 24 | pPRO-PheRS-con3 | Ala | Gln | Leu | Ala | Ile | Ala |
| 25 | pPRO-PheRS-con4 | Ala | Gln | Leu | Ala | Ile | Pro |

The invention provides polypeptides (O-RSs) and polynucleotides, e.g., O-tRNA, polynucleotides that encode O-RSs or portions thereof, oligonucleotides used to isolate aminoacyl-tRNA synthetase clones, etc. Polynucleotides of the invention include those that encode proteins or polypeptides of interest of the invention with one or more selector codon. In addition, polynucleotides of the invention include, e.g., a polynucleotide comprising a nucleotide sequence as set forth in SEQ ID NO: 5, 7, 9, 11, 13, 15, 17 or 19; a polynucleotide that is complementary to or that encodes a polynucleotide sequence thereof. A polynucleotide of the invention also includes any polynucleotide that encodes an amino acid sequence comprising SEQ ID NO: 4, 6, 8, 10, 12, 14 16 or 18. A polynucleotide of the invention also includes a polynucleotide that encodes a polypeptide of the invention. Similarly, an artificial nucleic acid that hybridizes to a polynucleotide indicated above under highly stringent conditions over substantially the entire length of the nucleic acid (and is other than a naturally occurring polynucleotide) is a polynucleotide of the invention. In one embodiment, a composition includes a polypeptide of the invention and an excipient (e.g., buffer, water, pharmaceutically acceptable excipient, etc.). The invention also provides an antibody or antisera specifically immunoreactive with a polypeptide of the invention. An artificial polynucleotide is a polynucleotide that is man made and is not naturally occurring.

A polynucleotide of the invention also includes an artificial polynucleotide that is, e.g., at least 75%, at least 80%, at least 90%, at least 95%, at least 98% or more identical to that of a naturally occurring tRNA, (but is other than a naturally occurring tRNA). A polynucleotide also includes an artificial polynucleotide that is, e.g., at least 75%, at least 80%, at least 90%, at least 95%, at least 98% or more identical (but not 100% identical) to that of a naturally occurring tRNA.

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid sequence. Similarly, "conservative amino acid substitutions," where one or a limited number of amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 2% or 1%, of the amino acids of the polypeptide sequence, with an amino acid of the same conservative substitution group. Finally, the addition of sequences which do not alter the encoded activity of a nucleic acid molecule, such as the addition of a non-functional sequence, is a conservative variation of the basic nucleic acid.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. The following sets forth example groups that contain natural amino acids of like chemical properties, where substitutions within a group is a "conservative substitution".

TABLE 3

| Nonpolar and/or Aliphatic Side Chains | Polar, Uncharged Side Chains | Aromatic Side Chains | Positively Charged Side Chains | Negatively Charged Side Chains |
|---|---|---|---|---|
| Glycine | Serine | Phenylalanine | Lysine | Aspartate |
| Alanine | Threonine | Tyrosine | Arginine | Glutamate |
| Valine | Cysteine | Tryptophan | Histidine | |
| Leucine | Methionine | | | |
| Isoleucine | Asparagine | | | |
| Proline | Glutamine | | | |

Nucleic Acid Hybridization

Comparative hybridization can be used to identify nucleic acids of the invention, including conservative variations of nucleic acids of the invention, and this comparative hybridization method is a preferred method of distinguishing nucleic acids of the invention. In addition, target nucleic acids which hybridize to a nucleic acid represented by SEQ ID NO: 5, 7, 9, 11, 13, 15, 17 and 19, under high, ultra-high and ultra-ultra high stringency conditions are a feature of the invention. Examples of such nucleic acids include those with one or a few silent or conservative nucleic acid substitutions as compared to a given nucleic acid sequence.

A test nucleic acid is said to specifically hybridize to a probe nucleic acid when it hybridizes at least 50% as well to the probe as to the perfectly matched complementary target, i.e., with a signal to noise ratio at least half as high as hybridization of the probe to the target under conditions in which the perfectly matched probe binds to the perfectly matched complementary target with a signal to noise ratio that is at least about 5×–10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, N.Y.), as well as in *Current Protocols in Molecular Biology*, Ausubel et al., eds., *Current Protocols*, a joint venture between Greene Publishing Associates, Inc. and John Wiley & Sons, Inc., (supplemented through 2004) ("Ausubel"); Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, supra for a description of SSC buffer). Often the high stringency wash is preceded by a low stringency wash to remove background probe signal. An example low stringency wash is 2×SSC at 40° C. for 15 minutes. In general, a signal to noise ratio of 5×(or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10x, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In one aspect, the invention provides a nucleic acid that comprises a unique subsequence in a nucleic acid selected from the sequences of O-tRNAs and O-RSs disclosed herein. The unique subsequence is unique as compared to a nucleic acid corresponding to any known O-tRNA or O-RS nucleic acid sequence. Alignment can be performed using, e.g., BLAST set to default parameters. Any unique subsequence is useful, e.g., as a probe to identify the nucleic acids of the invention.

Similarly, the invention includes a polypeptide which comprises a unique subsequence in a polypeptide selected from the sequences of O-RSs disclosed herein. Here, the unique subsequence is unique as compared to a polypeptide corresponding to any of known polypeptide sequence.

The invention also provides for target nucleic acids which hybridizes under stringent conditions to a unique coding oligonucleotide which encodes a unique subsequence in a polypeptide selected from the sequences of O-RSs wherein the unique subsequence is unique as compared to a polypeptide corresponding to any of the control polypeptides (e.g., parental sequences from which synthetases of the invention were derived, e.g., by mutation). Unique sequences are determined as noted above.

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding an O-tRNA or O-RS, or the amino acid sequence of an O-RS) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid encodes a polypeptide comprising one or more unnatural amino acid, e.g. an alkynyl amino acid. The mutation process can, of course, additionally alter one or more standard codon, thereby changing one or more standard amino acid in the resulting mutant protein as well. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols in Molecular Biology*, Ausubel et al., eds., *Current Protocols*, a joint venture between Greene Publishing Associates, Inc. and John Wiley & Sons, Inc., supplemented through 2004).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information [on line]. NCBI Home Page [retrieved Sept. 21, 2004]. Retrieved from the internet: <URL: www.ncbi.nlm.nih.gov/≧. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Mutagenesis and Other Molecular Biology Techniques

Polynucleotide and polypeptides of the invention and used in the invention can be manipulated using molecular biological techniques. General texts which describe molecular biological techniques include Berger and Kimmel, *Guide to Molecular Cloning Techniques. Methods in Enzymology volume* 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2001 ("Sambrook") and *Current Protocols in Molecular Biology*, F. M. Ausubel et al., eds., *Current Protocols*, a joint venture between Greene Publishing Associates, Inc. and John Wiley & Sons, Inc., (supplemented through 2004) ("Ausubel"). These texts describe mutagenesis, the use of vectors, promoters and many other relevant topics related to, e.g., the generation of genes that include selector codons for production of proteins that include alkynyl amino acids (e.g., pPRO-Phe), orthogonal tRNAs, orthogonal synthetases, and pairs thereof.

Various types of mutagenesis are used in the invention, e.g., to mutate tRNA molecules, to produce libraries of tRNAs, to produce libraries of synthetases, to insert selector codons that encode an alkynyl amino acid in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

Host cells are genetically engineered (e.g., transformed, transduced or transfected) with the polynucleotides of the invention or constructs which include a polynucleotide of the invention, e.g., a vector of the invention, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both (e.g., shuttle vectors) and selection markers for both prokaryotic and eukaryotic systems. Vectors are suitable for replication and/or integration in prokaryotes, eukaryotes, or preferably both. See Giliman & Smith, *Gene* 8:81 (1979); Roberts, et al., *Nature,* 328:731 (1987); Schneider, B., et al., *Protein Expr. Purif.* 6435:10

(1995); Ausubel, Sambrook, Berger (all supra). The vector can be, for example, in the form of a plasmid, a bacterium, a virus, a naked polynucleotide, or a conjugated polynucleotide. The vectors are introduced into cells and/or microorganisms by standard methods including electroporation (From et al., *Proc. Natl. Acad. Sci. USA* 82, 5824 (1985), infection by viral vectors, high velocity ballistic penetration by small particles with the nucleic acid either within the matrix of small beads or particles, or on the surface (Klein et al., *Nature* 327, 70-73 (1987)), and/or the like.

A catalogue of Bacteria and Bacteriophages useful for cloning is provided, e.g., by the ATCC, e.g., *The ATCC Catalogue of Bacteria and Bacteriophage* (1996) Ghema et al. (eds) published by the ATCC. Additional basic procedures for sequencing, cloning and other aspects of molecular biology and underlying theoretical considerations are also found in Sambrook (supra), Ausubel (supra), and in Watson et al. (1992) *Recombinant DNA Second Edition* Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex. mcrc.com), The Great American Gene Company (Ramona, Calif. available on the World Wide Web at genco.com), ExpressGen Inc. (Chicago, Ill. available on the World Wide Web at expressgen.com), Operon Technologies Inc. (Alameda, Calif.) and many others.

The engineered host cells can be cultured in conventional nutrient media modified as appropriate for such activities as, for example, screening steps, activating promoters or selecting transformants. These cells can optionally be cultured into transgenic organisms. Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Proteins and Polypeptides of Interest

One significant advantage of alkynyl amino acids (but not limited to) are that proteins comprising the alkynyl amino acid can be used to crosslink or conjugate the proteins with any of a variety of small molecules, biomolecules or other proteins, etc. Proteins or polypeptides of interest with at least one alkynyl amino acid are a feature of the invention. The invention also includes polypeptides or proteins with at least one alkynyl amino acid produced using the compositions and methods of the invention. An excipient (e.g., a pharmaceutically acceptable excipient) can also be present with the protein. Optionally, a protein of the invention can include a post-translational modification (in addition to the possible subsequent modification to the alkynyl amino acid residue) at a single amino acid position or multiple positions, or the protein can have a plurality of different types of modifications.

Methods of producing a protein in a cell with an alkynyl amino acid at a specified position are also a feature of the invention. For example, a method includes growing, in an appropriate medium, the cell, where the cell comprises a nucleic acid that comprises at least one selector codon and encodes a protein; and, providing the alkynyl amino acid; where the cell further comprises: an orthogonal-tRNA (O-tRNA) that functions in the cell and recognizes the selector codon; and, an orthogonal aminoacyl-tRNA synthetase (O-RS) that preferentially aminoacylates the O-tRNA with the alkynyl amino acid. A protein produced by this method is also a feature of the invention.

In certain embodiments, the O-RS comprises a bias for the aminoacylation of the cognate O-tRNA over any endogenous tRNA in an expression system. The relative ratio between O-tRNA and endogenous tRNA that is charged by the O-RS, when the O-tRNA and O-RS are present at equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

The invention also provides compositions that include proteins, where the proteins comprise an alkynyl amino acid. In certain embodiments, the protein comprises an amino acid sequence that is at least 75% identical to that of a therapeutic protein, a diagnostic protein, an industrial enzyme, or portion thereof.

The compositions of the invention and compositions made by the methods of the invention optionally are in a cell. The O-tRNA/O-RS pairs or individual components of the invention can then be used in a host system's translation machinery, which results in an alkynyl amino acid being incorporated into a protein. International Publication Numbers WO 2004/094593, filed Apr. 16, 2004, entitled "EXPANDING THE EUKARYOTIC GENETIC CODE," and WO 2002/085923, entitled "IN VIVO INCORPORATION OF UNNATURAL AMINO ACIDS," describe this process, and are incorporated herein by reference. For example, when an O-tRNA/O-RS pair is introduced into a host, e.g., an *Escherichia coli* cell, the pair leads to the in vivo incorporation of an alkynyl amino acid such as para-propargyloxyphenylalanine into a protein in response to a selector codon. The para-propargyloxyphenylalanine that is added to the system is a synthetic amino acid, such as a derivative of a phenylalanine or tyrosine, which can be exogenously added to the growth medium. Optionally, the compositions of the present invention can be in an in vitro translation system, or in an in vivo system(s).

A cell of the invention provides the ability to synthesize proteins that comprise unnatural amino acids in large useful quantities. In one aspect, the composition optionally includes, e.g., at least 10 micrograms, at least 50 micrograms, at least 75 micrograms, at least 100 micrograms, at least 200 micrograms, at least 250 micrograms, at least 500 micrograms, at least 1 milligram, at least 10 milligrams or more of the protein that comprises an alkynyl amino acid, or an amount that can be achieved with in vivo protein production methods (details on recombinant protein production and purification are provided herein). In another aspect, the protein is optionally present in the composition at a concentration of, e.g., at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, e.g., a cell lysate, a buffer, a pharmaceutical buffer, or other liquid suspension (e.g., in a volume of, e.g., anywhere from about 1 mL to about 100 L). The production of large quantities (e.g., greater that that typically possible with other methods, e.g., in vitro translation) of a protein in a cell including at least one alkynyl amino acid is a feature of the invention.

The incorporation of an alkynyl amino acid can be done to, e.g., tailor changes in protein structure and/or function, e.g., to change size, acidity, nucleophilicity, hydrogen bonding, hydrophobicity, accessibility of protease target sites, target to a moiety (e.g., for a protein array), etc. Proteins that include an alkynyl amino acid can have enhanced or even entirely new catalytic or physical properties. For example, the following properties are optionally modified by inclusion of an alkynyl amino acid into a protein: toxicity, biodistribution, structural properties, spectroscopic properties, chemical and/or photochemical properties, catalytic ability, half-life (e.g., serum half-life), ability to react with other molecules, e.g., covalently or noncovalently, and the like. The compositions including proteins that include at least one alkynyl amino acid are useful for, e.g., novel therapeutics, diagnostics, catalytic enzymes, industrial enzymes, binding proteins (e.g., antibodies), and e.g., the study of protein structure and function. See, e.g., Dougherty, (2000) *Unnatural Amino Acids as Probes of Protein Structure and Function, Current Opinion in Chemical Biology,* 4:645-652.

In one aspect of the invention, a composition includes at least one protein with at least one, e.g., at least two, at least three, at least four, at least five, at least six, at least seven, at least eight, at least nine, or at least ten or more unnatural amino acids, e.g., alkynyl amino acids and/or other unnatural amino acids. The unnatural amino acids can be the same or different, e.g., there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is substituted with the alkynyl amino acid. For a given protein with more than one unnatural amino acids, the unnatural amino acids can be identical or different (e.g., the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Essentially any protein (or portion thereof) that includes an alkynyl amino acid (and any corresponding coding nucleic acid, e.g., which includes one or more selector codons) can be produced using the compositions and methods herein. No attempt is made to identify the hundreds of thousands of known proteins, any of which can be modified to include one or more unnatural amino acid, e.g., by tailoring any available mutation methods to include one or more appropriate selector codon in a relevant translation system. Common sequence repositories for known proteins include GenBank EMBL, DDBJ and the NCBI. Other repositories can easily be identified by searching the internet.

Typically, the proteins are, e.g., at least 60%, at least 70%, at least 75%, at least 80%, at least 90%, at least 95%, or at least 99% or more identical to any available protein (e.g., a therapeutic protein, a diagnostic protein, an industrial enzyme, or portion thereof, and the like), and they comprise one or more unnatural amino acid. Examples of therapeutic, diagnostic, and other proteins that can be modified to comprise one or more alkynyl amino acid can be found, but not limited to, those in International Publications WO 2004/094593, filed Apr. 16, 2004, entitled "Expanding the Eukaryotic Genetic Code;" and, WO 2002/085923, entitled "IN VIVO INCORPORATION OF UNNATURAL AMINO ACIDS." Examples of therapeutic, diagnostic, and other proteins that can be modified to comprise one or more alkynyl amino acids include, but are not limited to, e.g., Alpha-1 antitrypsin, Angiostatin, Antihemolytic factor, antibodies (further details on antibodies are found below), Apolipoprotein, Apoprotein, Atrial natriuretic factor, Atrial natriuretic polypeptide, Atrial peptides, C—X—C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, 1309, R83915, R91733, HCC1, T58847, D31065, T64262), CD40 ligand, C-kit Ligand, Collagen, Colony stimulating factor (CSF), Complement factor 5a, Complement inhibitor, Complement receptor 1, cytokines, (e.g., epithelial Neutrophil Activating Peptide-78, GROα/MGSA, GROβ, GROγ, MIP-1α, MIP-1δ, MCP-1), Epidermal Growth Factor (EGF), Erythropoietin ("EPO"), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog proteins (e.g., Sonic, Indian, Desert), Hemoglobin, Hepatocyte Growth Factor (HGF), Hirudin, Human serum albumin, Insulin, Insulin-like Growth Factor (IGF), interferons (e.g., IFN-α, IFN-β, IFN-γ), interleukins (e.g., IL-1, IL-2, IL-3, IL-4, IL-5, IL-6, IL-7, IL-8, IL-9, IL-10, IL-11, IL-12, etc.), Keratinocyte Growth Factor (KGF), Lactoferrin, leukemia inhibitory factor, Luciferase, Neurturin, Neutrophil inhibitory factor (NIF), oncostatin M, Osteogenic protein, Parathyroid hormone, PD-ECSF, PDGF, peptide hormones (e.g., Human Growth Hormone), Pleiotropin, Protein A, Protein G, Pyrogenic exotoxins A, B, and C, Relaxin, Renin, SCF, Soluble complement receptor I, Soluble I—CAM 1, Soluble interleukin receptors (IL-1,2,3,4, 5, 6, 7, 9, 10, 11, 12, 13, 14, 15), Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Superoxide dismutase (SOD), Toxic shock syndrome toxin (TSST-1), Thymosin alpha 1, Tissue plasminogen activator, Tumor necrosis factor beta (TNF beta), Tumor necrosis factor receptor (TNFR), Tumor necrosis factor-alpha (TNF alpha), Vascular Endothelial Growth Factor (VEGEF), Urokinase and many others.

One class of proteins that can be made using the compositions and methods for in vivo incorporation of alkynyl amino acids described herein includes transcriptional modulators or a portion thereof. Example transcriptional modulators include genes and transcriptional modulator proteins that modulate cell growth, differentiation, regulation, or the like. Transcriptional modulators are found in prokaryotes, viruses, and eukaryotes, including fungi, plants, yeasts, insects, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA.

One class of proteins of the invention (e.g., proteins with one or more alkynyl amino acids) include biologically active proteins such as cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4/VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Enzymes (e.g., industrial enzymes) or portions thereof with at least one alkynyl amino acid are also provided by the invention. Examples of enzymes include, but are not limited to, e.g., amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Many of these proteins are commercially available (See, e.g., the Sigma BioSciences 2002 catalogue and price list), and the corresponding protein sequences and genes and, typically, many variants thereof, are well-known (see, e.g., Genbank). Any of them can be modified by the insertion of one or more alkynyl amino acid according to the invention, e.g., to alter the protein with respect to one or more therapeutic, diagnostic or enzymatic properties of interest. Examples of therapeutically relevant properties include serum half-life, shelf half-life, stability, immunogenicity, therapeutic activity, detectability (e.g., by the inclusion of reporter groups (e.g., labels or label binding sites) in the unnatural amino acids, e.g., alkynyl amino acids), reduction of $LD_{50}$ or other side effects, ability to enter the body through the gastric tract (e.g., oral availability), or the like. Examples of diagnostic properties include shelf half-life, stability, diagnostic activity, detectability, or the like. Examples of relevant enzymatic properties include shelf half-life, stability, enzymatic activity, production capability, or the like.

A variety of other proteins can also be modified to include one or more alkynyl amino acid using compositions and methods of the invention. For example, the invention can include substituting one or more natural amino acids in one or more vaccine proteins with an alkynyl amino acid, e.g., in proteins from infectious fungi, e.g., *Aspergillus, Candida* species; bacteria, particularly *E. coli*, which serves a model for pathogenic bacteria, as well as medically important bacteria such as *Staphylococci* (e.g., aureus), or *Streptococci* (e.g., *pneumoniae*); protozoa such as sporozoa (e.g., *Plasmodia*), rhizopods (e.g., *Entamoeba*) and flagellates (Trypanosoma, *Leishmania, Trichomonas, Giardia*, etc.); viruses such as (+) RNA viruses (examples include Poxviruses e.g., vaccinia; Picornaviruses, e.g. polio; Togaviruses, e.g., *rubella*; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase are also suitable targets for alkynyl amino acid modification.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods well-known to one of skill in the art and described herein under "Mutagenesis and Other Molecular Biology Techniques" to include, e.g., one or more selector codon for the incorporation of an alkynyl amino acid. For example, a nucleic acid for a protein of interest is mutagenized to include one or more selector codon, providing for the insertion of the one or more alkynyl amino acids. The invention includes any such variant, e.g., mutant, versions of any protein, e.g., including at least one alkynyl amino acid. Similarly, the invention also includes corresponding nucleic acids, i.e., any nucleic acid with one or more selector codon that encodes one or more alkynyl amino acid.

To make a protein that includes an alkynyl amino acid, one can use host cells and organisms that are adapted for the in vivo incorporation of the alkynyl amino acid via orthogonal tRNA/RS pairs. Host cells are genetically engineered (e.g., transformed, transduced or transfected) with one or more vectors that express the orthogonal tRNA, the orthogonal tRNA synthetase, and a vector that encodes the protein to be derivatized. Each of these components can be on the same vector, or each can be on a separate vector, or two components can be on one vector and the third component on a second vector. The vector can be, for example, in the form of a plasmid, a bacterium, a virus, a naked polynucleotide, or a conjugated polynucleotide.

Defining Polypeptides by Immunoreactivity

Because the polypeptides of the invention provide a variety of new polypeptide sequences (e.g., polypeptides comprising alkynyl amino acids in the case of proteins synthesized in the translation systems herein, or, e.g., in the case of the novel synthetases, novel sequences of standard amino acids), the polypeptides also provide new structural features which can be recognized, e.g., in immunological assays. The generation of antisera, which specifically bind the polypeptides of the invention, as well as the polypeptides which are bound by such antisera, are a feature of the invention. The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, and single chain antibodies, and the like. Fragments of immunoglobulins, including Fab fragments and fragments produced by an expression library, including phage display, are also included in the term "antibody" as used herein. See, e.g., Paul, *Fundamental Immunology*, 4th Ed., 1999, Raven Press, New York, for antibody structure and terminology.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual*, Cold Spring Harbor Publications, New York, for a standard description of antibody generation, immunoassay formats and conditions that can be used to determine specific immunoreactivity. Additional details on proteins, antibodies, antisera, etc. can be found in International Publication Numbers WO 2004/094593, entitled "EXPANDING THE EUKARYOTIC GENETIC CODE;" WO 2002/085923, entitled "IN VIVO INCORPORATION OF UNNATURAL AMINO ACIDS;" WO 2004/035605, entitled "GLYCOPROTEIN SYNTHESIS;" and WO 2004/058946, entitled "PROTEIN ARRAYS."

Use of O-tRNA and O-RS and O-tRNA/O-RS Pairs

The compositions of the invention and compositions made by the methods of the invention optionally are in a cell. The O-tRNA/O-RS pairs or individual components of the invention can then be used in a host system's translation machinery, which results in an alkynyl amino acid being incorporated into a protein. International Publication Number WO 2002/085923 by Schultz, et al., entitled "IN VIVO INCORPORATION OF UNNATURAL AMINO ACIDS," describes this process and is incorporated herein by reference. For example, when an O-tRNA/O-RS pair is introduced into a host, e.g., *Escherichia coli*, the pair leads to the in vivo incorporation of an alkynyl amino acid, which can be exogenously added to the growth medium, into a protein, e.g., a myoglobin test protein or a therapeutic protein, in response to a selector codon, e.g., an amber nonsense codon. Optionally, the compositions of the invention can be in an in vitro translation system, or in a cellular in vivo system(s). Proteins with the alkynyl amino acid can be used in any of a wide range of applications. Most notably, the alkynyl moiety incorporated into a protein can serve as a target for any of a wide range of modifications, for example, crosslinking with other proteins, with small molecules such as labels or dyes and/or biomolecules. With these modifications, incorporation of the alkynyl amino acid can result in improved therapeutic proteins and can be used to alter or improve the catalytic function of enzymes. In some aspects, the incorporation and subsequent modification of an alkynyl amino acid in a protein can facilitate studies on protein structure, interactions with other proteins, and the like.

Kits

Kits are also a feature of the invention. For example, a kit for producing a protein that comprises at least one alkynyl amino acid in a cell is provided, where the kit includes a container containing a polynucleotide sequence encoding an O-tRNA, and/or an O-tRNA, and/or a polynucleotide sequence encoding an O-RS, and/or an O-RS. In one embodiment, the kit further includes an alkynyl amino acid such as para-propargyloxyphenylalanine. In another embodiment, the kit further comprises instructional materials for producing the protein.

EXAMPLES

The following examples are offered to illustrate, but not to limit the claimed invention. One of skill will recognize a variety of non-critical parameters that may be altered without departing from the scope of the claimed invention.

Example 1

Evolution of an Orthogonal tRNA/Synthetase Pair for the Incorporation of an Alkynyl Amino Acid Into Proteins In *E. coli*

By evolving the specificity of orthogonal tRNA-synthetase pairs, we have selectively and efficiently incorporated a number of unnatural amino acids into proteins in response to nonsense and frameshift codons in both prokaryotes and eukaryotes (Anderson et al. (2004) *Proc. Natl. Acad. Sci. U.S.A.,* 101:7566; Alfonta et al. (2003) *J. Am. Chem. Soc.,* 125:14662; Wang et al. (2003) *Proc. Natl. Acad. Sci. U.S.A.,* 100:56; Chin et al. (2003) *Science* 301:964; Chin et al. (2002) *Proc. Natl. Acad. Sci.,* 99:11020; and Wang et al. (2001) *Science* 292:498). The present invention provides compositions and methods for the biosynthetic incorporation of reactive alkynyl-moiety containing amino acids into proteins using *E. coli* translation machinery. The biosynthesis using *E. coli* translation components can occur in vivo (e.g., in the *E. coli* cell) or in vitro using crude cell extracts or purified translation components. The alkynyl group that is incorporated into proteins is readily and specifically conjugated with azido-containing moieties, thereby providing a useful target for protein modification/manipulation.

The chemistry of alkynyl and azido groups (shown in FIG. 1B) is completely orthogonal to the chemistries of all endogenous functional groups present in proteins. An example of their unique reactivity is the irreversible formation of triazoles by a [3+2]cycloaddition (see, FIG. 1B; and Padwa, In *Comprehensive Organic Synthesis*; [Trost, B. M., Ed.] Pergamon: Oxford, 1991, Vol. 4, p 1069; Huisgen, In 1,3-*Dipolar Cycloaddition Chemistry*, [Padwa, A., Ed.] Wiley: New York, 1984; p 1). When this reaction is conducted in the presence of copper(I) at room temperature in aqueous media (conditions mild enough for modifying biological samples), it proceeds in a completely regioselective fashion (Rostovtsev et al. (2002) *Angew. Chem. Int. Ed.,* 41:2596) and can be used to selectively modify proteins into which alkynyl and azido functional groups have been introduced (Deiters et al. (2003) *J. Am. Chem. Soc.,* 125:11782; Wang et al. (2003) *J. Am. Chem. Soc.,* 125:3192; Link and Tirrell (2003) *J. Am. Chem. Soc.,* 125:11164).

The invention described herein provides orthogonal tRNA/tRNA-synthetase pairs derived from *Methanococcus jannaschii* components that selectively incorporate the alkynyl amino acid para-propargyloxyphenylalanine (abbreviated pPRO-Phe; also known as 2-amino-3-[4-(prop-2-ynyloxy)phenyl]-propionic acid according to IUPAC nomenclature; structure shown in FIG. 1A, and is assigned chemical structure designation 1) in an *E. coli* host system. The present study demonstrates that pPRO-Phe is selectively incorporated into proteins expressed in *E. coli* using the novel orthogonal tRNA and tRNA synthetase reagents provided herein.

We report herein the evolution of an orthogonal tRNA/synthetase pair derived from a *M. jannaschii* tyrosyl tRNA/tRNA-synthetase pair (MjTyrRS/$tRNA_{CUA}$), where the orthogonal pair has no affinity or very low affinity for any of the common (i.e., naturally occurring) amino acids. The derived orthogonal tRNA synthetase selectively charges the amber suppressor $tRNA_{CUA}$ with pPRO-Phe, and furthermore, the aminoacylated suppressor tRNA (i.e., the "charged" tRNA) is used as a substrate by endogenous *E. coli* translation apparatus to incorporate pPRO-Phe in response to a TAG amber stop codon (a selector codon) encountered in a transcript. The orthogonality (Steer and Schimmel (1999) *Biol. Chem.,* 274:35601) of this tRNA/synthetase pair ensures that neither the tRNA nor the synthetase cross reacts with endogenous *E. coli* tRNAs or synthetases and that the unnatural amino acid gets delivered only in response to an amber nonsense codon, TAG.

A library of ~$10^7$ different *M. jannaschii* tyrosyl tRNA-synthetases was generated by mutagenesis of the wild-type *M. jannaschii* tyrosyl tRNA-synthetase. To create the MjTyrRS library the five positions targeted for mutation were first converted to alanine codons. The MjTyrRS gene was expressed under the control of *E. coli* GlnRS promoter and terminator in plasmid pBK-JYRS, a pBR322 derived plasmid with kanamycin resistance. Residues $Tyr^{32}$, $Glu^{107}$, $Asp^{158}$, $Ile^{159}$, and $Leu^{162}$ were substituted with Ala by site-directed mutagenesis to afford plasmid pBK-JYA5. Eight oligonucleotides with NNK (N=A+T+G+C and K=G+T) at the mutation sites were used for PCR amplification of the $Ala_5$ MjTyrRS mutant (pBK-JYA5) and ligated back into the Nde I-Pst I digested pBK-JYA5 to generate the MjTyrRS library. The ligated vectors were transformed into *E. coli* DH10B competent cells to yield a library of $1.6\times10^9$ colony forming units.

The polynucleotide and amino acid sequences of the wild-type *M. jannaschii* tyrosyl tRNA-synthetase molecule are shown in FIG. 2, and are also provided in SEQ ID NOS: 3 and 2, respectively. The mutagenesis consisted of randomizing five active site residues (Tyr32, Glu107, Asp158, Ile159, and Leu162), based on a crystal structure of the homologous tyrosyl tRNA-synthetase from *Bacillus stearothermophilus.*

Following mutagenesis, the pool of synthetases was then passed through positive and negative rounds of selection. The positive selection is based on suppression of an amber stop codon at a permissive site (Asp112) in the chloramphenicol acetyltransferase (CAT) gene. When *E. coli* cells harboring the MjTyrRS mutant library, the mutated CAT gene and a coexpressed Mj amber suppressor $tRNA_{CUA}$ were grown on minimal media in the presence of pPRO-Phe (1 mM) and chloramphenicol (80 μg/mL), the only surviving cells are those cells that contain a mutant synthetase that aminoacylates the $tRNA_{CUA}$ with either an endogenous amino acid or pPRO-Phe. The synthetase library genes were then transformed into cells containing a mutated gene encoding the toxic protein barnase, which has three amber mutations at permissive sites (Gln2, Asp44, Gly65). The vector carrying the barnase reporter also contained the suppressor tRNA. Growth of these cells in the absence of pPRO-Phe selected against synthetases capable of accepting endogenous amino acids as a substrate. After three rounds of selection, 96 clones were screened for growth rate dependence on the presence or absence of pPRO-Phe, and eight candidate clones were identified and sequenced. The amino acid substitutions observed in these isolated clones are shown in FIG. 3. The polynucleotide and amino acid sequences of the eight clones is also provided in SEQ ID NOS: 4 through 19.

Consensus trends in the amino acid substitutions in the eight mutant O-RS clones are observed. A preponderance of the following amino acids was found in the binding pocket of most of the clones: Ala32, Pro107/Gln107, Ala158, Ile159, and Ala162/Pro162. The mutations Tyr32→Ala32 and Asp158→Ala158 may result in the loss of hydrogen bonds between Tyr32, Asp158 and the natural substrate tyrosine, thus disfavoring its binding. The occurrence of small and mostly hydrophobic side chains might be expected to facilitate binding of pPRO-Phe. An additional Leu110→Phe110 mutation was also observed in one of the clones (pPRO-PheRS-1).

The synthetase pPRO-PheRS-1 was selected for further characterization. This synthetase confers chloramphenicol resistance on *E. coli* with $IC_{50}$ values of 110 and 5 μg/mL in the presence and absence of pPRO-Phe, respectively. The large difference between the chloramphenicol resistance with and without pPRO-Phe suggests a substantial in vivo specificity of pPRO-PheRS-1 for the unnatural amino acid pRPO-Phe.

Example 2

Site-Specific Incorporation of an Alkynyl Amino Acid Into a Protein In *E. Coli*

The mutant amber suppressor $tRNA_{CUA}$ and the pPRO-PheRS-1 orthogonal pair were used in *E. coli* to selectively incorporate pPRO-Phe into sperm whale myoglobin, a monomeric 153-residue heme-containing protein that has been the focus of a number of structural, mechanistic, and protein folding studies (Reedy and Gibney (2004) *Chem. Rev.,* 104: 617, and references therein; Uzawa et al. (2004) *Proc. Natl. Acad. Sci. U.S.A.,* 101:1171, and references therein; Wright, and Baldwin in *Frontiers in Molecular Biology: Mechanisms of Protein Folding*, [Pain, R., ed.] Oxford University Press, London, 2000, pp. 309).

To produce alkynyl-modified myoglobin, the fourth codon of the myoglobin open reading frame (Ser4) was mutated to TAG (amber stop) and a C-terminal 6×His (hexahistidine) tag was added to the open reading frame. To express the mutant protein, plasmid pBAD/JYAMB-4TAG (which encodes the mutant sperm whale myoglobin gene with an arabinose promoter and a rrnB terminator; the tyrosyl $tRNA_{CUA}$ on a 1 pp promoter and a rrnC terminator; and a tetracycline resistance marker) was co-transformed with a pBK vector (encoding the mutant synthetase and a kanamycin resistance gene) into DH10B *E. coli*. Cells were amplified in Luria-Bertani media (5 mL) supplemented with tetracycline (25 mg/L) and kanamycin (30 mg/L), washed with phosphate buffer, and used to inoculate 500 mL of liquid glycerol minimal media (supplemented with 0.3 mM leucine) containing the appropriate antibiotics, pPRO-Phe (1 mM), and arabinose (0.002%). Cells were grown to saturation and then harvested by centrifugation. The protein was purified using Ni-affinity chromatography with a yield of 2 mg/L after purification by the Ni-affinity chromatography and estimated at 90% homogeneous by SDS-PAGE/Gelcode® Blue staining (Pierce Biotechnology, Inc.). A total yield of ~1 mg of mutant myoglobin was obtained.

Figure 4:
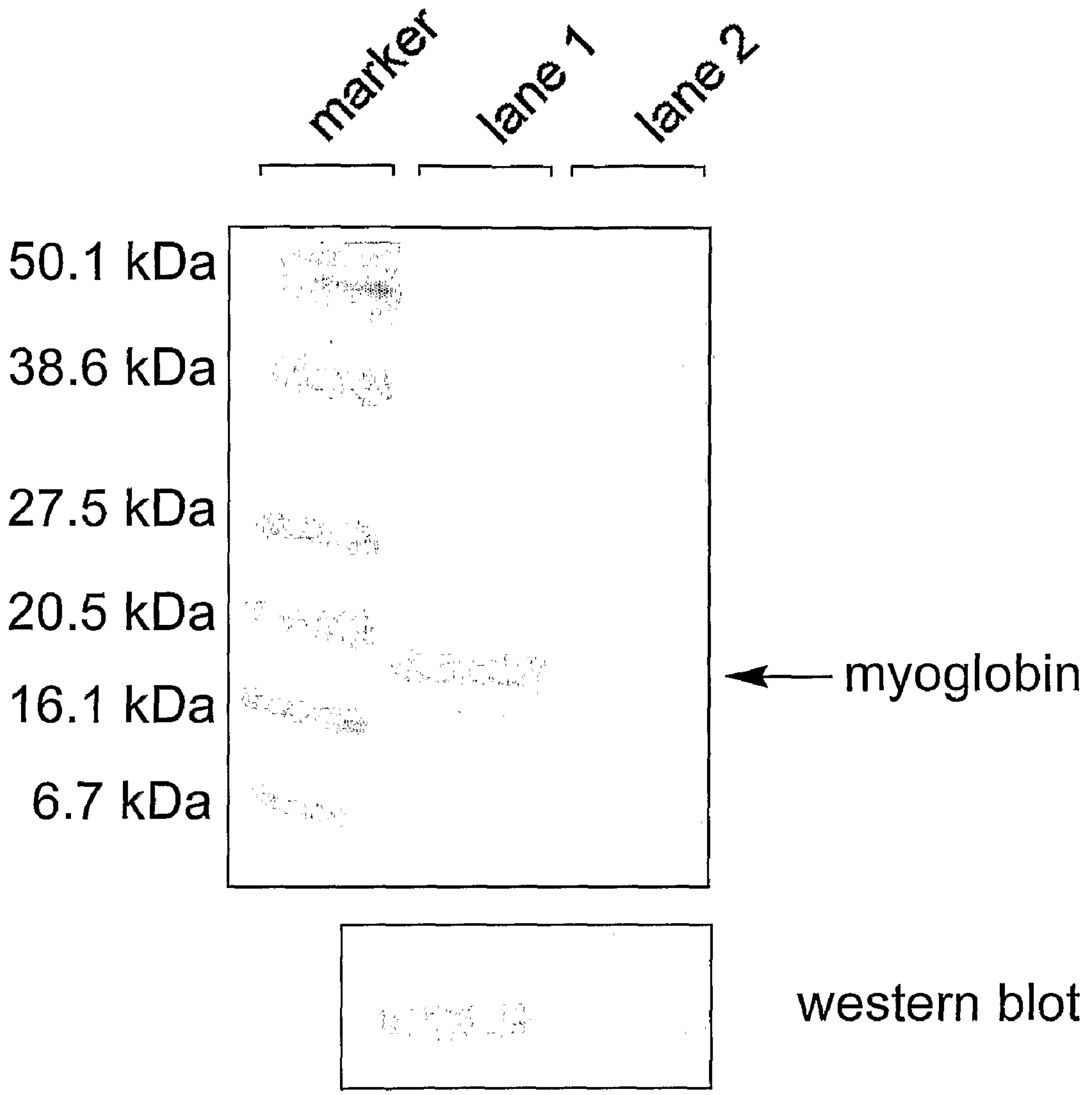
FIG. 4 provides a Gelcode® Blue (Pierce Biotechnology, Inc.)-stained SDS-PAGE gel of purified Ser4→pPRO-Phe4 mutant myoglobin. Lane 1 contains protein expressed in *E. coli* cultured in minimal media in the presence of para-propargyloxyphenylalanine (pPRO-Phe); Lane 2 contains a protein sample generated in the absence of pPRO-Phe. The bottom panel shows a western blot of the same sample materials using an anti-His6 antibody to detect the hexahistidine tag at the C-terminus of myoglobin.

The protein thus produced is visualized in FIG. 4, lane 1, using both Gelcode® Blue staining and Western blotting using an anti-His6 antibody. In the absence of pPRO-Phe, no myoglobin was visible after staining or Western blotting (using an anti-His6 antibody), indicating a high selectivity of the evolved synthetase (see, FIG. 4, lane 2).

Example 3

Mass Spectrometry Confirmation of Alkynyl Amino Acid Incorporation Into a Protein In *E. coli*

To further confirm the identity of the amino acid incorporated at the site of an amber stop codon in mutant myoglobin, a tryptic digest of the myoglobin was subjected to liquid chromatography/tandem mass spectrometry. The mutant myoglobin used in this experiment contained an engineered amber stop codon at position 74. The incorporation of pPRO-Phe at this position (pPRO-Phe74) was tested 74 mutation. The myoglobin-74TAG mutant was used instead of the previously described Ser4→TAG(amber stop) due to improved properties for LC MS/MS analysis.

Following eubacterial expression, the myoglobin 74TAG was purified using nickel affinity column. Protein bands were visualized by Gelcode® Blue staining of an SDS-PAGE gel. Gel bands corresponding mutant myoglobin were excised from the polyacrylamide gel, sliced into 1.5-mm cubes and subjected to trypsin hydrolysis essentially as described (Shevchenko et al. (1996) *Anal. Chem.,* 68:850-858).

Tryptic peptides containing the unnatural amino acid were analyzed by nanoflow reversed-phase HPLC/μESI/MS with an LCQ ion trap mass spectrometer. Liquid chromatography tandem mass spectrometry (LC-MS/MS) analysis was performed on a Finnigan LCQ Deca ion trap mass spectrometer (Thermo Finnigan) fitted with a Nanospray HPLC (Agilent 1100 series).

Figure 5:
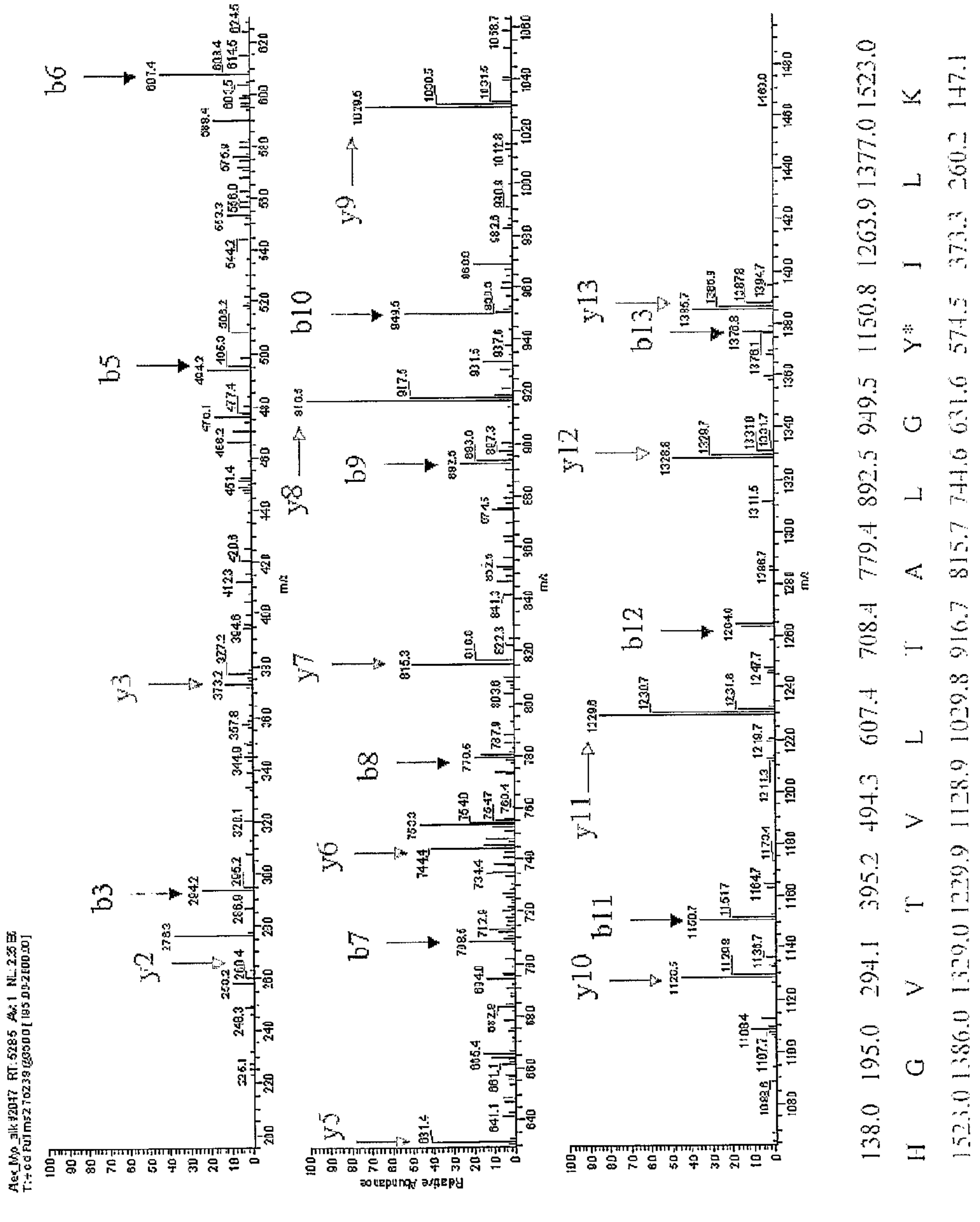
FIG. 5 provides a tandem mass spectrum of the tryptic peptide HGVTVLTALGY*ILK containing the alkynyl unnatural amino acid (denoted Y*) shown with their expected fragment ion masses. Arrows indicates observed b and y ions series for the peptide.

The precursor ions corresponding to the singly and doubly charged ions of the peptide HGVTVLTALGY*ILK (SEQ ID NO: X) containing the unnatural amino acid (denoted Y*) were separated and fragmented with an ion trap mass spectrometer. The results of this analysis are provided in FIG. 5. The fragment ion masses could be unambiguously assigned, confirming the site-specific incorporation of pPRO-Phe. The LC MS/MS runs did not suggest incorporation of any natural amino acid at this position, confirming the high selectivity of the evolved synthetase.

Example 4

Derivatization of a Protein Containing an Alkynyl Amino Acid by [3+2] Cycloaddition Proteins containing alkynyl functional groups can be effectively targeted for modification by use of a [3+2]cycloaddition reaction. The present EXAMPLE describes the derivatization of the alkynyl myoglobin with two different azido-containing dye molecules. The mutant myoglobin used in this example incorporated pPRO-Phe at the fourth codon (Ser4→pPRO-Phe4), as described in EXAMPLE 1.

Figure 7A:
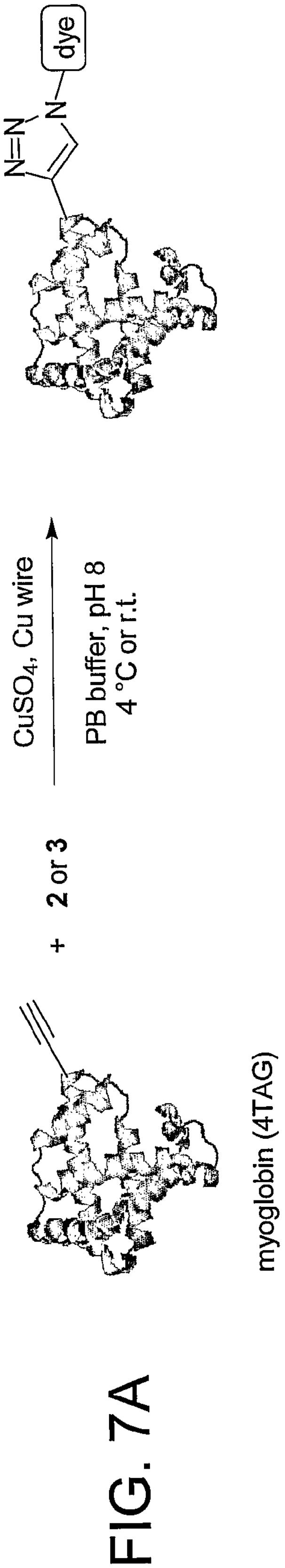
FIG. 7A provides the generalized reaction chemistry of the irreversible formation of a triazole from the [3+2]cycloaddition reaction between the mutant myoglobin containing an alkynyl amino acid at the site of the engineered amber codon (4TAG) and an azido-functionalized dye (as provided in FIGS. 6A and 6B).

The Ser4→pPRO-Phe4 myoglobin was produced in *E. coli* as described in EXAMPLE 2, then derivatized with the azido functionalized dyes 2 or 3, containing the dansyl and fluoresceine fluorophore, respectively (as shown in FIGS. 6A and 6B; see also, Deiters et al. (2003) *J. Am. Chem. Soc.,* 125:11782; Wang et al. (2003) *J. Am. Chem. Soc.,* 125:3192; Link and Tirrell (2003) *J. Am. Chem. Soc.,* 125:11164). The [3+2] cycloaddition derivatization reaction is illustrated in FIG. 7A.

For the cycloaddition reaction, 1 μL of $CuSO_4$ (50 mM stock solution in $H_2O$; 1 mM in final reaction volume), 2 μL of dye 2 or 3 (50 mM in EtOH), 2 μL of tris(1-benzyl-1H-[1,2,3]triazol-4-ylmethyl)amine (50 mM in DMSO), and 1 mg Cu wire or 1 μL tris(carboxyethyl)phosphine (100 mM in $H_2O$) (as reducing agents) were added to 45 μL of purified mutant myoglobin (~0.5 mg/mL) in 0.1 M phosphate buffer (pH=8). After 8 h at room temperature or overnight at 4° C., 450 μL $H_2O$ were added and the mixture was spun through a dialysis membrane (10 kDa cut off). After washing the supernatant with 2×500 μL phosphate buffer by centrifugation, the solution was brought to a volume of 50 μL.

Figure 7B:
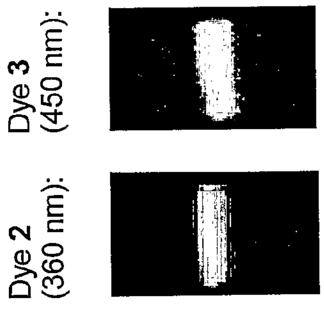
FIG. 7B provides a fluorescence gel imaging under UV irradiation of the resolved labeled myoglobin, where the [3+2]cycloaddition reaction covalently attached either Dye 2 or Dye 3.

The use of Cu-wire or tris(carboxyethyl)phosphine (2 mM) as reducing agents generally led to a similar labeling efficiency. In contrast to previous observations (Wang et al. (2003) *J. Am. Chem. Soc.,* 125:3192), the presence or absence of the ligand tris(1-benzyl-1H-[1,2,3]triazol-4-ylmethyl) amine did not have a substantial influence on the outcome of these reactions. A sample of 20 μL of the fluorescently labeled proteins (Blake (2001) *Curr. Opin. Pharmacol.,* 1:533; Wouters et al. (2001) *Trends in Cell Biology* 11:203; Zacharias et al. (2000) *Curr. Opin. Neurobiol.,* 10:416) were then analyzed by SDS-PAGE and in-gel imaged. Mutant myoglobin modified with the dansyl dye 2 ($\lambda_{ex}$=337 nm, $\lambda_{em}$=506 nm) was in-gel imaged at 360±30 nm using an Eagle Eye densitometer (Stratagene). Attachment of the fluoresceine dye 3 ($\lambda_{ex}$=495 nm, $\lambda_{em}$=516 nm) was visualized at 450±30 nm with a Storm Phosphorimager (Molecular Dynamics). The results of this fluorescent imaging is shown in FIG. 7B. The mutant myoglobin is effectively labeled by both dyes 2 and 3. The labeling efficiency was ~75% as determined by comparison of the $A_{280}/A_{495}$ values for myoglobin labeled with 3 (see, Wang et al. (2003) *J. Am. Chem. Soc.,* 125:3192). The selectivity of this bioconjugation was verified by the fact that no reaction between wild type myoglobin and 2 or 3 was observed (results not shown).

The description provided herein demonstrates that an alkynyl amino acid, e.g., para-propargyloxyphenylalanine, can be efficiently and selectively incorporated into proteins in an organism, e.g., *E. coli*. These amino acids can then be chemically targeted within the protein for conjugation, e.g., by [3+2]cycloaddition using azido moieties, and furthermore, where this targeted modification is highly specific and regioselective. The ability to incorporate alkynyl amino acids site-specifically into proteins provides a valuable tool in the study of any protein where protein conjugation or modification is desired.

Example 5

Synthesis of the Unnatural Alkynyl Amino Acid para-Propargyloxyphenylalanine The unnatural alkynyl amino acid para-propargyloxyphenylalanine (abbreviated pPRO-Phe; see FIG. 1A, compound 1) was synthesized from commercially available N-Boc-tyrosine in three steps (see, Deiters et al. (2003) *J. Am. Chem. Soc.,* 125:11782; Wang et al. (2003) *J. Am. Chem. Soc.,* 125:3192; Link and Tirrell (2003) *J. Am. Chem. Soc.,* 125:11164) with an overall yield of 81%.

Step 1

N-tert-butoxycarbonyl-tyrosine (2 g, 7 mmol, 1 equiv.) and $K_2CO_3$ (3 g, 21 mmol, 3 equiv.) were suspended in anhydrous DMF (15 mL). Propargyl bromide (2.1 mL, 21 mmol, 3 equiv., 80% solution in toluene) was slowly added and the reaction mixture was stirred for 18 h at room temperature. Water (75 mL) and $Et_2O$ (50 mL) were added, the layers were separated and the aqueous phase was extracted with $Et_2O$ (2×50 mL). The combined organic layers were dried ($MgSO_4$) and the solvent was removed under reduced pressure. The product (4), shown and named below, was obtained as a yellow oil (2.3 g, 91%) and used in the next step without further purification.

(compound 4)

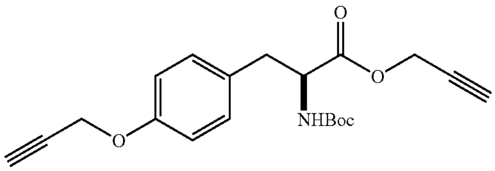

2-tert-butoxycarbonylamino-3-[4-(prop-2-ynyloxy)phenyl]-propionic acid propargyl ester Step 2

Acetyl chloride (7 mL) was added carefully to methanol (60 mL) at 0° C. to give a 5 M solution of anhydrous HCl in MeOH. The product of the previous step (compound 4; 2 g, 5.6 mmol) was added and the reaction was stirred for 4 h while it was allowed to warm to ambient temperature. After removing the volatiles under reduced pressure a yellowish solid (compound 5, shown and named below; 1.6 g, 98%) was obtained which was directly used in the next step.

(compound 5)

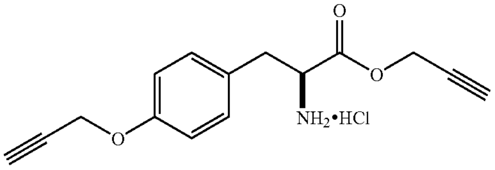

2-amino-3-[4-(prop-2-ynyloxy)phenyl]-propionic acid propargyl ester

Step 3

The propargyl ester (1.6 g, 5.5 mmol) from the previous step (5) was dissolved in a mixture of aqueous 2N NaOH (14 mL) and MeOH (10 mL). After stirring for 1.5 h at room temperature, the pH was adjusted to 7 by adding concentrated HCl. Water (20 mL) was added and the mixture was kept at 4° C. over night. The precipitate was filtered, washed with ice-cold $H_2O$, and dried under vacuum yielding 1.23 g (90%) of pPRO-Phe (1) as a white solid. $^1$H NMR (400 Mz, $D_2O$; as the potassium salt in $D_2O$) δ 7.20 (d, J=8.8 Hz, 2H), 6.99 (d, J=8.8 Hz, 2H), 4.75 (s, 2H), 3.50 (dd, J=5.6, 7.2 Hz, 1H), 2.95 (dd, J=5.6, 13.6 Hz, 1H), 2.82 (dd, J=7.2, 13.6 Hz, 1H); $^{13}$C NMR (100 MHz, $D_2O$) δ 181.3, 164.9, 155.6, 131.4, 130.7, 115.3, 57.3, 56.1, 39.3; HRMS (CI) m/z 220.0969 [$C_{12}H_{13}NO_3$ (M+1) requires 220.0968].

(compound 1)

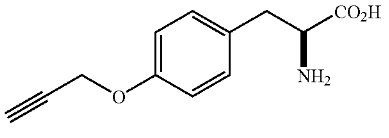

para-propargyloxyphenylalanine

Example 6

Synthesis of the Azido Dye 2

The azido Dye 2 (see FIG. 6A; compound 2) was synthesized according to the following protocol. 3-Azidopropylamine (371 mg, 3.71 mmol, 3 equiv.) (synthesized according to Carboni et al. (1993) Org. Chem., 58:3736-3741) was added to a solution of dansyl chloride (500 mg, 1.85 mmol, 1 equiv.) and triethylamine (258 μL, 1.85 mmol, 1 equiv.) in $CH_2Cl_2$ (10 mL) at 0° C. After stirring for 1 h, the reaction mixture was warmed to room temperature and stirred for an additional hour. The volatiles were removed in vacuo and the crude product was purified by chromatography on silica gel ($Et_2O$/hexanes=1:1) yielding 2 (548 mg, 89%) as a yellow oil. $^1$H NMR (400 MHz, $CDCl_3$) δ 8.55 (d, J=8.4 Hz, 1H), 8.29 (d, J=8.8 Hz, 1H), 8.23 (dd, J=1.2, 7.2 Hz, 11), 7.56-7.49 (comp, 2H), 7.18 (d, J=7.6 Hz, 1H), 5.24 (br s, 1H), 3.21 (t, J=6.4 Hz, 2H), 2.95 (dt, J=6.4 Hz, 2H), 2.89 (s, 6H), 1.62 (quin, J=6.4 Hz, 2H); $^{13}$C NMR (100 MHz, $CDCl_3$) δ 134.3, 130.4, 129.7, 129.4, 128.4, 123.3, 118.8, 115.3, 48.6, 45.4, 40.6, 28.7 (not all signals of quaternary carbon atoms are visible in the $^{13}$C NMR spectrum); HRMS (CI) m/z 334.1336 [$C_{15}H_{20}N_5O_2S$ (M+1) requires 334.1332].

(compound 2)

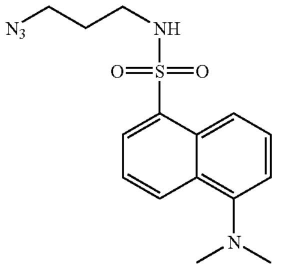

Azido Dye 2

Example 7

Synthesis of the Azido Dye 3

The azido Dye 3 (see FIG. 6B; compound 3) was synthesized according to the following protocol. EDCI (83 mg, 0.43 mmol, 1 equiv.) was added to a solution of fluoresceinamine (150 mg, 0.43 mmol, 1 equiv.) and 4-(3-azidopropylcarbamoyl)-butyric acid (92 mg, 0.43, 1 equiv.) in pyridine (2 mL) at room temperature. (The 4-(3-azidopropylcarbamoyl)-butyric acid was synthesized by reacting 3-azidopropylamine with glutaric acid anhydride.) The suspension was stirred over night and the reaction mixture was poured in $H_2O$ (15 mL). The solution was acidified (pH<2) by adding concentrated HCl. After stirring for 1 h, the precipitate was filtered off, washed with 1N HCl (3×3 mL) and was dissolved in a small amount of EtOAc. Addition of hexanes led to the precipitation of 3 as orange crystals, which were collected and dried under vacuum (200 mg, 86%). $^1$H NMR (400 MHz, $CD_3OD$) δ 8.65 (s, 1H), 8.15 (d, J=8.4 Hz, 1H), 7.61-7.51 (comp, 2H), 7.40 (d, J=8.4 Hz, 1H), 7.35 (br s, 21H), 7.22-7.14 (comp, 21H), 6.85-6.56 (comp, 3H), 3.40-3.24 (comp, 4H), 2.54 (t, J=7.2 Hz, 2H), 2.39-2.30 (comp, 2H), 2.10-1.99 (comp, 2 H), 1.82-1.72 (comp, 2H); $^{13}$C NMR (100 MHz, $CD_3OD$) δ 175.7, 174.4, 172.4, 167.9, 160.8, 143.0, 134.3, 132.9, 131.8, 129.6, 124.4, 123.3, 121.1, 118.5 103.5, 50.2, 38.0, 37.2, 36.2, 29.8, 22.9; 4 HRMS (CI) m/z 544.1835 [$C_{28}H_{25}N_5O_7$ (M+1) requires 544.1827].

(compound 3)

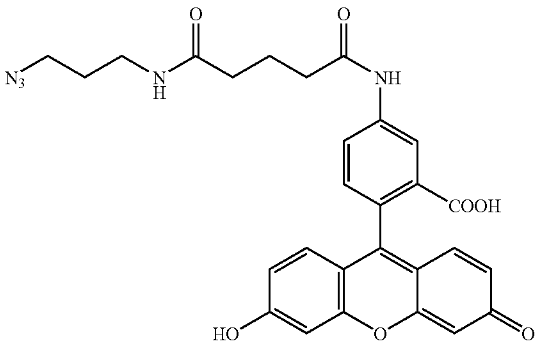

Azido Dye 3

Example 8

Exemplary O-RS's and O-tRNA's for the Incorporation of Alkynyl Amino Acids in *E. coli*

An exemplary O-tRNA comprises SEQ ID NO.: 1 (see EXAMPLE 9, Table 4). Example O-RSs include the amino acid sequences provided in SEQ ID NOS: 4, 6, 8, 10, 12, 14, 16 and 18 (see FIG. 3 and EXAMPLE 9, Table 4).

Examples of polynucleotides that encode O-RSs or portions thereof include any polynucleotide that encodes an amino acid sequence comprising SEQ ID NOS: 4, 6, 8, 10, 12, 14, 16 and 18. For example, polynucleotides provided in SEQ ID NOS: 5, 7, 9, 11, 13, 15, 17 and 19 encode exemplary O-RSs.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

Example 9

Nucleotide and Amino Acid Sequences

This EXAMPLE provides nucleotide and amino acid sequences for various polynucleotides and polypeptides, respectively. The sequences provided in TABLE 4 below is meant to provide examples only, and it is not intended that invention be limited in any way to the sequences provided TABLE 4.

TABLE 4

| SEQ ID NO: | Description | SEQUENCE |
|---|---|---|
| 1 | mutRNA$^{Tyr}_{CUA}$ | CCGGCGGUAGUUCAG<br>CAGGGCAGAACGGCG<br>GACUCUAAAUCCGCA<br>UGGCGCUGGUUCAAA<br>UCCGGCCCGCCGGAC<br>CA |
| 2 | Wild-type *Methanococcus jannaschii* tyrosyl-tRNA synthetase (MjTyrRS) amino acid sequence | MDEFEMIKRNTSEII<br>SEEELREVLKKDEKS<br>AYIGFEPSGKIHLGH<br>YLQIKKMIDLQNAGF<br>DIIILLADLHAYLNQ<br>KGELDIRKIGDYNKK<br>VFEAMGLKAKYVYGS<br>EFQLDKDYTLNVYRL<br>ALKTTLKRARRSMEL<br>IAREDENPKVAEVIY<br>PIMQVNDIHYLGVDV<br>AVGGMEQRKIHMLAR<br>ELLPKKVVCIHNPVL<br>TGLDGEGKMSSSKGF<br>IAVDDSPEEIRAKIK<br>KAYCPAGVVEGNPIM<br>EIAKYFLEYPLTIKR<br>PEKFGGDLTVNSYEE<br>LESLFKNKELHPMDL<br>KNAVAEELIKILEPI<br>RKRL |
| 3 | Wild-type *Methanococcus jannaschii* tyrosol-tRNA synthetase (MjTyrRS) nucleotide sequence | ATGGACGAATTTGAA<br>ATGATAAAGAGAAAC<br>ACATCTGAAATTATC<br>AGCGAGGAAGAGTTA<br>AGAGAGGTTTTAAAA<br>AAAGATGAAAAATCT<br>GCTTACATAGGTTTT<br>GAACCAAGTGGTAAA<br>ATACATTTAGGGCAT<br>TATCTCCAAATAAAA<br>AAGATGATTGATTTA<br>CAAAATGCTGGATTT<br>GATATAATTATATTG<br>TTGGCTGATTTACAC |

TABLE 4-continued

| SEQ ID NO: | Description | SEQUENCE |
|---|---|---|
| | | GCCTATTTAAACCAG<br>AAAGGAGAGTTGGAT<br>GAGATTAGAAAAATA<br>GGAGATTATAACAAA<br>AAAGTTTTTGAAGCA<br>ATGGGGTTAAAGGCA<br>AAATATGTTTATGGA<br>AGTGAATTCCAGCTT<br>GATAAGGATTATACA<br>CTGAATGTCTATAGA<br>TTGGCTTTAAAAACT<br>ACCTTAAAAAGAGCA<br>AGAAGGAGTATGGAA<br>CTTATAGCAAGAGAG<br>GATGAAAATCCAAAG<br>GTTGCTGAAGTTATC<br>TATCCAATAATGCAG<br>GTTAATGATATTCAT<br>TATTTAGGCGTTGAT<br>GTTGCAGTTGGAGGG<br>ATGGAGCAGAGAAAA<br>ATACACATGTTAGCA<br>AGGGAGCTTTTACCA<br>AAAAAGGTTGTTTGT<br>ATTCACAACCCTGTC<br>TTAACGGGTTTGGAT<br>GGAGAAGGAAAGATG<br>AGTTCTTCAAAAGGG<br>AATTTTATAGCTGTT<br>GATGACTCTCCAGAA<br>GAGATTAGGGCTAAG<br>ATAAAGAAAGCATAC<br>TGCCCAGCTGGAGTT<br>GTTGAAGGAAATCCA<br>ATAATGGAGATAGCT<br>AAATACTTCCTTGAA<br>TATCCTTTAACCATA<br>AAAAGGCCAGAAAAA<br>TTTGGTGGAGATTTG<br>ACAGTTAATAGCTAT<br>GAGGAGTTAGAGAGT<br>TTATTTAAAAATAAG<br>GAATTGCATCCAATG<br>GATTTAAAAAATGCT<br>GTAGCTGAAGAACTT<br>ATAAAGATTTTAGAG<br>CCAATTAGAAAGAGA<br>TTA |
| 4 | pPRO-PheRS-1; para-propargyloxyphenylalanine aminoacyl-tRNA synthetase isolate-1 amino acid sequence (derived from wild-type *Methanococcus jannaschii* tyrosyl tRNA-synthetase), having amino acid changes:<br>Tyr32→Ala32<br>Glu107→Pro107<br>Leu110→Phe110<br>Asp158→Ala158<br>Leu162→Ala162 | MDEFEMIKRNTSEII<br>SEEELREVLKKDEKS<br>AAIGFEPSGKIHLGH<br>YLQIKKMIDLQNAGF<br>DIIILLADLHAYLNQ<br>KGELDEIRKIGDYNK<br>KVFEAMGLKAKYVYG<br>SPFQFDKDYTLNVYR<br>LALKTTLKRARRSME<br>LIAREDENPKVAEVI<br>YPIMQVNAIHYAGVD<br>VAVGGMEQRKIHMLA<br>RELLPKKVVCIHNPV<br>LTGLDGEGKMSSSKG<br>NFIAVDDSPEEIRAK<br>IKKAYCPAGVVEGNP<br>IMEIAKYFLEYPLTI<br>KRPEKFGGDLTVNSY<br>EELESLFKNKELHPM<br>DLKNAVAEELIKILE<br>PIRKRL |
| 5 | pPRO-PheRS-1 nucleotide sequence | ATGGACGAATTTGAA<br>ATGATAAAGAGAAAC<br>ACATCTGAAATTATC<br>AGCGAGGAAGAGTTA<br>AGAGAGGTTTTAAAA |

TABLE 4-continued

| SEQ ID NO: | Description | SEQUENCE |
|---|---|---|
| | | AAAGATGAAAAAATCT<br>GCT**GCG**ATAGGTTTT<br>GAACCAAGTGGTAAA<br>ATACATTTAGGGCAT<br>TATCTCCAAATAAAA<br>AAGATGATTGATTTA<br>CAAAATGCTGGATTT<br>GATATAATTATATTG<br>TTGGCTGATTTACAC<br>GCCTATTTAAACCAG<br>AAAGGAGAGTTGGAT<br>GAGATTAGAAAAATA<br>GGAGATTATAACAAA<br>AAAGTTTTTGAAGCA<br>ATGGGGTTAAAGGCA<br>AAATATGTTTATGGA<br>AGT**CCG**TTCCAG**TTT**<br>GATAAGGATTATACA<br>CTGAATGTCTATAGA<br>TTGGCTTTAAAAACT<br>ACCTTAAAAAGAGCA<br>AGAAGGAGTATGGAA<br>CTTATAGCAAGAGAG<br>GATGAAAATCCAAAG<br>GTTGCTGAAGTTATC<br>TATCCAATAATGCAG<br>GTTAAT**GCAATT**CAT<br>TAT**GCT**GGCGTTGAT<br>GTTGCAGTTGGAGGG<br>ATGGAGCAGAGAAAA<br>ATACACATGTTAGCA<br>AGGGAGCTTTTACCA<br>AAAAAGGTTGTTTGT<br>ATTCACAACCCTGTC<br>TTAACGGGTTTGGAT<br>GGAGAAGGAAAGATG<br>AGTTCTTCAAAAGGG<br>AATTTTATAGCTGTT<br>GATGACTCTCCAGAA<br>GAGATTAGGGCTAAG<br>ATAAAGAAAGCATAC<br>TGCCCAGCTGGAGTT<br>GTTGAAGGAAATCCA<br>ATAATGGAGATAGCT<br>AAATACTTCCTTGAA<br>TATCCTTTAACCATA<br>AAAAGGCCAGAAAAA<br>TTTGGTGGAGATTTG<br>ACAGTTAATAGCTAT<br>GAGGAGTTAGAGAGT<br>TTATTTAAAAATAAG<br>GAATTGCATCCAATG<br>GATTTAAAAAATGCT<br>GTAGCTGAAGAACTT<br>ATAAAGATTTTAGAG<br>CCAATTAGAAAGAGA<br>TTA |
| 6 | pPRO-PheRS-2; para-propargyloxyphenylalanine aminoacyl-tNRA synthetase isolate-2 amino acid sequence, having amino acid changes:<br>Tyr32→Ala32<br>Glu107→Lys107<br>Asp158→Ala158<br>Leu162→Ala162<br>derived from wild-type *Methanococcus jannaschii* tyrosyl tRNA-synthetase | MDEFEMIKRNTSEII<br>SEEELREVLKKDEKS<br>A**A**IGFEPSGKIHLGH<br>YLQIKKMIDLQNAGF<br>DIIILLADLHAYLNQ<br>KGELDEIRKIGDYNK<br>KVFEAMGLKAKYVYG<br>S**K**FQ**L**DKDYTLNVYR<br>LALKTTLKRARRSME<br>LIAREDENPKVAEVI<br>YPIMQVN**AI**HY**A**GVD<br>VAVGGMEQRKIHMLA<br>RELLPKKVVCIHNPV<br>LTGLDGEGKMSSSKG<br>NFIAVDDSPEEIRAK<br>IKKAYCPAGVVEGNP<br>IMEIAKYFLEYPLTI<br>KRPEKFGGDLTVNSY<br>EELESLFKNKELHPM<br>DLKNAVAEELIKILE<br>PIRKRL |
| 7 | pPRO-PheRS-2 nucleotide sequence | ATGGACGAATTTGAA<br>ATGATAAAGAGAAAC<br>ACATCTGAAATTATC<br>AGCGAGGAAGAGTTA<br>AGAGAGGTTTTAAAA<br>AAAGATGAAAAAATCT<br>GCT**GCG**ATAGGTTTT<br>GAACCAAGTGGTAAA<br>ATACATTTAGGGCAT<br>TATCTCCAAATAAAA<br>AAGATGATTGATTTA<br>CAAAATGCTGGATTT<br>GATATAATTATATTG<br>TTGGCTGATTTACAC<br>GCCTATTTAAACCAG<br>AAAGGAGAGTTGGAT<br>GAGATTAGAAAAATA<br>GGAGATTATAACAAA<br>AAAGTTTTTGAAGCA<br>ATGGGGTTAAAGGCA<br>AAATATGTTTATGGA<br>AGT**AAG**TTCCAG**CTT**<br>GATAAGGATTATACA<br>CTGAATGTCTATAGA<br>TTGGCTTTAAAAACT<br>ACCTTAAAAAGAGCA<br>AGAAGGAGTATGGAA<br>CTTATAGCAAGAGAG<br>GATGAAAATCCAAAG<br>GTTGCTGAAGTTATC<br>TATCCAATAATGCAG<br>GTTAAT**GCAATT**CAT<br>TAT**GCT**GGCGTTGAT<br>GTTGCAGTTGGAGGG<br>ATGGAGCAGAGAAAA<br>ATACACATGTTAGCA<br>AGGGAGCTTTTACCA<br>AAAAAGGTTGTTTGT<br>ATTCACAACCCTGTC<br>TTAACGGGTTTGGAT<br>GGAGAAGGAAAGATG<br>AGTTCTTCAAAAGGG<br>AATTTTATAGCTGTT<br>GATGACTCTCCAGAA<br>GAGATTAGGGCTAAG<br>ATAAAGAAAGCATAC<br>TGCCCAGCTGGAGTT<br>GTTGAAGGAAATCCA<br>ATAATGGAGATAGCT<br>AAATACTTCCTTGAA<br>TATCCTTTAACCATA<br>AAAAGGCCAGAAAAA<br>TTTGGTGGAGATTTG<br>ACAGTTAATAGCTAT<br>GAGGAGTTAGAGAGT<br>TTATTTAAAAATAAG<br>GAATTGCATCCAATG<br>GATTTAAAAAATGCT<br>GTAGCTGAAGAACTT<br>ATAAAGATTTTAGAG<br>CCAATTAGAAAGAGA<br>TTA |
| 8 | pPRO-PheRS-3; para-propargyloxyphenylalanine aminoacyl-tNRA synthetase isolate-3 amino acid sequence, having amino acid changes:<br>Tyr32→Ala32<br>Glu107→Arg107<br>Asp158→Ala158 | MDEFEMIKRNTSEII<br>SEEELREVLKKDEKS<br>A**A**IGFEPSGKIHLGH<br>YLQIKKMIDLQNAGF<br>DIIILLADLHAYLNQ<br>KGELDEIRKIGDYNK<br>KVFEAMGLKAKYVYG<br>S**R**FQ**L**DKDYTLNVYR<br>LALKTTLKRARRSME |

TABLE 4-continued

| SEQ ID NO: | Description | SEQUENCE |
|---|---|---|
| | Leu162→Pro162 derived from wild-type *Methanococcus jannaschii* tyrosyl tRNA-synthetase | LIAREDENPKVAEVI<br>YPIMQVN**AI**HY**P**GVD<br>VAVGGMEQRKIHMLA<br>RELLPKKVVCIHNPV<br>LTGLDGEGKMSSSKG<br>NFIAVDDSPEEIRAK<br>IKKAYCPAGVVEGNP<br>IMEIAKYFLEYPLTI<br>KRPEKFGGDLTVNSY<br>EELESLFKNKELHPM<br>DLKNAVAEELIKILE<br>PIRKRL |
| 9 | pPRO-PheRS-3 nucleotide sequence | ATGGACGAATTTGAA<br>ATGATAAAGAGAAAC<br>ACATCTGAAATTATC<br>AGCGAGGAAGAGTTA<br>AGAGAGGTTTTAAAA<br>AAAGATGAAAAATCT<br>GCT**GCG**ATAGGTTTT<br>GAACCAAGTGGTAAA<br>ATACATTTAGGGCAT<br>TATCTCCAAATAAAA<br>AAGATGATTGATTTA<br>CAAAATGCTGGATTT<br>GATATAATTATATTG<br>TTGGCTGATTTACAC<br>GCCTATTTAAACCAG<br>AAAGGAGAGTTGGAT<br>GAGATTAGAAAAATA<br>GGAGATTATAACAAA<br>AAAGTTTTTGAAGCA<br>ATGGGGTTAAAGGCA<br>AAATATGTTTATGGA<br>AGT**CGG**TTCCAG**CTT**<br>GATAAGGATTATACA<br>CTGAATGTCTATAGA<br>TTGGCTTTAAAAACT<br>ACCTTAAAAAGAGCA<br>AGAAGGAGTATGGAA<br>CTTATAGCAAGAGAG<br>GATGAAAATCCAAAG<br>GTTGCTGAAGTTATC<br>TATCCAATAATGCAG<br>GTTAAT**GCAATT**CAT<br>TAT**CCG**GGCGTTGAT<br>GTTGCAGTTGGAGGG<br>ATGGAGCAGAGAAAA<br>ATACACATGTTAGCA<br>AGGGAGCTTTTACCA<br>AAAAAGGTTGTTTGT<br>ATTCACAACCCTGTC<br>TTAACGGGTTTGGAT<br>GGAGAAGGAAAGATG<br>AGTTCTTCAAAAGGG<br>AATTTTATAGCTGTT<br>GATGACTCTCCAGAA<br>GAGATTAGGGCTAAG<br>ATAAAGAAAGCATAC<br>TGCCCAGCTGGAGTT<br>GTTGAAGGAAATCCA<br>ATAATGGAGATAGCT<br>AAATACTTCCTTGAA<br>TATCCTTTAACCATA<br>AAAAGGCCAGAAAAA<br>TTTGGTGGAGATTTG<br>ACAGTTAATAGCTAT<br>GAGGAGTTAGAGAGT<br>TTATTTAAAAATAAG<br>GAATTGCATCCAATG<br>GATTTAAAAAATGCT<br>GTAGCTGAAGAACTT<br>ATAAAGATTTTAGAG<br>CCAATTAGAAAGAGA<br>TTA |
| 10 | pPRO-PheRS-4; para-propargyloxyphenylalanine aminoacyl-tNRA synthetase isolate-4 amino acid sequence, having amino acid changes:<br>Tyr32→His32<br>Glu107→Ala107<br>Asp158→Ala158<br>Leu162→Pro162<br>derived from wild-type *Methanococcus jannaschii* tyrosyl tRNA-synthetase | MDEFEMIKRNTSEII<br>SEEELREVLKKDEKS<br>A**H**IGFEPSGKIHLGH<br>YLQIKKMIDLQNAGF<br>DIIILLADLHAYLNQ<br>KGELDEIRKIGDYNK<br>KVFEAMGLKAKYVYG<br>S**A**FQ**L**DKDYTLNVYR<br>LALKTTLKRARRSME<br>LIAREDENPKVAEVI<br>YPIMQVN**AI**HY**P**GVD<br>VAVGGMEQRKIHMLA<br>RELLPKKVVCIHNPV<br>LTGLDGEGKMSSSKG<br>NFIAVDDSPEEIRAK<br>IKKAYCPAGVVEGNP<br>IMEIAKYFLEYPLTI<br>KRPEKFGGDLTVNSY<br>EELESLFKNKELHPM<br>DLKNAVAEELIKILE<br>PIRKRL |
| 11 | pPRO-PheRS-4 nucleotide sequence | ATGGACGAATTTGAA<br>ATGATAAAGAGAAAC<br>ACATCTGAAATTATC<br>AGCGAGGAAGAGTTA<br>AGAGAGGTTTTAAAA<br>AAAGATGAAAAATCT<br>GCT**CAT**ATAGGTTTT<br>GAACCAAGTGGTAAA<br>ATACATTTAGGGCAT<br>TATCTCCAAATAAAA<br>AAGATGATTGATTTA<br>CAAAATGCTGGATTT<br>GATATAATTATATTG<br>TTGGCTGATTTACAC<br>GCCTATTTAAACCAG<br>AAAGGAGAGTTGGAT<br>GAGATTAGAAAAATA<br>GGAGATTATAACAAA<br>AAAGTTTTTGAAGCA<br>ATGGGGTTAAAGGCA<br>AAATATGTTTATGGA<br>AGT**GCT**TTCCAG**CTT**<br>GATAAGGATTATACA<br>CTGAATGTCTATAGA<br>TTGGCTTTAAAAACT<br>ACCTTAAAAAGAGCA<br>AGAAGGAGTATGGAA<br>CTTATAGCAAGAGAG<br>GATGAAAATCCAAAG<br>GTTGCTGAAGTTATC<br>TATCCAATAATGCAG<br>GTTAAT**GCAATT**CAT<br>TAT**CCT**GGCGTTGAT<br>GTTGCAGTTGGAGGG<br>ATGGAGCAGAGAAAA<br>ATACACATGTTAGCA<br>AGGGAGCTTTTACCA<br>AAAAAGGTTGTTTGT<br>ATTCACAACCCTGTC<br>TTAACGGGTTTGGAT<br>GGAGAAGGAAAGATG<br>AGTTCTTCAAAAGGG<br>AATTTTATAGCTGTT<br>GATGACTCTCCAGAA<br>GAGATTAGGGCTAAG<br>ATAAAGAAAGCATAC<br>TGCCCAGCTGGAGTT<br>GTTGAAGGAAATCCA<br>ATAATGGAGATAGCT<br>AAATACTTCCTTGAA<br>TATCCTTTAACCATA<br>AAAAGGCCAGAAAAA<br>TTTGGTGGAGATTTG<br>ACAGTTAATAGCTAT |

TABLE 4-continued

| SEQ ID NO: | Description | SEQUENCE |
|---|---|---|
| | | GAGGAGTTAGAGAGT<br>TTATTTAAAAATAAG<br>GAATTGCATCCAATG<br>GATTTAAAAAATGCT<br>GTAGCTGAAGAACTT<br>ATAAAGATTTTAGAG<br>CCAATTAGAAAGAGA<br>TTA |
| 12 | pPRO-PheRS-5; para-propargyloxyphenylalanine aminoacyl-tNRA synthetase isolate-5 amino acid sequence, having amino acid changes:<br>Tyr32→Ser32<br>Glu107→Gln107<br>Asp158→Ala158<br>Leu162→Ala162<br>derived from wild-type *Methanococcus jannaschii* tyrosyl tRNA-synthetase | MDEFEMIKRNTSEII<br>SEEELREVLKKDEKS<br>A**S**IGFEPSGKIHLGH<br>YLQIKKMIDLQNAGF<br>DIIILLADLHAYLNQ<br>KGELDEIRKIGDYNK<br>KVFEAMGLKAKYVYG<br>S**Q**FQ**L**DKDYTLNVYR<br>LALKTTLKRARRSME<br>LIAREDENPKVAEVI<br>YPIMQVN**AI**HY**A**GVD<br>VAVGGMEQRKIHMLA<br>RELLPKKVVCIHNPV<br>LTGLDGEGKMSSSKG<br>NFIAVDDSPEEIRAK<br>IKKAYCPAGVVEGNP<br>IMEIAKYFLEYPLTI<br>KRPEKFGGDLTVNSY<br>EELESLFKNKELHPM<br>DLKNAVAEELIKILE<br>PIRKRL |
| 13 | pPRO-PheRS-5 nucleotide sequence | ATGGACGAATTTGAA<br>ATGATAAAGAGAAAC<br>ACATCTGAAATTATC<br>AGCGAGGAAGAGTTA<br>AGAGAGGTTTTAAAA<br>AAAGATGAAAAATCT<br>GCT**TCG**ATAGGTTTT<br>GAACCAAGTGGTAAA<br>ATACATTTAGGGCAT<br>TATCTCCAAATAAAA<br>AAGATGATTGATTTA<br>CAAAATGCTGGATTT<br>GATATAATTATATTG<br>TTGGCTGATTTACAC<br>GCCTATTTAAACCAG<br>AAAGGAGAGTTGGAT<br>GAGATTAGAAAAATA<br>GGAGATTATAACAAA<br>AAAGTTTTTGAAGCA<br>ATGGGGTTAAAGGCA<br>AAATATGTTTATGGA<br>AGT**CAG**TTCCAG**CTT**<br>GATAAGGATTATACA<br>CTGAATGTCTATAGA<br>TTGGCTTTAAAAACT<br>ACCTTAAAAAGAGCA<br>AGAAGGAGTATGGAA<br>CTTATAGCAAGAGAG<br>GATGAAAATCCAAAG<br>GTTGCTGAAGTTATC<br>TATCCAATAATGCAG<br>GTTAAT**GCAATT**CAT<br>TAT**GCC**GGCGTTGAT<br>GTTGCAGTTGGAGGG<br>ATGGAGCAGAGAAAA<br>ATACACATGTTAGCA<br>AGGGAGCTTTTACCA<br>AAAAAGGTTGTTTGT<br>ATTCACAACCCTGTC<br>TTAACGGGTTTGGAT<br>GGAGAAGGAAAGATG<br>AGTTCTTCAAAAGGG<br>AATTTTATAGCTGTT<br>GATGACTCTCCAGAA<br>GAGATTAGGGCTAAG |

TABLE 4-continued

| SEQ ID NO: | Description | SEQUENCE |
|---|---|---|
| | | ATAAAGAAAGCATAC<br>TGCCCAGCTGGAGTT<br>GTTGAAGGAAATCCA<br>ATAATGGAGATAGCT<br>AAATACTTCCTTGAA<br>TATCCTTTAACCATA<br>AAAAGGCCAGAAAAA<br>TTTGGTGGAGATTTG<br>ACAGTTAATAGCTAT<br>GAGGAGTTAGAGAGT<br>TTATTTAAAAATAAG<br>GAATTGCATCCAATG<br>GATTTAAAAAATGCT<br>GTAGCTGAAGAACTT<br>ATAAAGATTTTAGAG<br>CCAATTAGAAAGAGA<br>TTA |
| 14 | pPRO-PheRS-6; para-propargyloxyphenylalanine aminoacyl-tNRA synthetase isolate-6 amino acid sequence, having amino acid changes:<br>Tyr32→Thr32<br>Glu107→Ser107<br>Asp159→Leu159<br>Leu162→Pro162<br>derived from wild-type *Methanococcus jannaschii* tyrosyl tRNA-synthetase | MDEFEMIKRNTSEII<br>SEEELREVLKKDEKS<br>A**T**IGFEPSGKIHLGH<br>YLQIKKMIDLQNAGF<br>DIIILLADLHAYLNQ<br>KGELDEIRKIGDYNK<br>KVFEAMGLKAKYVYG<br>S**S**FQ**L**DKDYTLNVYR<br>LALKTTLKRARRSME<br>LIAREDENPKVAEVI<br>YPIMQVN**LH**HY**P**GVD<br>VAVGGMEQRKIHMLA<br>RELLPKKVVCIHNPV<br>LTGLDGEGKMSSSKG<br>NFIAVDDSPEEIRAK<br>IKKAYCPAGVVEGNP<br>IMEIAKYFLEYPLTI<br>KRPEKFGGDLTVNSY<br>EELESLFKNKELHPM<br>DLKNAVAEELIKILE<br>PIRKRL |
| 15 | pPRO-PheRS-6 nucleotide sequence | ATGGACGAATTTGAA<br>ATGATAAAGAGAAAC<br>ACATCTGAAATTATC<br>AGCGAGGAAGAGTTA<br>AGAGAGGTTTTAAAA<br>AAAGATGAAAAATCT<br>GCT**AGC**ATAGGTTTT<br>GAACCAAGTGGTAAA<br>ATACATTTAGGGCAT<br>TATCTCCAAATAAAA<br>AAGATGATTGATTTA<br>CAAAATGCTGGATTT<br>GATATAATTATATTG<br>TTGGCTGATTTACAC<br>GCCTATTTAAACCAG<br>AAAGGAGAGTTGGAT<br>GAGATTAGAAAAATA<br>GGAGATTATAACAAA<br>AAAGTTTTTGAAGCA<br>ATGGGGTTAAAGGCA<br>AAATATGTTTATGGA<br>AGT**TCG**TTCCAG**CTT**<br>GATAAGGATTATACA<br>CTGAATGTCTATAGA<br>TTGGCTTTAAAAACT<br>ACCTTAAAAAGAGCA<br>AGAAGGAGTATGGAA<br>CTTATAGCAAGAGAG<br>GATGAAAATCCAAAG<br>GTTGCTGAAGTTATC<br>TATCCAATAATGCAG<br>GTTAAT**GCAATT**CAT<br>TAT**CCG**GGCGTTGAT<br>GTTGCAGTTGGAGGG<br>ATGGAGCAGAGAAAA<br>ATACACATGTTAGCA |

TABLE 4-continued

| SEQ ID NO: | Description | SEQUENCE |
|---|---|---|
| | | AGGGAGCTTTTACCA<br>AAAAAGGTTGTTTGT<br>ATTCACAACCCTGTC<br>TTAACGGGTTTGGAT<br>GGAGAAGGAAAGATG<br>AGTTCTTCAAAAGGG<br>AATTTTATAGCTGTT<br>GATGACTCTCCAGAA<br>GAGATTAGGGCTAAG<br>ATAAAGAAAGCATAC<br>TGCCCAGCTGGAGTT<br>GTTGAAGGAAATCCA<br>ATAATGGAGATAGCT<br>AAATACTTCCTTGAA<br>TATCCTTTAACCATA<br>AAAAGGCCAGAAAAA<br>TTTGGTGGAGATTTG<br>ACAGTTAATAGCTAT<br>GAGGAGTTAGAGAGT<br>TTATTTAAAAATAAG<br>GAATTGCATCCAATG<br>GATTTAAAAAATGCT<br>GTAGCTGAAGAACTT<br>ATAAAGATTTTAGAG<br>CCAATTAGAAAGAGA<br>TTA |
| 16 | pPRO-PheRS-7; para-propargyloxyphenylalanine aminoacyl-tNRA synthetase isolate-7 amino acid sequence, having amino acid changes:<br>Tyr32→Ala32<br>Glu107→Gln107<br>Asp158→Pro158<br>Ile159→Gly159<br>Leu162→Thr162<br>derived from wild-type *Methanococcus jannaschii* tyrosyl tRNA-synthetase | MDEFEMIKRNTSEII<br>SEEELREVLKKDEKS<br>A**A**IGFEPSGKIHLGH<br>YLQIKKMIDLQNAGF<br>DIIILLADLHAYLNQ<br>KGELDEIRKIGDYNK<br>KVFEAMGLKAKYVYG<br>S**Q**FQ**L**DKDYTLNVYR<br>LALKTTLKRARRSME<br>LIAREDENPKVAEVI<br>YPIMQVN**PG**HY**T**GVD<br>VAVGGMEQRKIHMLA<br>RELLPKKVVCIHNPV<br>LTGLDGEGKMSSSKG<br>NFIAVDDSPEEIRAK<br>IKKAYCPAGVVEGNP<br>IMEIAKYFLEYPLTI<br>KRPEKFGGDLTVNSY<br>EELESLFKNKELHPM<br>DLKNAVAEELIKILE<br>PIRKRL |
| 17 | pPRO-PheRS-7 nucleotide sequence | ATGGACGAATTTGAA<br>ATGATAAAGAGAAAC<br>ACATCTGAAATTATC<br>AGCGAGGAAGAGTTA<br>AGAGAGGTTTTAAAA<br>AAAGATGAAAAATCT<br>GCT**GCT**ATAGGTTTT<br>GAACCAAGTGGTAAA<br>ATACATTTAGGGCAT<br>TATCTCCAAATAAAA<br>AAGATGATTGATTTA<br>CAAAATGCTGGATTT<br>GATATAATTATATTG<br>TTGGCTGATTTACAC<br>GCCTATTTAAACCAG<br>AAAGGAGAGTTGGAT<br>GAGATTAGAAAAATA<br>GGAGATTATAACAAA<br>AAAGTTTTTGAAGCA<br>ATGGGGTTAAAGGCA<br>AAATATGTTTATGGA<br>AGT**CAG**TTCCAG**CTT**<br>GATAAGGATTATACA<br>CTGAATGTCTATAGA<br>TTGGCTTTAAAAACT<br>ACCTTAAAAAGAGCA<br>AGAAGGAGTATGGAA<br>CTTATAGCAAGAGAG<br>GATGAAAATCCAAAG<br>GTTGCTGAAGTTATC<br>TATCCAATAATGCAG<br>GTTAAT**CCGGGG**CAT<br>TAT**ACG**GGCGTTGAT<br>GTTGCAGTTGGAGGG<br>ATGGAGCAGAGAAAA<br>ATACACATGTTAGCA<br>AGGGAGCTTTTACCA<br>AAAAAGGTTGTTTGT<br>ATTCACAACCCTGTC<br>TTAACGGGTTTGGAT<br>GGAGAAGGAAAGATG<br>AGTTCTTCAAAAGGG<br>AATTTTATAGCTGTT<br>GATGACTCTCCAGAA<br>GAGATTAGGGCTAAG<br>ATAAAGAAAGCATAC<br>TGCCCAGCTGGAGTT<br>GTTGAAGGAAATCCA<br>ATAATGGAGATAGCT<br>AAATACTTCCTTGAA<br>TATCCTTTAACCATA<br>AAAAGGCCAGAAAAA<br>TTTGGTGGAGATTTG<br>ACAGTTAATAGCTAT<br>GAGGAGTTAGAGAGT<br>TTATTTAAAAATAAG<br>GAATTGCATCCAATG<br>GATTTAAAAAATGCT<br>GTAGCTGAAGAACTT<br>ATAAAGATTTTAGAG<br>CCAATTAGAAAGAGA<br>TTA |
| 18 | pPRO-PheRS-8; para-propargyloxyphenylalanine aminoacyl-tNRA synthetase isolate-8 amino acid sequence, having amino acid changes:<br>Tyr32→Ala32<br>Glu107→Pro107<br>Asp158→Ser158<br>Ile159→Leu159<br>Leu162→His162<br>derived from wild-type *Methanococcus jannaschii* tyrosyl tRNA-synthetase | MDEFEMIKRNTSEII<br>SEEELREVLKKDEKS<br>A**A**IGFEPSGKIHLGH<br>YLQIKKMIDLQNAGF<br>DIIILLADLHAYLNQ<br>KGELDEIRKIGDYNK<br>KVFEAMGLKAKYVYG<br>S**P**FQ**L**DKDYTLNVYR<br>LALKTTLKRARRSME<br>LIAREDENPKVAEVI<br>YPIMQVN**SL**HY**H**GVD<br>VAVGGMEQRKIHMLA<br>RELLPKKVVCIHNPV<br>LTGLDGEGKMSSSKG<br>NFIAVDDSPEEIRAK<br>IKKAYCPAGVVEGNP<br>IMEIAKYFLEYPLTI<br>KRPEKFGGDLTVNSY<br>EELESLFKNKELHPM<br>DLKNAVAEELIKILE<br>PIRKRL |
| 19 | pPRO-PheRS-8 nucleotide sequence | ATGGACGAATTTGAA<br>ATGATAAAGAGAAAC<br>ACATCTGAAATTATC<br>AGCGAGGAAGAGTTA<br>AGAGAGGTTTTAAAA<br>AAAGATGAAAAATCT<br>GCT**GCT**ATAGGTTTT<br>GAACCAAGTGGTAAA<br>ATACATTTAGGGCAT<br>TATCTCCAAATAAAA<br>AAGATGATTGATTTA<br>CAAAATGCTGGATTT<br>GATATAATTATATTG<br>TTGGCTGATTTACAC<br>GCCTATTTAAACCAG<br>AAAGGAGAGTTGGAT<br>GAGATTAGAAAAATA<br>GGAGATTATAACAAA |

TABLE 4-continued

| SEQ ID NO: | Description | SEQUENCE |
|---|---|---|
| | | AAAGTTTTTGAAGCA<br>ATGGGGTTAAAGGCA<br>AAATATGTTTATGGA<br>AGT**CCT**TTCCAG**CTT**<br>GATAAGGATTATACA<br>CTGAATGTCTATAGA<br>TTGGCTTTAAAAACT<br>ACCTTAAAAAGAGCA<br>AGAAGGAGTATGGAA<br>CTTATAGCAAGAGAG<br>GATGAAAATCCAAAG<br>GTTGCTGAAGTTATC<br>TATCCAATAATGCAG<br>GTTAAT**TCTCTG**CAT<br>TAT**CAT**GGCGTTGAT<br>GTTGCAGTTGGAGGG<br>ATGGAGCAGAGAAAA<br>ATACACATGTTAGCA<br>AGGGAGCTTTTACCA<br>AAAAAGGTTGTTTGT<br>ATTCACAACCCTGTC<br>TTAACGGGTTTGGAT<br>GGAGAAGGAAAGATG<br>AGTTCTTCAAAAGGG<br>AATTTTATAGCTGTT<br>GATGACTCTCCAGAA<br>GAGATTAGGGCTAAG<br>ATAAAGAAAGCATAC<br>TGCCCAGCTGGAGTT<br>GTTGAAGGAAATCCA<br>ATAATGGAGATAGCT<br>AAATACTTCCTTGAA<br>TATCCTTTAACCATA<br>AAAAGGCCAGAAAAA<br>TTTGGTGGAGATTTG<br>ACAGTTAATAGCTAT<br>GAGGAGTTAGAGAGT<br>TTATTTAAAAATAAG<br>GAATTGCATCCAATG<br>GATTTAAAAAATGCT<br>GTAGCTGAAGAACTT<br>ATAAAGATTTTAGAG<br>CCAATTAGAAAGAGA<br>TTA |
| 20 | Mutant myoglobin (74-TAG) tryptic peptide used in mass spectrometry analysis | HGVTVLTALGY*ILK |
| 21 | pPRO-PheRS-consensus; para-propargyloxyphenyl-alanine aminoacyl-tRNA synthetase amino acid sequence consensus | MDEFEMIKRNTSEII<br>SEEELREVLKKDEKS<br>A**A**IGFEPSGKIHLGH<br>YLQIKKMIDLQNAGF<br>DIIILLADLHAYLNQ<br>KGELDEIRKIGDYNK<br>KVFEAMGLKAKYVYG<br>S[**P/Q**]FQLDKDYTL<br>NVYRLALKTTLKRAR<br>RSMELIAREDENPKV<br>AEVIAEVIYPIMQVN<br>**A**IHY[**A/P**]GVD<br>VAVGGMEQRKIHMLA<br>RELLPKKVVCIHNPV<br>LTGLDGEGKMSSSKG<br>NFIAVDDSPEEIRAK<br>IKKAYCPAGVVEGNP<br>IMEIAKYFLEYPLTI<br>KRPEKFGGDLTVNSY<br>EELESLFKNKELHPM<br>DLKNAVAEELIKILE<br>PIRKRL |
| 22 | pPRO-PheRS-con1 | MDEFEMIKRNTSEII<br>SEEELREVLKKDEKS<br>A**A**IGFEPSGKIHLGH<br>YLQIKKMIDLQNAGF<br>DIIILLADLHAYLNQ<br>KGELDEIRKIGDYNK<br>KVFEAMGLKAKYVYG<br>S**P**FQLDKDYTLNVYR<br>LALKTTLKRARRSME<br>LIAREDENPKVAEVI<br>YPIMQVN**A**IHY**A**GVD<br>VAVGGMEQRKIHMLA<br>RELLPKKVVCIHNPV<br>LTGLDGEGKMSSSKG<br>NFIAVDDSPEEIRAK<br>IKKAYCPAGVVEGNP<br>IMEIAKYFLEYPLTI<br>KRPEKFGGDLTVNSY<br>EELESLFKNKELHPM<br>DLKNAVAEELIKILE<br>PIRKRL |
| 23 | pPRO-PheRS-con2 | MDEFEMIKRNTSEII<br>SEEELREVLKKDEKS<br>A**A**IGFEPSGKIHLGH<br>YLQIKKMIDLQNAGF<br>DIIILLADLHAYLNQ<br>KGELDEIRKIGDYNK<br>KVFEAMGLKAKYVYG<br>S**P**FQLDKDYTLNVYR<br>LALKTTLKRARRSME<br>LIAREDENPKVAEVI<br>YPIMQVN**A**IHY**P**GVD<br>VAVGGMEQRKIHMLA<br>RELLPKKVVCIHNPV<br>LTGLDGEGKMSSSKG<br>NFIAVDDSPEEIRAK<br>IKKAYCPAGVVEGNP<br>IMEIAKYFLEYPLTI<br>KRPEKFGGDLTVNSY<br>EELESLFKNKELHPM<br>DLKNAVAEELIKILE<br>PIRKRL |
| 24 | pPRO-PheRS-con3 | MDEFEMIKRNTSEII<br>SEEELREVLKKDEKS<br>A**A**IGFEPSGKIHLGH<br>YLQIKKMIDLQNAGF<br>DIIILLADLHAYLNQ<br>KGELDEIRKIGDYNK<br>KVFEAMGLKAKYVYG<br>S**Q**FQLDKDYTLNVYR<br>LALKTTLKRARRSME<br>LIAREDENPKVAEVI<br>YPIMQVN**A**IHY**A**GVD<br>VAVGGMEQRKIHMLA<br>RELLPKKVVCIHNPV<br>LTGLDGEGKMSSSKG<br>NFIAVDDSPEEIRAK<br>IKKAYCPAGVVEGNP<br>IMEIAKYFLEYPLTI<br>KRPEKFGGDLTVNSY<br>EELESLFKNKELHPM<br>DLKNAVAEELIKILE<br>PIRKRL |
| 25 | pPRO-PheRS-con4 | MDEFEMIKRNTSEII<br>SEEELREVLKKDEKS<br>A**A**IGFEPSGKIHLGH<br>YLQIKKMIDLQNAGF<br>DIIILLADLHAYLNQ<br>KGELDEIRKIGDYNK<br>KVFEAMGLKAKYVYG<br>S**P**FQLDKDYTLNVYR<br>LALKTTLKRARRSME<br>LIAREDENPKVAEVI<br>YPIMQVN**A**IHY**P**GVD<br>VAVGGMEQRKIHMLA<br>RELLPKKVVCIHNPV |

TABLE 4-continued

| SEQ ID NO: | Description | SEQUENCE |
|---|---|---|
| | | LTGLDGEGKMSSSKG NFIAVDDSPEEIRAK IKKAYCPAGVVEGNP IMEIAKYFLEYPLTI |

TABLE 4-continued

| SEQ ID NO: | Description | SEQUENCE |
|---|---|---|
| | | KRPEKFGGDLTVNSY EELESLFKNKELHPM DLKNAVAEELIKILE PIRKRL |

What is claimed is:

1. A eubacterial cell comprising a first orthogonal aminoacyl-tRNA synthetase (O-RS) that functions in the cell, wherein the O-RS preferentially aminoacylates a first orthogonal tRNA (O-tRNA) with a first unnatural amino acid that is an alkynyl amino acid;

wherein said first O-RS is at least 90% identical to the wild-type *Methanococcus jannaschii* tyrosyl-tRNA synthetase having the amino acid sequence of SEQ ID NO: 2, wherein the O-RS has an amino acid sequence comprising:

(a) alanine at amino acid position 32;

(b) alanine or Leu at amino acid position 158; and (c) alanine or proline at amino acid position 162; and, wherein the alkynyl amino acid is a para-substituted tyrosine or a para-substituted phenylalanine.

2. The cell of claim 1, wherein the eubacterial cell is an *E. coli* cell.

3. The cell of claim 1, wherein the O-RS is derived from a *Methanococcus jannaschii* aminoacyl-tRNA synthetase.

4. The cell of claim 1, wherein the O-RS is derived from a *Methanococcus jannaschii* tyrosyl-tRNA synthetase.

5. The cell of claim 1, wherein the O-RS is derived from the wild-type *Methanococcus jannaschii* tyrosyl-tRNA synthetase having the amino acid sequence of SEQ ID NO: 2.

6. The cell of claim 1, wherein the O-RS comprises an amino acid sequence selected from the group consisting of SEQ ID NOs: 4, 6, 8, 10, 12, 14, 16, and 18.

7. The cell of claim 1, wherein the cell comprises a polynucleotide encoding the O-RS, wherein the O-RS comprises an amino acid sequence selected from the group consisting of SEQ ID NOs: 4, 6, 8, 10, 12, 14, 16, and 18.

8. The cell of claim 7, wherein the polynucleotide is selected from the nucleotide sequences of SEQ ID NO: 5, 7, 9, 11, 13, 15, 17 or 19.

9. The cell of claim 1, wherein the O-tRNA is an amber suppressor tRNA.

10. The cell of claim 1, wherein the O-tRNA comprises or is encoded by a polynucleotide sequence set forth in SEQ ID NO: 1.

11. The cell of claim 1, wherein said alkynyl amino acid is para -propargyloxyphenylalanine.

12. The cell of claim 1, comprising a nucleic acid comprising at least one selector codon, wherein said selector codon is recognized by said first O-tRNA.

13. The cell of claim 12, comprising a second O-RS and a second O-tRNA, wherein the second O-RS preferentially aminoacylates the second O-tRNA with a second unnatural amino acid that is different from the first unnatural amino acid, and wherein the second O-tRNA recognizes a selector codon that is different from the selector codon recognized by the first O-tRNA.

14. The cell of claim 1, comprising said alkynyl amino acid.

15. The cell of claim 14, wherein said alkynyl amino acid is para-propargyloxyphenylalanine.

16. The cell of claim 1, comprising a translation system.

17. The cell of claim 16, said translation system comprising:

(a) said O-RS;

(b) said O-tRNA;

(c) a nucleic acid encoding a polypeptide of interest, the nucleic acid comprising at least one selector codon, wherein the selector codon is recognized by said O-tRNA; and, (d) an alkynyl amino acid, wherein said O-RS is capable of charging said O-tRNA with said alkynyl amino acid.

* * * * *

UNITED STATES PATENT AND TRADEMARK OFFICE

CERTIFICATE OF CORRECTION

PATENT NO. : 7,824,893 B2
APPLICATION NO. : 11/663513
DATED : November 2, 2010
INVENTOR(S) : Deiters et al.

It is certified that error appears in the above-identified patent and that said Letters Patent is hereby corrected as shown below:

In the Specification

Column 1, Lines 20-26, the paragraph STATEMENT AS TO RIGHTS TO INVENTIONS MADE UNDER FEDERALLY SPONSORED RESEARCH AND DEVELOPMENT should be changed to:
-- STATEMENT OF GOVERNMENT LICENSE RIGHTS
This invention was made with government support under grant number GM062159 awarded by the National Institutes of Health. The government has certain rights in the invention. --

Signed and Sealed this
Seventh Day of April, 2020

Andrei Iancu
*Director of the United States Patent and Trademark Office*